United States Patent
Freyne et al.

(10) Patent No.: US 7,560,458 B2
(45) Date of Patent: Jul. 14, 2009

(54) TRIAZOLOPYRIMIDINE DERIVATIVES AS GLYCOGEN SYNTHASE KINASE 3 INHIBITORS

(75) Inventors: Eddy Jean Edgard Freyne, Rumst (BE); Christopher John Love, Deurne (BE); Ludwig Paul Cooymans, Beerse (BE); Nele Vandermaesen, Olmen (BE); Peter Jacobus Johannes Antonius Buijnsters, Breda (NL); Marc Willems, Vosselaar (BE); Werner Constant Johan Embrechts, Beerse (BE)

(73) Assignee: Janssen Pharmaceutica, N.V., Beerse (BE)

( * ) Notice: Subject to any disclaimer, the term of this patent is extended or adjusted under 35 U.S.C. 154(b) by 212 days.

(21) Appl. No.: 10/564,844

(22) PCT Filed: Jul. 12, 2004

(86) PCT No.: PCT/EP2004/051455

§ 371 (c)(1),
(2), (4) Date: Jan. 13, 2006

(87) PCT Pub. No.: WO2005/012307

PCT Pub. Date: Feb. 10, 2005

(65) Prior Publication Data

US 2006/0205721 A1    Sep. 14, 2006

(30) Foreign Application Priority Data

Jul. 16, 2003  (EP)  ................ PCT/EP03/50310

(51) Int. Cl.
| | |
|---|---|
| *A61K 31/535* | (2006.01) |
| *A61K 31/501* | (2006.01) |
| *A61K 31/519* | (2006.01) |
| *A01N 43/90* | (2006.01) |
| *C07D 413/00* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 239/00* | (2006.01) |
| *C07D 471/00* | (2006.01) |
| *C07D 487/00* | (2006.01) |
| *C07D 491/00* | (2006.01) |

(52) U.S. Cl. ................ 514/234.5; 514/252.02; 514/252.16; 514/261.1; 544/114; 544/238; 544/254

(58) Field of Classification Search ................ None
See application file for complete search history.

(56) References Cited

U.S. PATENT DOCUMENTS 6,737,085 B2 *  5/2004  Nishibe et al. ............. 424/725

OTHER PUBLICATIONS

King, et. al.; 2001; Platinum on Carbon; Encyclopedia of Reaageants for Organic Synthesis; pp. 1-6.*
King, et. al.; 2001; Palladium on Carbon; Encyclopedia of Reaageants for Organic Synthesis; pp. 1-12.*
Mills, et. al.; 2001; Hydrochloric Acid; Encyclopedia of Reaageants for Organic Synthesis; pp. 1-13.*
Internal Medicine, 4th Edition, Editor-in-Chief Jay Stein, Chapters 71-72, pp. 699-715.*
Schiaffino et. al., J.Behav.Med., 1995, 18(6), p. 536.*
Cecil Textbook of Medicine, 21st Edition (2000), Goldman & Bennett (Editors), W.B. Saunders Company (Publisher), Chapter 198, pp. 1060-1074.*
Dille, et. al., Journal of Organic Chemistry, (1955), 20, 171-7.*

* cited by examiner

*Primary Examiner*—James O. Wilson
*Assistant Examiner*—Jeffrey H Murray
(74) *Attorney, Agent, or Firm*—Woodcock Washburn LLP

(57) ABSTRACT

This invention concerns compounds of formula

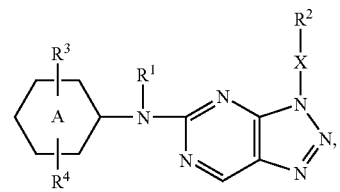

(I)

N-oxides, pharmaceutically acceptable addition salts, quaternary amines and stereochemically isomeric forms thereof, their use, pharmaceutical compositions comprising them, and processes for their preparation.

16 Claims, No Drawings

TRIAZOLOPYRIMIDINE DERIVATIVES AS GLYCOGEN SYNTHASE KINASE 3 INHIBITORS

CROSS-REFERENCE TO RELATED APPLICATIONS

This application is the national stage under 35 U.S.C. 371 of Application No. PCT/EP2004/051455, filed Jul. 12, 2004, which claims priority from PCT Patent Application No. PCT/EP03/50310 filed Jul. 16, 2003, and the present application claims priority and benefit of both of the aforesaid applications which are incorporated by reference herein.

FIELD OF THE INVENTION

The present invention concerns a novel group of compounds, their use as a medicine, their use for the manufacture of a medicament for the treatment of diseases mediated through glycogen synthase kinase 3 (GSK3), in particular glycogen synthase kinase 3α and 3β; processes for their preparation and pharmaceutical compositions comprising them.

BACKGROUND OF THE INVENTION

WO 00/62778 describes cyclic protein tyrosine kinase inhibitors. In particular, it discloses thiazolyl derivatives comprising a bicyclic ring system.

WO 01/44246 describes bicyclic pyrimidine and pyridine based compounds having GSK3 inhibiting activity.

WO 99/65897 describes pyrimidine and pyridine based compounds having GSK3 inhibiting activity.

WO 02/04450 describes purine derivatives having the activity of either inhibiting the formation of amyloid beta or stimulating the formation of sbeta-amyloid precursor protein.

WO 02/50073 describes pyrazolo[3,4-c]pyridines as GSK-3 inhibitors.

WO 2004/018473 relates to di-and trisubstituted 8-aza purine derivatives as cyclin-dependent kinase inhibitors.

JP 59062594 describes 3,5-disubstituted triazolopyrimidine compounds.

SUMMARY OF THE INVENTION

The present invention relates to compounds, which are distinguishable from the prior art in structure, pharmacological activity, potency, selectivity, solubility, permeability, metabolic stability.

The present invention concerns a compound of formula (I)

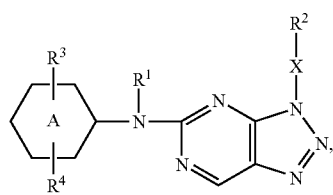

(I)

a N-oxide, a pharmaceutically acceptable addition salt, a quaternary amine and a stereochemically isomeric form thereof, wherein ring A represents phenyl, pyridyl, pyrimidinyl, pyridazinyl or pyrazinyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;

X represents a direct bond; —$(CH_2)_{n3}$— or —$(CH_2)_{n4}$—$X_{1a}$—$X_{1b}$—;
with $n_3$ representing an integer with value 1, 2, 3 or 4;
with $n_4$ representing an integer with value 1 or 2;
with $X_{1a}$ representing O, C(=O) or $NR^5$; and
with $X_{1b}$ representing a direct bond or $C_{1-2}$alkyl;

$R^2$ represents $C_{3-7}$cycloalkyl; phenyl; a 4, 5, 6- or 7-membered monocyclic heterocycle containing at least one heteroatom selected from O, S or N; benzoxazolyl or a radical of formula

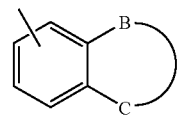

(a-1)

wherein —B—C— represents a bivalent radical of formula

—$CH_2$—$CH_2$—$CH_2$— (b-1);

—$CH_2$—$CH_2$—$CH_2$—$CH_2$— (b-2);

—$X_1$—$CH_2$—$CH_2$—$(CH_2)_n$— (b-3);

—$X_1$—$CH_2$—$(CH_2)_n$—$X_1$— (b-4);

—$X_1$—$(CH_2)_{n'}$—CH=CH— (b-5);

—CH=N—$X_1$— (b-6);

with $X_1$ representing O or $NR^5$;
n representing an integer with value 0, 1, 2 or 3;
n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkyl-carbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $c_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyl-oxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$lkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—

$NR^6R^7$, $-NR^5-C(=O)-NR^6R^7$, $-S(=O)_{n1}-R^8$ or $-NR^5-S(=O)_{n1}-R^8$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; $C(=O)NR^6R^7$; $-NR^5-C(=O)-NR^6R^7$; $-NR^5-C(=O)-R^5$; $-S(=O)_{n1}-R^8$; $-NR^5-S(=O)_{n1}-R^8$; $-S-CN$; $-NR^5-CN$; aryloxy; arylthio; arylcarbonyl; aryl$C_{1-4}$alkyl; aryl$C_{1-4}$alkyloxy; a 5-or 6-membered monocyclic heterocycle containing at least one heteroatom selected from O, S or N and said 5-or 6-membered monocyclic heterocycle optionally being substituted with at least one substituent selected from $R^9$; or

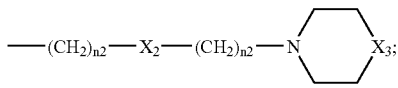

with n2 representing an integer with value 0, 1, 2, 3 or 4;
with $X_2$ representing O, $NR^5$ or a direct bond;
with $X_3$ representing O, $CH_2$, CHOH, $CH-N(R^5)_2$, $NR^5$ or $N-C(=O)-C_{1-4}$alkyl;

$R^3$ represents halo; hydroxy; $C_{1-6}$alkyl optionally substituted with at least one substituent selected from hydroxy, cyano, carboxyl, $C_{1-4}$alkyloxy, $C_{1-4}$alkyloxy-$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, $-C(=O)-NR^{6b}R^{7b}$, $-NR^5-C(=O)NR^{6b}R^{7b}$, $-S(=O)_{n1}-R^{8a}$ or $-NR^5-S(=O)_{n1}-R^{8a}$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, $-C(=O)-NR^{6b}R^{7b}$, $-NR^5-C(=O)-NR^{6b}R^{7b}$, $-S(=O)_{n1}-R^{8a}$ or $-NR^5-S(=O)_{n1}-R^{8a}$; polyhalo$C_{1-6}$alkyl optionally substituted with at least one substituent selected from hydroxy, cyano, carboxyl, $C_{1-4}$alkyloxy, $C_{1-4}$alkyloxy-$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, $-C(=O)-NR^{6b}R^{7b}$, $-NR^5-C(=O)-NR^{6b}R^{7b}$, $-S(=O)_{n1}-R^{8a}$ or $-NR^5-S(=O)_{n1}-R^{8a}$; $C_{1-6}$alkyloxy optionally substituted with one substituent selected from hydroxy, cyano, carboxyl, $C_{1-4}$alkyloxy, $C_{1-4}$alkylcarbonyl, $C_{1-4}$alkyloxy-carbonyl, $C_{1-4}$alkylcarbonyloxy, $NR^{6b}R^{7b}$, $-C(=O)-NR^{6b}R^{7b}$, $-NR^5-C(=O)-NR^{6b}R^{7b}$, $-S(=O)_{n1}-R^{8a}$ or $-NR^5-S(=O)_{n1}-R^{8a}$; polyhalo$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, $-C(=O)-NR^{6b}R^{7b}$, $-NR^5-C(=O)-NR^{6b}R^{7b}$, $-S(=O)_{n1}-R^{8a}$ or $-NR^5-S(=O)_{n1}-R^{8a}$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; aryloxy; arylthio; arylcarbonyl; $NR^{6b}R^{7b}$; $C(=O)-NR^{6b}R^{7b}$; $-NR^5-C(=O)-NR^{6b}R^{7b}$; $-NR^5-C(=O)-R^5$; $-S(=O)_{n1}-R^{8a}$; $-NR^5-S(=O)_{n1}-R^{8a}$; $-S-CN$; or $-NR^5-CN$;

$R^4$ represents hydrogen; halo; hydroxy; $C_{1-4}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, $-C(=O)-NR^{10}R^{11}$, $-NR^5-C(=O)-NR^{10}R^{11}$, $-S(=O)_{n1}-R^{12}$ or $-NR^5-S(=O)_{n1}-R^{12}$; $C_{2-4}$alkenyl or $C_{2-4}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, $-C(=O)-NR^{10}R^{11}$, $-NR^5-C(=O)-NR^{10}R^{11}$, $-S(=O)_{n1}-R^{12}$ or $-NR^5-S(=O)_{n1}-R^{12}$; polyhalo$C_{1-3}$alkyl; $C_{1-4}$alkyloxy optionally substituted with carboxyl; polyhalo$C_{1-3}$alkyloxy; $C_{1-4}$alkylthio; polyhalo$C_{1-3}$alkylthio; $C_{1-4}$alkyloxycarbonyl; $C_{1-4}$alkylcarbonyloxy; $C_{1-4}$alkylcarbonyl; polyhalo$C_{1-4}$alkylcarbonyl; nitro; cyano; carboxyl; $NR^{10}R^{11}$; $C(=O)NR^{10}R^{11}$; $-NR^5-C(=O)-NR^{10}R^{11}$; $-NR^5-C(=O)-R^5$; $-S(=O)_{n1}-R^{12}$; $-NR^5-S(=O)_{n1}-R^{12}$; $-S-CN$; or $-NR^5-CN$;

$R^5$ represents hydrogen; $C_{1-4}$alkyl or $C_{2-4}$alkenyl;

$R^6$ and $R^7$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkylcarbonyl; adamantanylcarbonyl; $C_{1-4}$alkyloxy$C_{1-4}$alkyl; $C_{1-4}$alkyl substituted with $C_{1-4}$alkyl-$NR^5-$; $C_{1-6}$alkyl optionally substituted with at least one substituent selected from halo, hydroxy, cyano, carboxyl, $C_{1-4}$alkyloxy, polyhalo$C_{1-4}$alkyl, $C_{1-4}$alkyloxy$C_{1-4}$alkyloxy, $NR^{6a}R^{7a}$, $C(=O)NR^{6a}R^{7a}$ or

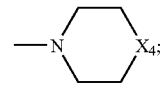

with
$X_4$ representing O, $CH_2$, CHOH, $CH-N(R^5)_2$, $NR^5$ or $N-C(=O)-C_{1-4}$alkyl;

$R^{6a}$ and $R^{7a}$ each independently represent hydrogen; $C_{1-4}$alkyl; $C_{1-4}$alkylcarbonyl or a 5- or 6-membered monocyclic heterocycle containing at least one heteroatom selected from O, S or N;

$R^{6b}$ and $R^{7b}$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkylcarbonyl; adamantanylcarbonyl; $C_{1-4}$alkyloxy$C_{1-4}$alkyl; $C_{1-4}$alkyl substituted with $C_{1-4}$alkyl-$NR^5-$; $C_{1-6}$alkyl optionally substituted with at least one substituent selected from halo, hydroxy, cyano, carboxyl, $C_{1-4}$alkyloxy, polyhalo$C_{1-4}$alkyl, $C_{1-4}$alkyloxy-$C_{1-4}$alkyloxy, $NR^{6c}R^{7c}$ or $C(=O)NR^{6c}R^{7c}$;

$R^{6c}$ and $R^{7c}$ each independently represent hydrogen; $C_{1-4}$alkyl or $C_{1-4}$alkylcarbonyl;

$R^8$ represents $C_{1-4}$alkyl optionally substituted with hydroxy; polyhalo$C_{1-4}$alkyl or $NR^6R^7$;

$R^{8a}$ represents $C_{1-4}$alkyl optionally substituted with hydroxy; polyhalo$C_{1-4}$alkyl or $NR^{6b}R^{7b}$;

$R^9$ represents halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)_{n1}-R^8$ or $-NR^5-S(=O)_{n1}-R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, $-C(=O)-NR^6R^7$, $-NR^5-C(=O)-NR^6R^7$, $-S(=O)_{n1}-R^8$ or $-NR^5-S(=O)_{n1}-R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; cyano; carboxyl; $NR^6R^7$; $C(=O)$ NR$^6$R$^7$; —NR$^5$—C(=O)—NR$^6$R$^7$; —NR$^5$—C(=O)—R$^5$; —S(=O)$_{n1}$—R$^8$; —NR$^5$—S(=O)$_{n1}$—R$^8$; —S—CN; or —NR$^5$—CN;

R$^{10}$ and R$^{11}$ each independently represent hydrogen; C$_{1-6}$alkyl; cyano; C$_{1-6}$alkylcarbonyl; C$_{1-4}$alkyloxyC$_{1-4}$alkyl; or C$_{1-4}$alkyl substituted with C$_{1-4}$alkyl-NR$^5$—;

R$^{12}$ represents C$_{1-4}$alkyl or NR$^{10}$R$^{11}$;

n1 represents an integer with value 1 or 2;

aryl represents phenyl or phenyl substituted with at least one substituent selected from halo, C$_{1-6}$alkyl, C$_{3-7}$cycloalkyl, C$_{1-6}$alkyloxy, cyano, nitro, polyhaloC$_{1-6}$alkyl or polyhaloC$_{1-6}$alkyloxy.

The present invention also relates to the use of a compound of formula (I) for the manufacture of a medicament for the prevention or the treatment of diseases mediated through GSK3.

DETAILED DESCRIPTION OF THE INVENTION

As used herein C$_{1-3}$alkyl as a group or part of a group defines straight or branched chain saturated hydrocarbon radicals having from 1 to 3 carbon atoms such as methyl, ethyl, propyl, 1-methylethyl; C$_{1-4}$alkyl as a group or part of a group defines straight or branched chain saturated hydrocarbon radicals having from 1 to 4 carbon atoms such as the groups defined for C$_{1-3}$alkyl and butyl; C$_{1-6}$alkyl as a group or part of a group defines straight or branched chain saturated hydrocarbon radicals having from 1 to 6 carbon atoms such as the groups defined for C$_{1-4}$alkyl and pentyl, hexyl, 2-methylbutyl and the like; C$_{2-4}$alkenyl as a group or part of a group defines straight and branched chain hydrocarbon radicals having from 2 to 4 carbon atoms containing a double bond such as ethenyl, propenyl, butenyl and the like; C$_{2-6}$alkenyl as a group or part of a group defines straight and branched chain hydrocarbon radicals having from 2 to 6 carbon atoms containing a double bond such as the groups defined for C$_{2-4}$alkenyl and pentenyl, hexenyl and the like; C$_{2-4}$alkynyl as a group or part of a group defines straight and branched chain hydrocarbon radicals having from 2 to 4 carbon atoms containing a triple bond such as ethynyl, propynyl, butynyl and the like; C$_{2-6}$alkynyl as a group or part of a group defines straight and branched chain hydrocarbon radicals having from 2 to 6 carbon atoms containing a triple bond such as the group defined for C$_{2-4}$alkynyl and pentynyl, hexynyl and the like; C$_{3-7}$cycloalkyl is generic to cyclo-propyl, cyclobutyl, cyclopentyl, cyclohexyl and cycloheptyl; a 4, 5, 6- or 7-membered monocyclic heterocycle containing at least one heteroatom selected from O, S or N comprises saturated, partially saturated or aromatic 4, 5, 6- or 7-membered monocyclic heterocycles containing at least one heteroatom selected from O, N or S; saturated heterocycles are heterocycles containing only single bonds; partially saturated heterocycles are heterocycles containing at least one double bond provided that the ring system is not an aromatic ring system; the term aromatic is well known to a person skilled in the art and designates cyclically conjugated systems of 4n'+2 electrons, that is with 6, 10, 14 etc. π-electrons (rule of Hückel; n' being 1, 2,3 etc.).

Particular examples of 4, 5, 6- or 7-membered saturated monocyclic heterocycles are azetidinyl, oxetanyl, tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyridazinyl, dioxanyl, morpholinyl, dithianyl, thiomorpholinyl, piperazinyl, homopiperidinyl (azepanyl), [1,3]diazepanyl, homopiperazinyl ([1,4]diazepanyl), [1,2]diazepanyl, oxepanyl, dioxepanyl.

Particular examples of 5- or 6-membered partially saturated heterocycles are pyrrolinyl, imidazolinyl, pyrazolinyl and the like.

Particular examples of 4, 5, 6- or 7-membered aromatic monocyclic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhaloC$_{1-4}$alkyl and polyhaloC$_{1-6}$alkyl as a group or part of a group are defined as mono- or polyhalosubstituted C$_{1-4}$alkyl or C$_{1-6}$alkyl, for example, methyl substituted with one or more fluoro atoms, for example, difluoromethyl or trifluoromethyl, 1,1-difluoro-ethyl and the like. In case more than one halogen atoms are attached to an alkyl group within the definition of polyhaloC$_{1-4}$alkyl or polyhaloC$_{1-6}$alkyl, they may be the same or different.

The term heterocycle as in the definition of for instance R$^2$ is meant to include all the possible isomeric forms of the heterocycles, for instance, pyrrolyl also includes 2H-pyrrolyl.

The hereinabove-mentioned heterocycles may be attached to the remainder of the molecule of formula (I) through any ring carbon or heteroatom as appropriate, if not otherwise specified. Thus, for example, when the 5- or 6-membered heterocycle is imidazolyl, it may be 1-imidazolyl, 2-imidazolyl, 4-imidazolyl and the like.

When any variable (eg. R$^6$, R$^7$ etc.) occurs more than one time in any constituent, each definition is independent.

Lines drawn into ring systems from substituents indicate that the bond may be attached to any of the suitable ring atoms of the ring system. For instance for a radical of formula (a-1), said radical may be attached to the remainder of the compound of formula (I) via a carbon atom of the phenyl moiety or via a carbon atom or heteroatom of the —B—C— moiety.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

Some of the compounds of formula (I) may also exist in their tautomeric form (e.g. keto-enol tautomerism). Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

A first interesting embodiment of the present invention are those compounds of formula (I) wherein ring A represents phenyl, pyridyl, pyrimidinyl, pyridazinyl or pyrazinyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;

X represents a direct bond; —$(CH_2)_{n3}$— or —$(CH_2)_{n4}$—$X_a$—$X_b$—;

with $n_3$ representing an integer with value 1, 2, 3 or 4;
with $n_4$ representing an integer with value 1 or 2;
with $X_a$ representing O or $NR^5$; and
with $X_b$ representing a direct bond or $C_{1-2}$alkyl;

$R^2$ represents $C_{3-7}$cycloalkyl; phenyl or a 4, 5, 6- or 7-membered monocyclic heterocycle containing at least one heteroatom selected from O, S or N; or a radical of formula

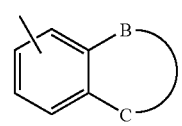

(a-1)

wherein —B—C— represents a bivalent radical of formula

—$CH_2$—$CH_2$—$CH_2$— (b-1);

—$CH_2$—$CH_2$—$CH_2$—$CH_2$— (b-2);

—$X_1$—$CH_2$—$CH_2$—$(CH_2)_n$— (b-3);

—$X_1$—$CH_2$—$(CH_2)_n$—$X_1$— (b-4);

—$X_1$—$(CH_2)_{n'}$—CH=CH— (b-5);

with $X_1$ representing O or $NR^5$;
n representing an integer with value 0, 1, 2 or 3;
n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; —$NR^5$—CN; aryloxy; arylthio; arylcarbonyl; aryl$C_{1-4}$alkyl; aryl$C_{1-4}$alkyloxy or a 5-or 6-membered monocyclic heterocycle containing at least one heteroatom selected from O, S or N and said 5-or 6-membered monocyclic het erocycle optionally being substituted with at least one substituent selected from $R^9$; or

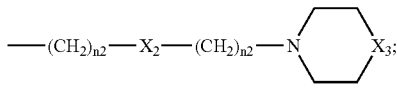

with n2 representing an integer with value 0, 1, 2, 3 or 4;
with $X_2$ representing O, $NR^5$ or a direct bond;
with $X_3$ representing O or $NR^5$;

$R^3$ represents halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; nitro; cyano; carboxyl; $NR^{6b}R^{7b}$; C(=O)$NR^{6b}R^{7b}$; —$NR^5$—C(=O)—$NR^{6b}R^{7b}$; —$NR^5$—C(=O)—$R^5$; —S(=O)$_{n1}$—$R^{8a}$; —$NR^5$—S(=O)$_{n1}$—$R^{8a}$; —S—CN; or —$NR^5$—CN;

$R^4$ represents hydrogen; halo; hydroxy; $C_{1-4}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, —C(=O)—$NR^{10}R^{11}$, —$NR^5$—C(=O)—$NR^{10}R^{11}$, —S(=O)$_{n1}$—$R^{12}$ or —$NR^5$—S(=O)$_{n1}$—$R^{12}$; $C_{2-4}$alkenyl or $C_{2-4}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, —C(=O)—$NR^{10}R^{11}$, —$NR^5$—C(=O)—$NR^{10}R^{11}$, —S(=O)$_{n1}$—$R^{12}$ or —$NR^5$—S(=O)$_{n1}$—$R^{12}$; polyhalo$C_{1-3}$alkyl; $C_{1-4}$alkyloxy optionally substituted with carboxyl; polyhalo$C_{1-3}$alkyloxy; $C_{1-4}$alkylthio; polyhalo$C_{1-3}$alkylthio; $C_{1-4}$alkyloxycarbonyl; $C_{1-4}$alkylcarbonyloxy; $C_{1-4}$alkylcarbonyl; polyhalo$C_{1-4}$alkylcarbonyl; nitro; cyano; carboxyl; $NR^{10}R^{11}$; C(=O)$NR^{10}R^{11}$; —$NR^5$—C(=O)—$NR^{10}R^{11}$; —$NR^5$—C(=O)—$R^5$; —S(=O)$_{n1}$—$R^{12}$; —$NR^5$—S(=O)$_{n1}$—$R^{12}$; —S—CN; or —$NR^5$—CN;

$R^5$ represents hydrogen or $C_{1-4}$alkyl;

$R^6$ and $R^7$ each independently represent hydrogen; cyano; $C_{1-6}$alkylcarbonyl; $C_{1-4}$alkyloxy$C_{1-4}$alkyl; $C_{1-4}$alkyl substituted with $C_{1-4}$alkyl—$NR^5$—; $C_{1-6}$alkyl optionally substituted with hydroxy, $C_{1-4}$alkyloxy, $C_{1-4}$alkyloxy$C_{1-4}$alkyloxy, $NR^{6a}R^{7a}$, C(=O)$NR^{6a}R^{7a}$ or

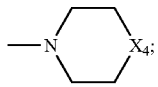

with $X_4$ representing O or $NR^5$;

$R^{6a}$ and $R^{7a}$ each independently represent hydrogen; $C_{1-4}$alkyl; $C_{1-4}$alkylcarbonyl or a 5- or 6-membered monocyclic heterocycle containing at least one heteroatom selected from O, S or N;

$R^{6b}$ and $R^{7b}$ each independently represent hydrogen; cyano; $C_{1-6}$alkylcarbonyl; $C_{1-4}$alkyloxy$C_{1-4}$alkyl; $C_{1-4}$alkyl substituted with $C_{1-4}$alkyl-$NR^5$—; $C_{1-6}$alkyl optionally substituted with hydroxy, $C_{1-4}$alkyloxy, $C_{1-4}$alkyloxy$C_{1-4}$alkyloxy, $NR^{6a}R^{7a}$ or C(=O)$NR^{6a}R^{7a}$;

$R^8$ represents $C_{1-4}$alkyl, polyhalo$C_{1-4}$alkyl or $NR^6R^7$;

$R^{8a}$ represents $C_{1-4}$alkyl, polyhalo$C_{1-4}$alkyl or $NR^{6b}R^{7b}$;

$R^9$ represents halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; or —$NR^5$—CN;

$R^{10}$ and $R^{11}$ each independently represent hydrogen; $C_{1-6}$alkyl; cyano; $C_{1-6}$alkylcarbonyl; $C_{1-4}$alkyloxy$C_{1-4}$alkyl; or $C_{1-4}$alkyl substituted with $C_{1-4}$alkyl-$NR^5$—;

$R^{12}$ represents $C_{1-4}$alkyl or $NR^{10}R^{11}$;

n1 represents an integer with value 1 or 2;

aryl represents phenyl or phenyl substituted with at least one substituent selected from halo, $C_{1-6}$alkyl, $C_{3-7}$cycloalkyl, $C_{1-6}$alkyloxy, cyano, nitro, polyhalo$C_{1-6}$alkyl or polyhalo$C_{1-6}$alkyloxy.

A second interesting embodiment of the present invention are those compounds of formula (I) wherein
ring A represents phenyl or pyridyl;
$R^1$ represents hydrogen;
X represents a direct bond or —(CH$_2$)$_{n3}$—;
$R^2$ represents phenyl or a radical of formula (b-4) wherein said $R^2$ may optionally be substituted with at least one substituent, in particular 1, 2 or 3 substituents, selected from halo; $C_{1-6}$alkyl optionally substituted with at least one substituent selected from hydroxy, cyano, carboxyl, $NR^6R^7$, C(=O)$NR^6R^7$, $C_{1-4}$alkyloxy or $C_{1-4}$alkyloxy-$C_{1-4}$alkyloxy; $C_{1-6}$alkyloxy; $C_{1-6}$alkyloxycarbonyl; $C_{1-4}$alkyloxy$C_{1-6}$alkyloxy; cyano; carboxyl; C(=O)$NR^6R^7$; —S(=O)$_{n1}$—$R^8$; aryl$C_{1-4}$alkyloxy; or a 5-or 6-membered heterocycle containing at least one heteroatom selected from O, S or N and said 5-or 6-membered heterocycle optionally being substituted with at least one substituent selected from $R^9$;

$R^3$ represents halo; hydroxy; $C_{1-6}$alkyl optionally substituted with at least one substituent selected from hydroxy, cyano, carboxyl, $C_{1-4}$alkyloxy, $NR^{6b}R^{7b}$ or C(=O)$NR^{6b}R^{7b}$; $C_{2-6}$alkenyl optionally substituted with at least one substituent selected from carboxyl or $C_{1-4}$alkyloxycarbonyl; polyhalo$C_{1-6}$alkyloxy; $C_{1-6}$alkyloxy optionally substituted with $C_{1-4}$alkyloxy or $NR^{6b}R^{7b}$; $C_{1-6}$alkylthio; $C_{1-6}$alkyloxycarbonyl; $C_{1-6}$alkylcarbonyl; cyano; carboxyl; $NR^{6b}R^{7b}$; C(=O)$NR^{6b}R^{7b}$; —$NR^5$—C(=O)—$R^5$; —S(=O)$_{n1}$—$R^{8a}$; —$NR^5$—S(=O)$_{n1}$—$R^{8a}$; or —S—CN;

$R^4$ represents hydrogen; halo; $C_{1-6}$alkyl; cyano; hydroxy; $C_{1-6}$alkyloxycarbonyl; $C_{1-6}$alkyloxy; carboxyl; or $NR^6R^7$.

A third interesting embodiment of the present invention are those compounds of formula (I) wherein
$R^5$ represents hydrogen or $C_{2-4}$alkenyl;
$R^6$, $R^7$, $R^{6b}$ and $R^{7b}$ each independently represent hydrogen; $C_{1-6}$alkylcarbonyl optionally substituted with $C_{1-4}$alkyloxy; $C_{1-6}$alkyloxycarbonyl; $C_{3-7}$cycloalkylcarbonyl; adamantanylcarbonyl; $C_{1-6}$alkyl optionally substituted with at least one substituent selected from halo, hydroxy, carboxyl, $C_{1-4}$alkyloxy, polyhalo$C_{1-4}$alkyl, $NR^{6a}R^{7a}$ respectively $NR^{6c}R^{7c}$, $C(=O)NR^{6a}R^{7a}$ respectively $C(=O)NR^{6c}R^{7c}$,
$R^8$ and $R^{8a}$ each independently represent $C_{1-4}$alkyl optionally substituted with hydroxy, or $NR^6R^7$ respectively $NR^{6b}R^{7b}$.

A fourth interesting embodiment are those compounds of formula (I) wherein the $R^3$ substituent is linked to ring A in metaposition compared to the $NR^1$ linker.

A fifth interesting embodiment are those compounds of formula (I) wherein the $R^3$ substituent is linked to ring A in paraposition compared to the $NR^1$ linker.

A sixth interesting embodiment of the present invention are those compounds of formula (I) wherein the $R^4$ substituent is linked to ring A in para position compared to the $NR^1$ linker.

A seventh interesting embodiment of the present invention are those compounds of formula (I) wherein the-X—$R^2$ substituent is unsubstituted or substituted with 1, 2 or 3 substituents, in particular the $R^2$ substituent is unsubstituted or substituted with 1 or 2 substituents, more in particular the-X—$R^2$ substituent is substituted with 1 substituent and preferably said substituent is placed in meta or para position, in particular in meta position, compared to the linkage of the-X—$R^2$ substituent with the nitrogen of the triazole moiety of the triazolepyrimidine ring.

An eighth interesting embodiment of the present invention are those compounds of formula (I) wherein $R^3$ represents $NR^{6b}R^{7b}$, more in particular monomethylamino ($NH(CH_3)$) or dimethylamino ($N(CH_3)_2$).

A ninth interesting embodiment of the present invention are those compounds of formula (I) wherein
ring A represents phenyl or pyridyl;
$R^1$ represents hydrogen;
X represents a direct bond;
$R^2$ represents phenyl wherein said $R^2$ may optionally be substituted with at least one substituent, in particular 1, 2 or 3 substituents, selected from halo; $C_{1-6}$alkyl substituted with one substituent selected from hydroxy, cyano, $NR^6R^7$, $C(=O)NR^6R^7$, $C_{1-4}$alkyloxy or $C_{1-4}$alkyloxy$C_{1-4}$alkyloxy; $C_{1-6}$alkyloxy; $C_{1-6}$alkyloxycarbonyl; $C_{1-4}$alkyloxy-$C_{1-6}$alkyloxy; $C(=O)NR^6R^7$; —$S(=O)_{n1}$—$R^8$; or a 5-or 6-membered heterocycle containing at least one heteroatom selected from O, S or N and said 5-or 6-membered heterocycle optionally being substituted with at least one substituent selected from $R^9$;
$R^3$ represents halo; hydroxy; $C_{1-6}$alkyl optionally substituted with at least one substituent selected from hydroxy, cyano, carboxyl, $C_{1-4}$alkyloxy, $NR^{6b}R^{7b}$ or $C(=O)NR^{6b}R^{7b}$; $C_{2-6}$alkenyl optionally substituted with at least one substituent selected from carboxyl, $C_{1-4}$alkyloxycarbonyl; polyhalo$C_{1-6}$alkyloxy; $C_{1-6}$alkyloxy optionally substituted with $C_{1-4}$alkyloxy; $C_{1-6}$alkylthio; $C_{1-6}$alkyloxycarbonyl; $C_{1-6}$alkylcarbonyl; cyano; carboxyl; $NR^{6b}R^{7b}$; $C(=O)NR^{6b}R^{7b}$; —$S(=O)_{n1}$—$R^8$; —$NR^5$—$C(=O)$—$R^5$; or —$NR^5$—$S(=O)_{n1}$—$R^8$;
$R^4$ represents hydrogen; halo; $C_{1-6}$alkyl; hydroxy; $C_{1-6}$alkyloxycarbonyl; $C_{1-6}$alkyloxy; carboxyl; or $NR^6R^7$.

A tenth interesting embodiment of the present invention are those compounds wherein
ring A represents phenyl;
$R^1$ represents hydrogen;
X represents a direct bond;
$R^2$ represents phenyl wherein said $R^2$ may optionally be substituted with at least one substituent, in particular 1 substituent, selected from halo; $C_{1-6}$alkyl substituted with one substituent selected from hydroxy, cyano, $NR^{6b}R^{7b}$ (in particular NH—C(=O)-cyclopropyl), $C(=O)NR^6R^7$ (in particular $C(=O)NH_2$), $C_{1-4}$alkyloxy or $C_{1-4}$alkyloxy-$C_{1-4}$alkyloxy; or —$S(=O)_{n1}$—$R^8$ (in particular $S(=O)_2$—$NH_2$);
$R^3$ represents halo; hydroxy; $C_{1-6}$alkyl substituted with hydroxy; $C_{1-6}$alkyloxy; $C_{1-6}$alkyloxycarbonyl; $C_{1-6}$alkylcarbonyl; cyano; carboxyl; $NR^{6b}R^{7b}$ (in particular $NH_2$); $C(=O)NR^{6b}R^{7b}$ (in particular $C(=O)NH_2$); —$S(=O)_{n1}$—$R^8$ (in particular —$S(=O)_2$—$CH_3$ or —$S(=O)_2$—$NH_2$); —$NR^5$—$S(=O)_{n1}$—$R^8$ (in particular —NH—$S(=O)_2$—$CH_3$); or —$NR^5$—$C(=O)$—$R^5$ (in particular —NH—C(=O)—$CH_3$);
$R^4$ represents hydrogen; halo; hydroxy; $C_{1-6}$alkyloxycarbonyl; $C_{1-6}$alkyloxy; carboxyl; or $NR^6R^7$ (in particular $NH_2$ or NH—C(=O)—$CH_3$).

An eleventh interesting embodiment of the present invention are those compounds of formula (I) wherein
ring A represents phenyl or pyridyl;
$R^1$ represents hydrogen;
X represents a direct bond;
$R^2$ represents phenyl wherein said $R^2$ is substituted with halo; $C_{1-6}$alkyl substituted with $NR^6R^7$; $C_{1-6}$alkyl substituted with hydroxy; $C_{1-6}$alkyl substituted with cyano; $C_{1-6}$alkyl substituted with $C_{1-4}$alkyloxy or $C_{1-6}$alkyl substituted with $C_{1-4}$alkyloxy$C_{1-4}$alkyloxy; $R^3$ represents halo; $C_{1-6}$alkyl substituted with hydroxy; $C_{1-6}$alkyl substituted with $NR^{6b}R^{7b}$; $C_{1-6}$alkyloxycarbonyl; cyano; carboxyl; $C(=O)NR^{6b}R^{7b}$; —$S(=O)_{n1}$—$R^{8a}$; or —$NR^5$—$S(=O)_{n1}$—$R^{8a}$;
$R^4$ represents hydrogen or $NR^6R^7$.

A twelfth interesting embodiment of the present invention are those compounds of formula (I) wherein X represents a direct bond.

A thirteenth interesting embodiment of the present invention are those compounds of formula (I) wherein $R^2$ represents phenyl; a 4, 5, 6- or 7-membered monocyclic heterocycle containing at least one heteroatom selected from O, S or N; benzoxazolyl or a radical of formula

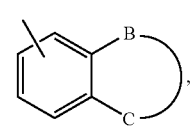

(a-1)

wherein said $R^2$ may optionally be substituted as defined hereinabove.

A fourteenth interesting embodiment of the present invention are those compounds of formula (I) wherein $R^2$.represents $C_{3-7}$cycloalkyl; phenyl; a 4, 5, 6- or 7-membered monocyclic heterocycle containing at least one heteroatom selected from O, S or N; benzoxazolyl or a radical of formula (a-1) wherein said $R^2$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; polyhalo$C_{1-6}$alkyl substituted with $NR^6R^7$;

$C_{1-6}$alkyloxy substituted with $NR^6R^7$; polyhalo$C_{1-6}$alkyloxy substituted with $NR^6R^7$; or $NR^6R^7$.

A fifteenth interesting embodiment of the present invention are those compounds of formula (I) wherein $R^3$ represents $C_{1-6}$alkyl substituted with $NR^{6b}R^{7b}$; $C_{2-6}$alkenyl or $C_{2-6}$alkynyl, each substituted with $NR^{6b}R^{7b}$; polyhalo$C_{1-6}$alkyl substituted with $NR^{6b}R^{7b}$; $C_{1-6}$alkyloxy substituted with $NR^{6b}R^{7b}$; polyhalo$C_{1-6}$alkyloxy substituted with $NR^{6b}R^{7b}$; or $NR^{6b}R^{7b}$.

A sixteenth interesting embodiment of the present invention are those compounds of formula (I) wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1) wherein said $R^2$ substituent is substituted with at least one substituent selected from $C_{1-6}$alkyl substituted with $NR^6R^7$; $C_{2-6}$alkenyl or $C_{2-6}$alkynyl, each substituted with $NR^6R^7$; polyhalo$C_{1-6}$alkyl substituted with $NR^6R^7$; $C_{1-6}$alkyloxy substituted with $NR^6R^7$; polyhalo$C_{1-6}$alkyloxy substituted with $NR^6R^7$; or $NR^6R^7$; and wherein $R^3$ represents $C_{1-6}$alkyl substituted with $NR^{6b}R^{7b}$; $C_{2-6}$alkenyl or $C_{2-6}$alkynyl, each substituted with $NR^{6b}R^{7b}$; polyhalo$C_{1-6}$alkyl substituted with $NR^{6b}R^{7b}$; $C_{1-6}$alkyloxy substituted with $NR^{6b}R^{7b}$; polyhalo$C_{1-6}$alkyloxy substituted with $NR^{6b}R^{7b}$; or $NR^{6b}R^{7b}$.

A seventeenth interesting embodiment of the present invention are those compounds of formula (I) wherein $R^1$ is hydrogen.

An eighteenth interesting embodiment of the present invention are those compounds of formula (I) wherein $R^2$ represents $C_{3-7}$cycloalkyl; phenyl; a 4, 5, 6- or 7-membered monocyclic heterocycle containing at least one heteroatom selected from O, S or N; benzoxazolyl or a radical of formula (a-1), wherein said $R^2$ substituent is substituted with at least one substituent selected from halo, in particular at least one fluoro atom; polyhalo$C_{1-6}$alkyl, in particular $C_{1-6}$alkyl substituted with one to three fluoro atoms, optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy, in particular $C_{1-6}$alkyloxy substituted with one to three fluoro atoms, optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$.

A nineteenth interesting embodiment of the present invention are those compounds of formula (I) wherein X—$R^2$ represents 3-fluorophenyl or 4-fluorophenyl.

Preferred compounds of formula (I) are compounds 29, 3, 1, 22, 6, 30, 31, 11, 34, 27, 36, 35, 43, 52, 54, 56, 45, 58, 63, 97, 98, 99, 103, 104, 109, 111, 124, 126, 133, 136, 139, 145, 152, 158, 167, 168, 171, 172, 173, 175, 201, 218, 248, 254, 255, 257, 261, 259, 260, 265, 266, 267, 270, 273, 275, 276, 277, 278, 268, 301, 304, 307, 311, 313, 329, 330, 336, 38, 2, 44, 62, 81, 84, 125, 134, 137, 138, 146, 169, 202, 256, 258, 264, 268, 269, 272, 274, 287 and 298, as listed in Table 1 hereinafter, their N-oxides, pharmaceutically acceptable addition salts, quaternary amines and stereochemically isomeric forms thereof.

More preferred compounds of formula (I) are compounds 38, 2, 44, 62, 81, 84, 125, 134, 137, 138, 146, 169, 202, 256, 258, 264, 268, 269, 272, 274, 287 and 298, as listed in Table 1 hereinafter, their N-oxides, pharmaceutically acceptable addition salts, quaternary amines and stereochemically isomeric forms thereof.

Most preferred compounds of formula (I) are compounds 32, 79, 101, 125, 146, 202, 214, 269, 285, 287, 293, 313, 316, 334, 339, 306 and 340 as listed in Table 1 hereinafter, their N-oxides, pharmaceutically acceptable addition salts, quaternary amines and stereochemically isomeric forms thereof.

Compounds of formula (I) can be prepared by cyclizing an intermediate of formula (II) in the presence of a nitrite salt, such as for example NaNO$_2$, a suitable acid, such as for example hydrochloric acid, e.g. HCl 6N or HCl 1N, and/or acetic acid and the like, and optionally in the presence of a suitable solvent, such as for example water.

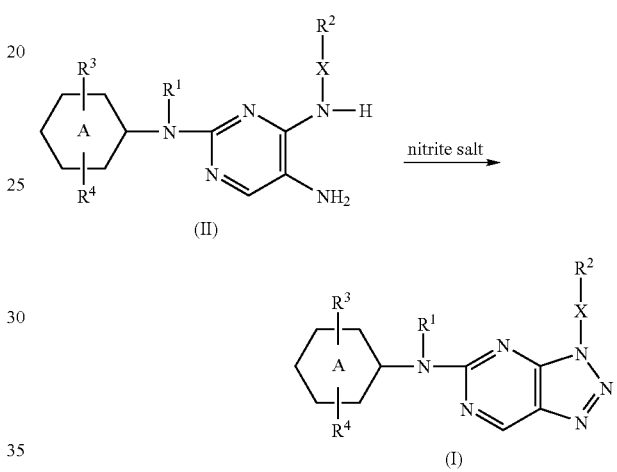

The above reaction can also be used to prepare compounds of formula (I) wherein $R^4$ represents either hydrogen or nitro, said compounds being represented by formula (I-a) and (I-b), from an intermediate of formula (II) wherein $R^4$ represents hydrogen, said intermediate being represented by formula (II-a).

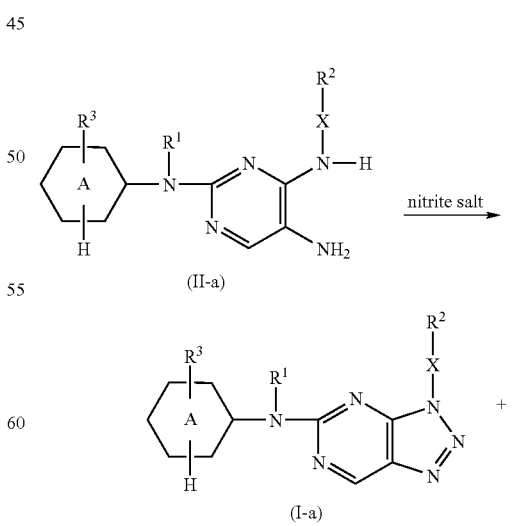

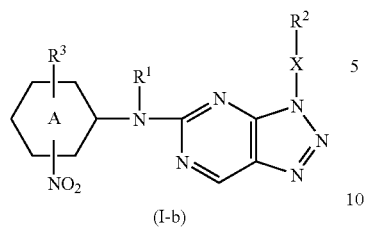

(I-b)

The above reaction can also be used to prepare a compound of formula (I) wherein $R^2$ represents a phenyl ring substituted with aminocarbonyl, said compound being represented by formula (I-c), from an intermediate of formula (II) wherein $R^2$ represents a phenyl ring substituted with an imidazole moiety, said intermediate being represented by formula (II-b).

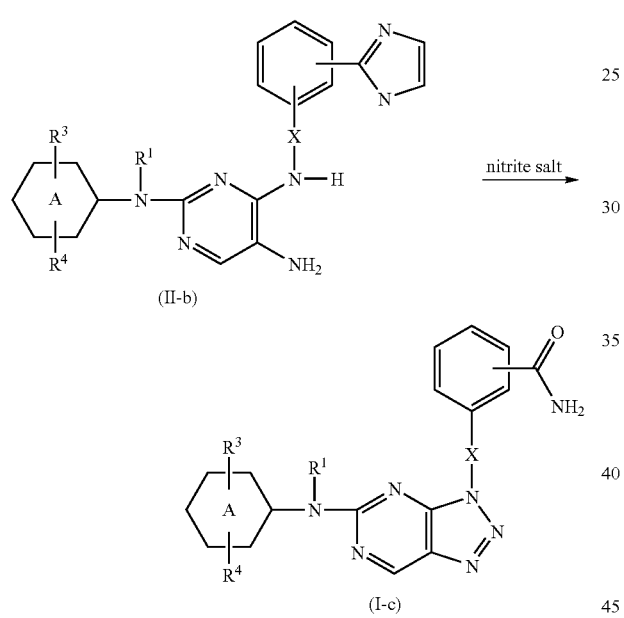

Compounds of formula (I) can also be prepared by reacting an intermediate of formula (III) with an intermediate of formula (IV) in the presence of a suitable solvent, such as for example $(CH_3)_2N—C(=O)H$, dimethylsulfoxide, $CH_3—O—CH_2—CH_2—OH$, an alcohol, e.g. 2-propanol and the like, optionally in the presence of a suitable base, such as for example N,N-diisopropylethanamine, NaH or 2,6-dimethylpyridine.

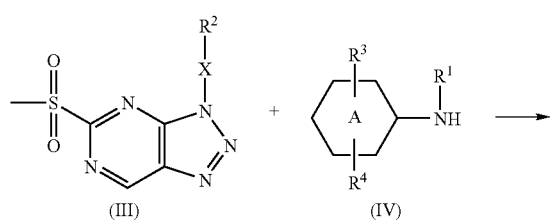

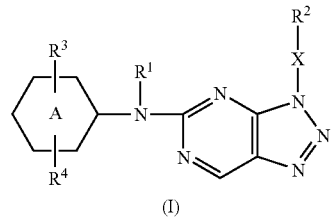

Compounds of formula (I) can also be prepared by reacting an intermediate of formula (III') with an intermediate of formula (IV) in the presence of a suitable solvent, such as for example $(CH_3)_2N—C(=O)H$, dimethylsulfoxide, $CH_3—O—CH_2—CH_2—OH$, an alcohol, e.g. 2-propanol and the like, optionally in the presence of a suitable base, such as for example N,N-diisopropylethanamine, NaH or 2,6-dimethylpyridine.

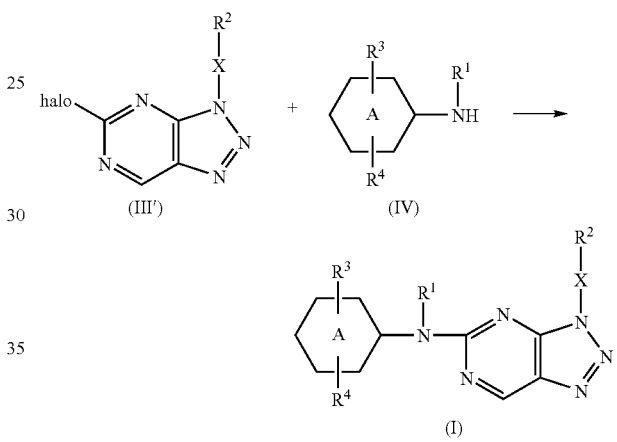

In the two above reactions, the obtained compound of formula (I) can be isolated, and, if necessary, purified according to methodologies generally known in the art such as, for example, extraction, crystallization, distillation, trituration and chromatography. In case the compound of formula (I) crystallizes out, it can be isolated by filtration. Otherwise, crystallization can be caused by the addition of an appropriate solvent, such as for example water; acetonitrile; an alcohol, such as for example methanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (I) can also be isolated by evaporation of the solvent followed by recrystallisation in an appropriate solvent, such as for example water; acetonitrile; an alcohol, such as for example methanol; and combinations of said solvents. The person skilled in the art will recognise which method should be used, which solvent is the most appropriate to use or it belongs to routine experimentation to find the most suitable isolation method.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^2$ is a ring system substituted with halo, e.g. bromo, can be converted into a compound of formula (I) wherein said $R^2$ substituent is unsubstituted, in the presence of $H_2$ and in the presence of a suitable catalyst, such as for example palladium on charcoal, a suitable catalyst poison, such as for example a thiophene solution, a suitable base, such as for example N,N-diethylethanamine, and a suitable solvent, such as for example tetrahydrofuran.

Compounds of formula (I) wherein $R^3$ is halo, e.g. bromo, can be converted into a compound wherein $R^3$ is cyano by reaction with Zn and $Zn(CN)_2$ in the presence of tris(dibenzylideneacetone)dipalladium, 1,1'-bis(diphenylphosphino)ferrocene and N,N-dimethylacetamide.

Compounds of formula (I) wherein $R^3$ is halo, e.g. bromo, can be converted into a compound wherein $R^3$ is $C_{2-6}$alkenyl optionally substituted with $C_{1-6}$alkyloxycarbonyl, by reaction with a $C_{2-6}$alkene optionally substituted with $C_{1-6}$alkyloxycarbonyl in the presence 1,3-bis(diphenylphosphino)propane, $Pd(OAc)_2$, a suitable base, such as for example N,N-diethylethanamine, and a suitable solvent, such as for example tetrahydrofuran.

Compounds of formula (I) wherein $R^3$ is $C_{1-6}$alkyl or $C_{2-6}$alkenyl both substituted with $C_{1-6}$alkyloxycarbonyl, can be converted into a compound of formula (I) wherein $R^3$ is $C_{1-6}$alkyl or $C_{2-6}$alkenyl both substituted with carboxyl by reaction with a suitable base, such as sodium hydroxide, in the presence of a suitable solvent, such as for example tetrahydrofuran.

Compounds of formula (I) wherein $R^3$ is —NH—C(=O)—$R^5$ can be converted into a compound of formula (I) wherein $R^3$ is $NH_2$ by reaction with a suitable acid, such as for example HCl, in the presence of a suitable solvent, such as for example an alcohol, e.g. ethanol and the like.

Compounds of formula (I) wherein $R^2$ is substituted with halo can also be converted into a compound of formula (I) wherein $R^2$ is substituted with $C_{1-6}$alkylthio, by reaction with a reagent of formula alkaline metal$^+$$^-$S—$C_{1-6}$alkyl, e.g. $Na^{+-}$S—$C_{1-6}$alkyl, in the presence of a suitable solvent, such as N,N-dimethylsulfoxide. The latter compounds can further be converted into a compound of formula (I) wherein $R^2$ is substituted with $C_{1-6}$alkyl-S(=O)—, by reaction with a suitable oxidizing agent, such as a peroxide, e.g. 3-chlorobenzenecarboperoxoic acid, in the presence of a suitable solvent, such as an alcohol, e.g. ethanol.

Compounds of formula (I) wherein $R^3$ is halo, or wherein $R^2$ is substituted with halo can also be converted into a compound of formula (I) wherein $R^3$ is $C_{1-6}$alkyloxy, or wherein $R^2$ is substituted with $C_{1-6}$alkyloxy, by reaction with an alcoholate salt, such as, for example, $LiOC_{1-6}$alkyl, in the presence of a suitable solvent, such as an alcohol, e.g. methanol.

Compounds of formula (I) wherein $R^3$ is halo, or wherein $R^2$ is substituted with halo can also be converted into a compound of formula (I) wherein $R^3$ is hydroxy, or wherein $R^2$ is substituted with hydroxy, by reaction with a suitable carboxylate, e.g. sodium acetate, in a suitable reaction-inert solvent, such as, for example, N,N-dimethylsulfoxide, followed by treating the obtained reaction product with a suitable base, such as pyridine.

Compounds of formula (I) wherein $R^3$ is chloro, or wherein $R^2$ is substituted with chloro, can be converted into a compound of formula (I) wherein $R^3$ is fluoro, or wherein $R^2$ is substituted with fluoro, by reaction with a suitable fluoride salt, such as for example potassium fluoride, in the presence of a suitable solvent, e.g. sulfolane.

Compounds of formula (I) wherein $R^3$ is $C_{1-4}$alkyloxy$C_{1-6}$alkyl or $R^2$ is substituted with $C_{1-4}$alkyloxy$C_{1-6}$alkyl, can be converted into a compound of formula (I) wherein $R^3$ is hydroxy$C_{1-6}$alkyl or $R^2$ is substituted with hydroxy$C_{1-6}$alkyl, by dealkylating the ether in the presence of a suitable dealkylating agent, such as, for example, tribromoborane, and a suitable solvent, such as methylene chloride.

Compounds of formula (I) wherein $R^3$ is $C_{1-6}$alkyloxycarbonyl, or wherein $R^2$ is substituted with $C_{1-6}$alkyloxycarbonyl, can be converted into a compound of formula (I) wherein $R^3$ is aminocarbonyl, or wherein $R^3$ is substituted with aminocarbonyl or mono- or di($C_{1-6}$alkyl)aminocarbonyl by reaction with a suitable agent such as ammonia, $NH_2(C_{1-6}$alkyl), $AlCH_3[N(C_{1-6}$alkyl$)_2]Cl$ optionally in the presence of a suitable acid, such as for example hydrochloric acid, and in the presence of a suitable solvent such as an alcohol, e.g. methanol; tetrahydrofuran; N,N-diisopropylethane.

Compounds of formula (I) wherein $R^3$ is $C_{1-6}$alkyloxycarbonyl, or wherein $R^2$ is substituted with $C_{1-6}$alkyloxycarbonyl, can also be converted into a compound of formula (I) wherein $R^3$ is carboxyl, or wherein $R^2$ is substituted with carboxyl, by reaction with a suitable base, such as for example sodium hydroxide, in the presence of a suitable solvent, such as for example dioxane or N,N-dimethylsulfoxide.

Compounds of formula (I) wherein $R^2$ is unsubstituted can be converted into a compound wherein $R^2$ is substituted with halo, by reaction with a suitable halogenating agent, such as, for example $Br_2$ or 1-(chloromethyl)-4-fluoro-1,4-diazoniabicyclo[2,2,2]octane bis[tetrafluoroborate], in the presence of a suitable solvent, such as tetrahydrofuran, water, acetonitrile, chloroform and optionally in the presence of a suitable base such as N,N-diethylethanamine.

Compounds of formula (I) wherein $R^3$ is $C_{1-6}$alkyloxycarbonyl or wherein $R^2$ is substituted with $C_{1-6}$alkyloxycarbonyl, can be converted into a compound of formula (I) wherein $R^3$ is hydroxymethyl or wherein $R^2$ is substituted with hydroxymethyl by reaction with a suitable reducing agent, such as for example $LiAlH_4$.

Compounds of formula (I) wherein $R^3$ is nitro, may be converted into a compound of formula (I) wherein $R^3$ is amino, by reaction with a suitable reducing agent, such as for example $H_2$, in the presence of a suitable catalyst, such as for example palladium on charcoal, a suitable catalyst poison, such as for example a thiophene solution, and a suitable solvent, such as for example an alcohol, e.g. methanol, ethanol and the like.

Compounds of formula (I) wherein $R^2$ is substituted with $NH_2$ can be converted into a compound of formula (I) wherein $R^2$ is substituted with NH—S(=O)$_2$—$NR^6R^7$ by reaction with $W_1$—S(=O)$_2$—$NR^6R^7$ wherein $W_1$ represents a suitable leaving group such as for example a halo atom, e.g. chloro, in the presence of a suitable solvent, such as for example N,N-dimethylacetamide and a suitable base, such as for example N,N-diethylethanamine.

Compounds of formula (I) wherein $R^3$ is NH—C(=O)—$C_{1-6}$alkyl, NH—C(=O)—O—$C_{1-6}$alkyl, $C_{1-6}$alkyl substituted with NH—C(=O)—$C_{1-6}$alkyl or with NH—C(=O)—O—$C_{1-6}$alkyl, or wherein $R^2$ is substituted with NH—C(=O)—$C_{1-6}$alkyl, NH—C(=O)—O—$C_{1-6}$alkyl, $C_{1-6}$alkyl substituted with NH—C(=O)—$C_{1-6}$alkyl or with NH—C(=O)—O—$C_{1-6}$alkyl, can be converted into a compound of formula (I) wherein $R^3$ represents $NH_2$ or $C_{1-6}$alkyl substituted with $NH_2$, or wherein $R^2$ is substituted with $NH_2$ or $C_{1-6}$alkyl substituted with $NH_2$, by reaction with a suitable acid, such as for example HCl, in the presence of a suitable solvent, such as for example dioxane or an alcohol, e.g. ethanol, methoxyethanol, 2-propanol.

Compounds of formula (I) wherein $R^3$ is NH—S(=O)$_{n1}$—$R^8$ or wherein $R^2$ is substituted with NH—S(=O)$_{n1}$—$R^8$, can be converted into a compound of formula (I) wherein $R^3$ is N($C_{2-4}$alkenyl)—S(=O)$_{n1}$—$R^8$ or wherein $R^2$ is substituted with N($C_{2-4}$alkenyl)—S(=O)$_{n1}$—$R^8$, by reaction with $C_{2-4}$alkenyl-$W_1$, wherein $W_1$ represents a suitable leaving group, such as for example halo, e.g. bromo and the like, in the presence of NaH and a suitable solvent, such as for example N,N-dimethylformamide.

Compounds of formula (I) wherein $R^3$ represents $NH_2$ or $C_{1-6}$alkyl substituted with $NH_2$, or wherein $R^2$ is substituted with $NH_2$ or $C_{1-6}$alkyl substituted with $NH_2$, can be converted into a compound of formula (I) wherein $R^3$ represents $N(CH_3)_2$ or $C_{1-6}$alkyl substituted with $N(CH_3)_2$, or wherein $R^2$ is substituted with $N(CH_3)_2$ or $C_{1-6}$alkyl substituted with $N(CH_3)_2$, by reductive alkylation with [—O—$CH_2$—]$_n$ in the presence of $H_2$, a suitable catalyst, such as for example palladium on charcoal, a suitable catalyst poison, such as for example a thiophene solution, and a suitable solvent, such as for example an alcohol, e.g. methanol.

Compounds of formula (I) wherein $R^1$ is hydrogen, can be converted into a compound of formula (I) wherein $R^1$ is ethyl by reaction with N,N-diethylethanamine in the presence of a suitable solvent, such as for example N,N-dimethylformamide.

Compounds of formula (I) wherein $R^3$ is C(=O)—$C_{1-6}$alkyl, can be converted into a compound of formula (I) wherein $R^3$ is C(=O)—$N(CH_3)_2$, by reaction with N,N-dimethylformamide.

Compounds of formula (I) wherein $R^2$ is substituted with C(=O)—$C_{1-6}$alkyl, can be converted into a compound of formula (I) wherein $R^2$ is substituted with C(=O)—$N(CH_3)_2$, by reaction with N,N-dimethylformamide.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures.

Intermediates of formula (II) can be prepared by reducing an intermediate of formula (V) with a suitable reducing agent, such as for example $H_2$, in the presence of a suitable catalyst, such as for example platina on charcoal or palladium on charcoal, optionally in the presence of a suitable catalyst poison, such as for example a thiophene solution, optionally in the presence of $NH_2$—$NH_2$, in the presence of a suitable solvent, such as for example N,N-dimethylacetamide, tetrahydrofuran, N,N-dimethylformamide or a suitable alcohol, such as for example methanol, ethanol and the like, and optionally in the presence of a suitable base, such as for example N,N-diethylethanamine.

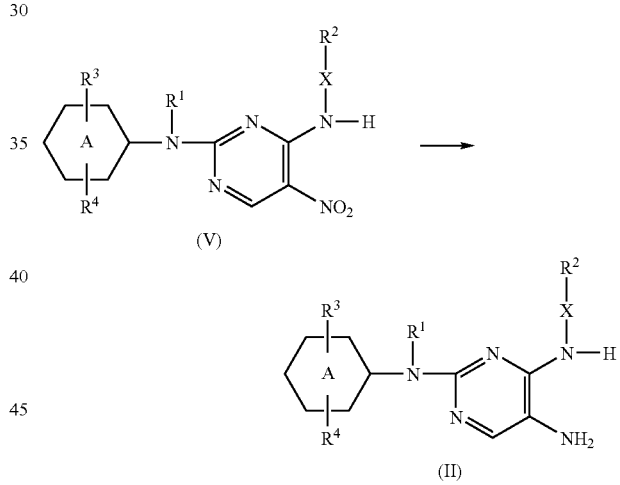

Intermediates of formula (V) can be prepared by reacting an intermediate of formula (VI) wherein $W_1$ represents a suitable leaving group, such as for example halogen, e.g. chloro and the like, with an intermediate of formula (VII) in the presence of a suitable solvent, such as for example N,N-dimethylacetamide or an alcohol, e.g. ethanol and the like, and optionally in the presence of a suitable base, such as for example N,N-diisopropylethanamine.

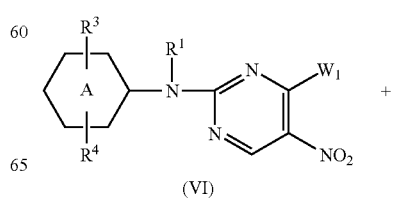

-continued

R²—X—NH₂
(VII)

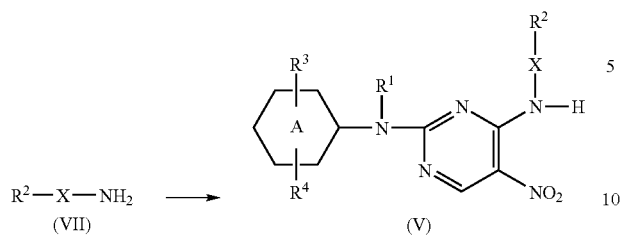
(V)

Intermediates of formula (V) can also be prepared by reacting an intermediate of formula (VIII) wherein $W_2$ represents a suitable leaving group, such as for example halogen, e.g. chloro and the like, with an intermediate of formula (IV) in the presence of a suitable base, such as for example N,N-diisopropylethanamine or N,N-diethylethanamine, and optionally in the presence of a suitable solvent, such as for example N,N-dimethylacetamide, N,N-dimethylformamide, 1,4-dioxane.

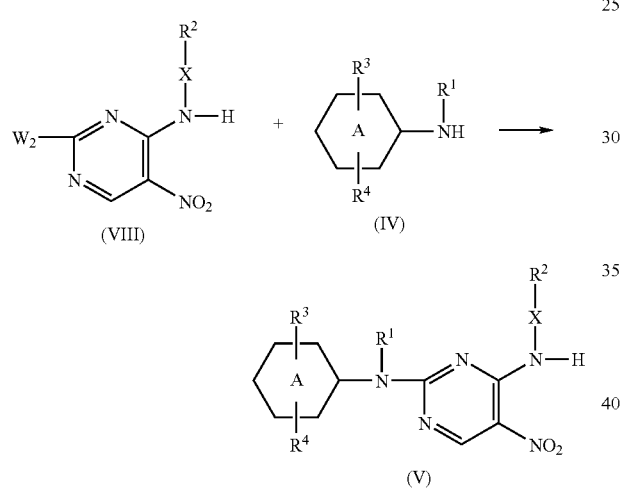
(VIII)   (IV)

(V)

Intermediates of formula (V) wherein R²—X—NH— and the

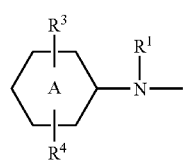

moiety represent the same substituent being represented by Rᵃ—NH—, said intermediates being represented by formula (V-a), can be prepared by reacting an intermediate of formula (IX) wherein $W_2$ is defined as herein above, with Rᵃ—NH₂ in the presence of a suitable base, such as for example N,N-diisopropylethanamine, and a suitable solvent, such as for example N,N-dimethyl-acetamide, N,N-dimethylformamide or $CH_2Cl_2$.

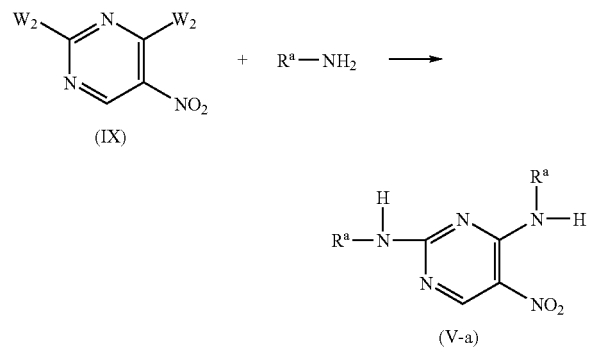
(IX)

(V-a)

Intermediates of formula (V) can also be prepared by reacting an intermediate of formula (IV) with an intermediate of formula (VII) and an intermediate of formula (IX) in the presence of a suitable solvent, such as for example N,N-dimethylformamide.

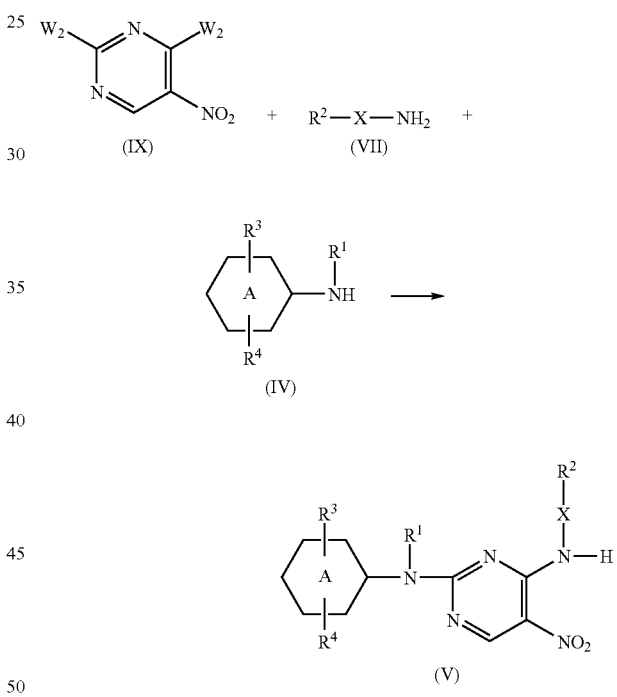
(IX)   (VII)

(IV)

(V)

Intermediates of formula (VI) wherein $W_1$ represents chloro, said intermediates being represented by formula (VI-a), can be prepared by reacting an intermediate of formula (X) with $POCl_3$.

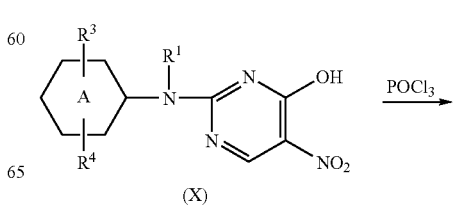
(X)

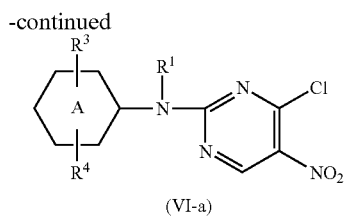

(VI-a)

Intermediates of formula (X) can be prepared by reacting an intermediate of formula (IV) with an intermediate of formula (XI) wherein $W_3$ represents a suitable leaving group, such as for example halogen, e.g. chloro, in the presence of a suitable solvent, such as for example tetrahydrofuran and water, or $CH_3$—O—$(CH_2)_2$—OH, and optionally in the presence of a suitable base, such as for example N,N-diisopropylethanamine.

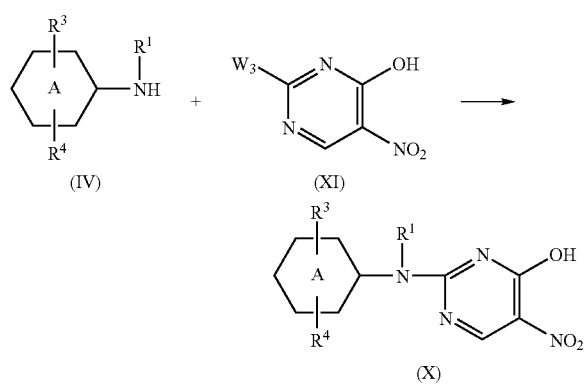

Intermediates of formula (IV) wherein $R^1$ represents hydrogen, said intermediates being represented by formula (IV-a), can be prepared by reacting an intermediate of formula (IV-b) with a suitable reducing agent, such as for example $H_2$, in the presence of a suitable catalyst, such as for example platina on charcoal or palladium on charcoal, optionally a suitable catalyst poison, such as for example a thiophene solution, a suitable solvent, such as for example N,N-dimethylacetamide, tetrahydrofuran, N,N-dimethylformamide or a suitable alcohol, such as for example methanol, and optionally in the presence of a suitable base, such as for example N,N-diethylethanamine.

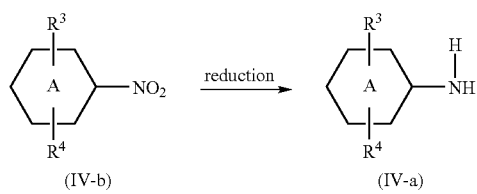

Intermediates of formula (IV-b) wherein $R^3$ represents $C(=O)NR^{6b}R^{7b}$, said intermediates being represented by formula (IV-b-1), can be prepared by reacting an intermediate of formula (IV-c) wherein $W_4$ represents a suitable leaving group, such as for example halo, e.g. chloro and the like, with an intermediate of formula (XV), in the presence of a suitable solvent, such as for example aceton and the like.

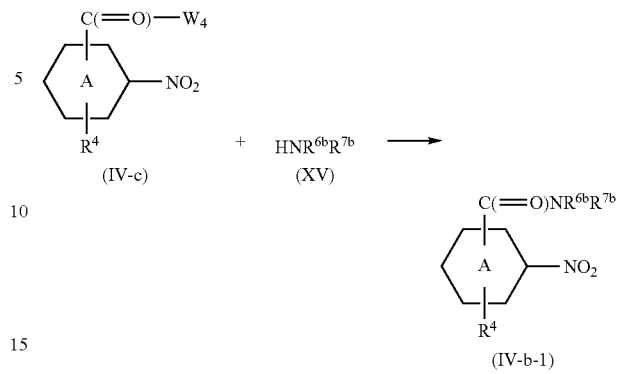

Intermediates of formula (IV-b) wherein $R^3$ represents $C_{1-6}$alkyl substituted with $NR^{6b}R^{7b}$ wherein $R^{6b}$ represents $C_{1-6}$alkyloxycarbonyl, said intermediates being represented by formula (IV-b-2), can be prepared by reacting an intermediate of formula (XVI) with an intermediate of formula (XVII) in the presence of a suitable base, such as for example 4-N,N-dimethylamine-pyridine, in the presence of a suitable solvent, such as for example methylenechloride.

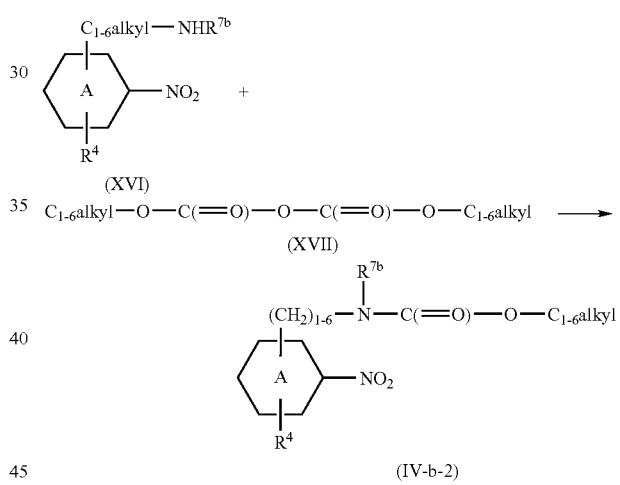

Intermediates of formula (IV-b) wherein $R^3$ represents —$CH_2$—NH-optionally substituted $C_{1-6}$alkyl (—$CH_2$—NH-(substituted)$C_{1-6}$alkyl), said intermediates being represented by formula (IV-b-3), can be prepared by reacting an intermediate of formula (XVIII) with an intermediate of formula (XIX) in the presence of a suitable reducing agent, such as for example $NaBH(OAc)_3$, a suitable acid, such as for example acetic acid, and a suitable solvent, such as for example methylene chloride.

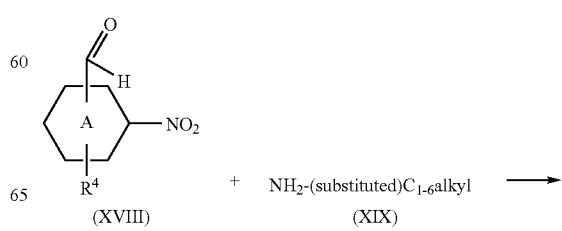

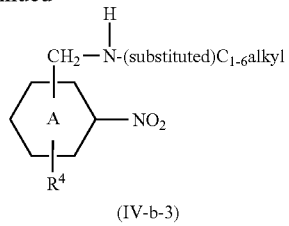

(IV-b-3)

Intermediates of formula (VIII) can be prepared by reacting an intermediate of formula (VII) with an intermediate of formula (IX) in the presence of a suitable solvent, such as for example N,N-dimethylacetamide, N,N-dimethylformamide, $CH_2Cl_2$ or 1,4-dioxane, and optionally in the presence of a suitable base, such as for example N,N-diisopropylethanamine.

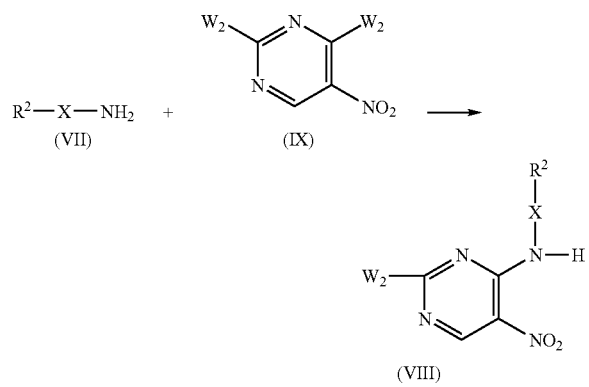

Intermediates of formula (VII) can be prepared by reducing an intermediate of formula (VII-a) in the presence of Fe and an ammonium chloride solution.

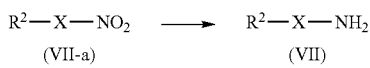

Intermediates of formula (III) can be prepared by reacting an intermediate of formula (XII) with a suitable oxidizing agent, such as for example $KMnO_4$, in the presence of a suitable solvent, such as for example water, and a suitable acid, such as for example acetic acid. An alternative suitable oxidizing agent is meta-chloroperbenzoic acid, in a suitable solvent, such as for example $CH_2Cl_2$, optionally in the presence of morpholinomethyl polystyrene HL resin and (polystyrylmethyl)trimethylammonium bicarbonate resin.

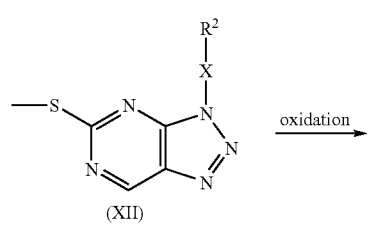

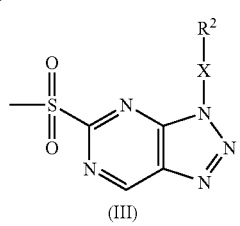

(III)

Intermediates of formula (III) wherein $R^2$ is substituted with $C_{1-6}$alkyl substituted with $NR^6H$, said intermediates being represented by formula (III-a), can be prepared by reacting an intermediate of formula (XII) wherein $R^2$ is substituted with $C_{1-6}$alkyl substituted with $NH_2$, said intermediate being represented by formula (XII-a),with an intermediate of formula (XXII) wherein $W_5$ represents a suitable leaving group, such as for example halo, e.g. chloro, in the presence of a suitable oxidizing agent such as for example meta-chloroperbenzoic acid, a suitable solvent, such as for example $CH_2Cl_2$ and an alcohol, e.g. methanol and the like, optionally in the presence of morpholinomethyl polystyrene HL resin and (polystyrylmethyl)trimethylammonium bicarbonate resin.

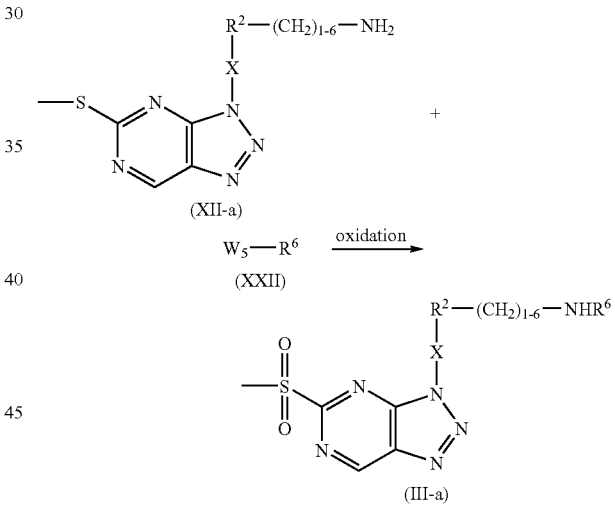

Intermediates of formula (XII) can be prepared by reacting an intermediate of formula (XIII) with a nitrite salt, such as for example $NaNO_2$, a suitable solvent, such as for example water, and a suitable acid, such as for example hydrochloric acid 6N or 1N and/or acetic acid and the like.

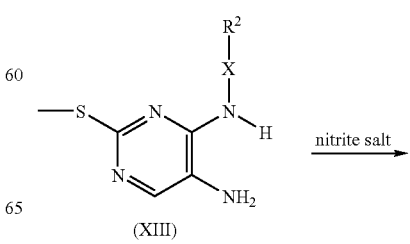

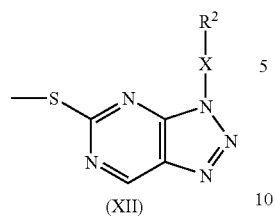

(XII)

Intermediates of formula (XII-a) can be prepared by reacting an intermediate of formula (XII-b) with a suitable acid, such as for example HCl and the like, in the presence of a suitable solvent, such as for example water.

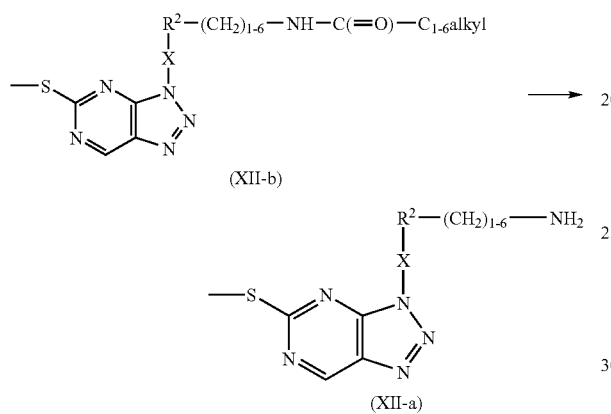

Intermediates of formula (XIII) can be prepared by reacting an intermediate of formula (XIV) with a suitable reducing agent, such as for example $H_2$, in the presence of a suitable catalyst, such as for example platina on charcoal or palladium on charcoal, optionally a suitable catalyst poison, such as for example a thiophene solution, a suitable solvent, such as for example N,N-dimethylacetamide, tetrahydrofuran, N,N-dimethylformamide or a suitable alcohol, such as for example methanol, and optionally in the presence of a suitable base, such as for example N,N-diethylethanamine.

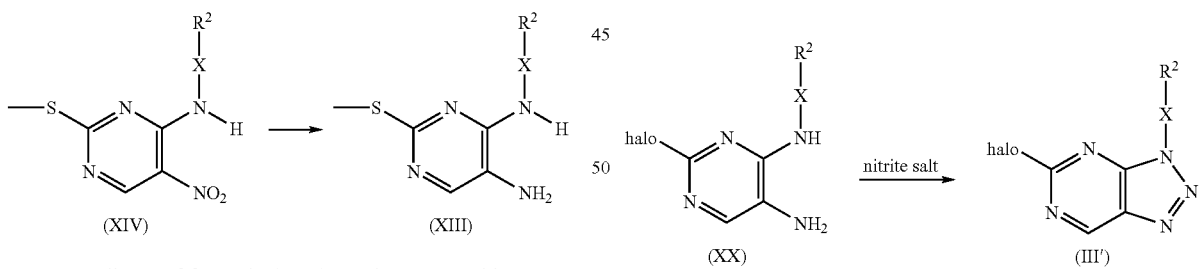

Intermediates of formula (XIV) can be prepared by reacting an intermediate of formula (VIII), in the presence of NaS—$CH_3$ in water.

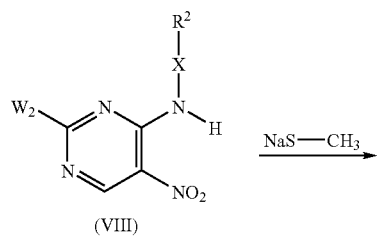

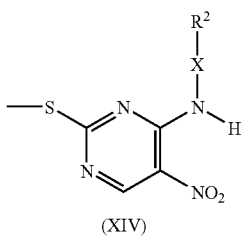

(XIV)

Intermediates of formula (XIV) can also be prepared by reacting an intermediate of formula (IX) with an intermediate of formula (VII) in the presence of $NaCH_2SH$ and a suitable solvent, such as for example N,N-dimethylformamide.

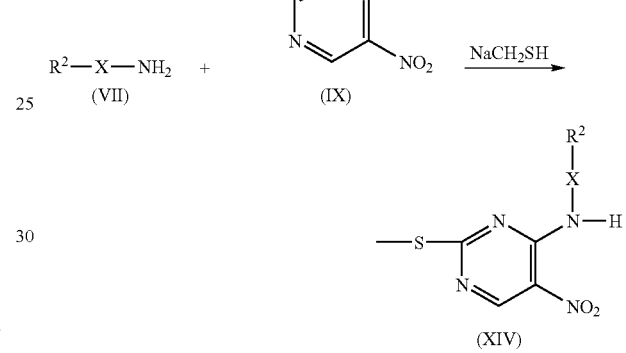

(XIV)

Intermediates of formula (III') can be prepared by cyclizing an intermediate of formula (XX) in the presence of a nitrite salt, such as for example $NaNO_2$, a suitable acid, such as for example hydrochloric acid, e.g. HCl 6N or HCl 1N, and/or acetic acid and the like, and optionally in the presence of a suitable solvent, such as for example water.

Intermediates of formula (XX) can be prepared by reducing an intermediate of formula (XXI) with a suitable reducing agent, such as for example $H_2$, in the presence of a suitable catalyst, such as for example platina on charcoal, in the presence of a suitable catalyst poison, such as for example a thiophene solution, in the presence of a suitable solvent, such as for example N,N-dimethylacetamide, tetrahydrofuran, N,N-dimethylformamide or a suitable alcohol, such as for example methanol, ethanol and the like, and in the presence of a suitable base, such as for example N,N-diethylethanamine.

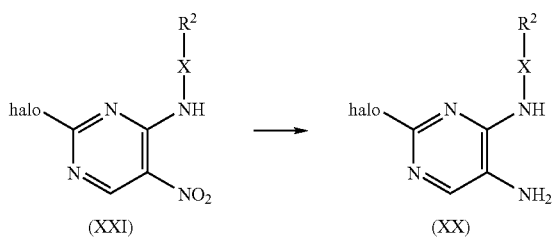

Intermediates of formula (XXI) can be prepared by reacting an intermediate of formula (VII) with an intermediate of formula (IX) wherein $W_2$ represents halo, said intermediate being represented by formula (IX-a), in the presence of a suitable solvent, such as for example methylene chloride, and a suitable base, such as for example N,N-dimethylbenzenamine.

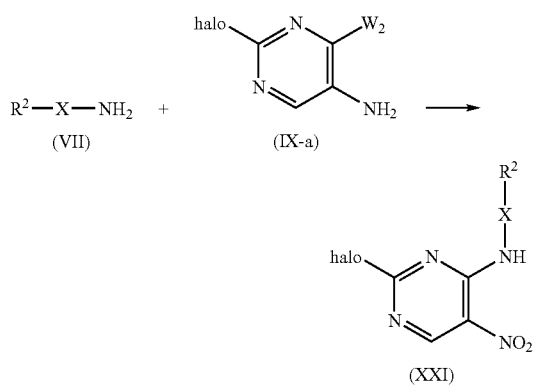

The compounds of formula (I) inhibit Glycogen synthase kinase 3 (GSK3), in particular glycogen synthase kinase 3 alpha (GSK3α) and/or glycogen synthase kinase 3 beta (GSK3β). They are selective Glycogen synthase kinase 3 inhibitors. Specific inhibitory compounds are superior therapeutic agents since they are characterized by a greater efficacy and lower toxicity by virtue of their specificity. Synonyms for GSK3 are tau protein kinase I (TPK I), FA (Factor A) kinase, kinase FA and ATP-citrate lysase kinase (ACLK).

Glycogen synthase kinase 3 (GSK3), which exists in two isoforms as already stated above, i.e. GSK3α and GSK3β, is a proline-directed serine/threonine kinase originally identified as an enzyme that phosphorylates glycogen synthase. However, it has been demonstrated that GSK3 phosphorylates numerous proteins in vitro such as glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-Myc transcription factor, adenomatous polyposis coli tumor supressor protein, tau protein and β-catenin.

The above-indicated diversity of proteins which may be phosphorylated by GSK3 implies that GSK3 is implicated in numerous metabolic and regulatory processes in cells.

GSK3 inhibitors may therefore be useful in the prevention or treatment of diseases mediated through GSK3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives. In particular, the compounds of the present invention are useful in the prevention or treatment of Alzheimer's disease; diabetes, in particular type 2 diabetes (non insulin dependent diabetes); bipolar disorder; cancer; pain, in particular neuropathic pain; depression; inflammatory diseases. More in particular, the compounds of the present invention are useful in the prevention or treatment of diabetes, in particular type 2 diabetes (non insulin dependent diabetes); pain, in particular neuropathic pain; depression; inflammatory diseases.

The major neuropathological landmarks in Alzheimer's disease are neuronal loss, the deposition of amyloid fibers and paired helical filaments (PHF) or neurofibrillary tangles (NFT). Tangle formation appears to be the consequence of accumulation of aberrantly phosphorylated tau protein. This aberrant phosphorylation destabilizes neuronal cytoskeleton, which leads to reduced axonal transport, deficient functioning and ultimately neuronal death. The density of neurofibrillary tangles has been shown to parallel duration and severity of Alzheimer's disease. Reduction of the degree of tau phosphorylation can provide for neuroprotection and can prevent or treat Alzheimer's disease or can slow the progression of the disease. As mentioned hereinabove, GSK3 phosphorylates tau protein. Thus compounds having an inhibitory activity for GSK3 may be useful for the prevention or the treatment of Alzheimer's disease.

Insulin regulates the synthesis of the storage polysaccharide glycogen. The rate-limiting step in the glycogen synthesis is catalyzed by the enzyme glycogen synthase. It is believed that glycogen synthase is inhibited by phosphorylation and that insulin stimulates glycogen synthase by causing a net decrease in the phosphorylation of this enzyme. Thus, in order to activate glycogen synthase, insulin must either activate phosphatases or inhibit kinases, or both.

It is believed that glycogen synthase is a substrate for glycogen synthase kinase 3 and that insulin inactivates GSK3 thereby promoting the dephosphorylation of glycogen synthase.

In addition to the role of GSK3 in insulin-induced glycogen synthesis, GSK3 may also play a role in insulin resistance. It is believed that GSK3 dependent Insulin Receptor Substrate-1 phosphorylation contributes to insulin resistance.

Therefore, GSK3 inhibition may result in the increased deposition of glycogen and a concomitant reduction of blood glucose, thus mimicing the hypoglycemic effect of insulin. GSK3 inhibition provides an alternative therapy to manage insulin resistance commonly observed in non insulin dependent diabetes mellitus and obesity. GSK3 inhibitors may thus provide a novel modality for the treatment of type 1 and type 2 diabetes.

GSK3 inhibitors may also be indicated for use in the prevention or the treatment of pain, in particular neuropathic pain.

After axotomy or chronic constriction injury, neuronal cells die through an apoptotic pathway and the morphological changes correlate with the onset of hyperalgesia and/or allodynia.

The induction of apoptosis is probably triggered by a reduced supply of neurotrophic factors as the time course of neuronal loss is positively altered by administration of neurotrophins. GSK has been shown to be involved in the initiation of the apoptotic cascade and trophic factor withdrawal stimulates the GSK3 apoptosis pathway. In view of the above, GSK3 inhibitors might reduce signals of and even prevent levels of neuropathic pain.

Due to their GSK3 inhibitory properties, the compounds of formula (I), their N-oxides, pharmaceutically acceptable addition salts, quaternary amines and stereochemically isomeric forms thereof, are useful to prevent or treat GSK3 mediated diseases, such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) ( late complication of viral infections in the central nervous system), inflammatory diseases, depression, cancer, dermatological disorders such as baldness, neuroprotection, schizophrenia, pain, in particular neuropathic pain. The present compounds are also useful as male contraceptives. In general, the compounds of the present invention may be useful in the treatment of warm-blooded animals suffering from a disease mediated through GSK3, or they may be useful to prevent warm-blooded animals to suffer from disease mediated through GSK3. More in particular, the compounds of the present invention may be useful in the treatment of warm-blooded animals suffering from Alzheimer's disease; diabetes, in particular type 2 diabetes; cancer; inflammatory diseases; bipolar disorder; depression; pain, in particular neuropathic pain. Even more in particular, the compounds of the present invention may be useful in the treatment of warm-blooded animals suffering from diabetes, in particular type 2 diabetes; inflammatory diseases; depression; pain, in particular neuropathic pain.

In view of the above described pharmacological properties, the compounds of formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through GSK3. More in. particular, the present. compounds can be used for the manufacture of a medicament for treating or preventing Alzheimer's disease; diabetes, in particular type 2 diabetes; cancer; inflammatory diseases; bipolar disorder; depression; pain, in particular neuropathic pain. Even more in particular, the present compounds can be used for the manufacture of a medicament for treating or preventing diabetes, in particular type 2 diabetes; inflammatory diseases; depression; pain, in particular neuropathic pain.

In view of the utility of the compounds of formula (I), there is provided a method of treating warm-blooded animals, including humans, suffering from or a method of preventing warm-blooded animals, including humans, to suffer from diseases mediated through GSK3, more in particular a method of treating or preventing Alzheimer's disease; diabetes, in particular type 2 diabetes; cancer; inflammatory diseases; bipolar disorder; depression; pain, in particular neuropathic pain, even more in particular diabetes, in particular type 2 diabetes; inflammatory diseases; depression; pain, in particular neuropathic pain. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for preventing or treating diseases mediated through GSK3, comprising a therapeutically effective amount of a compound of formula (I), a N-oxide, a pharmaceutically acceptable addition salt, a quaternary amine and a stereochemically isomeric form thereof, and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage, the therapeutically effective amount and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

When used as a medicament to prevent or treat Alzheimer's disease, the compounds of formula (I) may be used in combination with other conventional drugs used to combat Alzheimer's disease, such as galantamine, donepezil, rivastigmine or tacrine. Thus, the present invention also relates to the combination of a compound of formula (I) and another agent capable of preventing or treating Alzheimer's disease. Said combination may be used as a medicine. The present invention also relates to a product containing (a) a compound of formula (I), and (b) another agent capable of preventing or treating Alzheimer's disease, as a combined preparation for simultaneous, separate or sequential use in the prevention or treatment of Alzheimer's disease. The different drugs may be combined in a single preparation together with pharmaceutically acceptable carriers.

When used as a medicament to prevent or treat type 2 diabetes, the compounds of formula (I) may be used in combination with other conventional drugs used to combat type 2 diabetes, such as glibenclamide, chlorpropamide, gliclazide, glipizide, gliquidon, tolbutamide, metformin, acarbose, miglitol, nateglinide, repaglinide, acetohexamide, glimepiride, glyburide, tolazamide, troglitazone, rosiglitazone, pioglitazone, isaglitazone.

Thus, the present invention also relates to the combination of a compound of formula (I) and another agent capable of preventing or treating type 2 diabetes. Said combination may be used as a medicine. The present invention also relates to a product containing (a) a compound of formula (I), and (b) another agent capable of preventing or treating type 2 diabetes, as a combined preparation for simultaneous, separate or sequential use in the prevention or treatment of type 2 diabetes. The different drugs may be combined in a single preparation together with pharmaceutically acceptable carriers.

When used as a medicament to prevent or treat cancer, the compounds of formula (I) may be used in combination with other conventional drugs used to combat cancer such as platinum coordination compounds for example cisplatin or carboplatin; taxane compounds for example paclitaxel or docetaxel; camptothecin compounds for example irinotecan or topotecan; anti-tumour vinca alkaloids for example vinblastine, vincristine or vinorelbine; anti-tumour nucleoside derivatives for example 5-fluorouracil, gemcitabine or capecitabine; nitrogen mustard or nitrosourea alkylating agents for example cyclophosphamide, chlorambucil, carmustine or lomustine; anti-tumour anthracycline derivatives for example daunorubicin, doxorubicin or idarubicin; HER2 antibodies for example trastzumab; and anti-tumour podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene; aromatase inhibitors such as exemestane, anastrozole, letrazole and vorozole; differentiating agents for example retinoids, vitamin D and DNA methyl transferase inhibitors for example azacytidine; kinase inhibitors for example flavoperidol and imatinib mesylate or farnesyltransferase inhibitors for example R115777.

Thus, the present invention also relates to the combination of a compound of formula (I) and another agent capable of preventing or treating cancer. Said combination may be used as a medicine. The present invention also relates to a product containing (a) a compound of formula (I), and (b) another agent capable of preventing or treating cancer, as a combined preparation for simultaneous, separate or sequential use in the prevention or treatment of cancer. The different drugs may be combined in a single preparation together with pharmaceutically acceptable carriers.

When used as a medicament to prevent or treat bipolar disorder, the compounds of formula (I) may be used in combination with other conventional drugs used to combat bipolar disorder such as neuroleptica, atypical antipsychotics, anti-epileptica, benzodiazepines, lithium salts, for example olanzapine, risperidone, carbamazepine, valproate, topiramate.

Thus, the present invention also relates to the combination of a compound of formula (I) and another agent capable of preventing or treating bipolar disorder. Said combination may be used as a medicine. The present invention also relates to a product containing (a) a compound of formula (I), and (b) another agent capable of preventing or treating bipolar disorder, as a combined preparation for simultaneous, separate or sequential use in the prevention or treatment of bipolar disorder. The different drugs may be combined in a single preparation together with pharmaceutically acceptable carriers.

When used as a medicament to prevent or treat inflammatory diseases, the compounds of formula (I) may be used in combination with other conventional drugs used to combat inflammatory diseases such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine.

Thus, the present invention also relates to the combination of a compound of formula (I) and another agent capable of preventing or treating inflammatory diseases. Said combination may be used as a medicine. The present invention also relates to a product containing (a) a compound of formula (I), and (b) another agent capable of preventing or treating inflammatory diseases, as a combined preparation for simultaneous, separate or sequential use in the prevention or treatment of inflammatory disorders. The different drugs may be combined in a single preparation together with pharmaceutically acceptable carriers.

When used as a medicament to prevent or treat depression, the compounds of formula (I) may be used in combination with other conventional drugs used to combat depression such as norepinephrine reuptake inhibitors, selective serotonin reuptake inhibitors (SSRI's), monoamine oxidase inhibitors (MAOI's), reversible inhibitors of monoamine oxidase (RIMA's), serotonin and noradrenaline reuptake inhibitors (SNRI's), noradrenergic and specific serotonergic antidepressants (NaSSA's), corticotropin releasing factor (CRF) antagonists, α-adrenoreceptor antagonists and atypical antidepressants.

Suitable examples of norepinephrine reuptake inhibitors include amitriptyline, clomipramine, doxepin, imipramine, trimipramine, amoxapine, desipramine, maprotiline, nortriptyline, protriptyline, reboxetine and pharmaceutically acceptable salts thereof.

Suitable examples of selective serotonin reuptake inhibitors include fluoxetine, fluvoxamine, paroxetine, sertraline and pharmaceutically acceptable salts thereof.

Suitable examples of monoamine oxidase inhibitors include isocarboxazid, phenelzine, tranylcypromine, selegiline and pharmaceutically acceptable salts thereof.

Suitable examples of reversible inhibitors of monoamine oxidase include moclobemide and pharmaceutically acceptable salts thereof.

Suitable examples of serotonin and noradrenaline reuptake inhibitors include venlafaxine and pharmaceutically acceptable salts thereof.

Suitable atypical antidepressants include bupropion, lithium, nefazodone, trazodone, viloxazine, sibutramine and pharmaceutically acceptable salts thereof.

Other suitable antidepressants include adinazolam, alaproclate, amineptine, amitriptyline/chlordiazepoxide combination, atipamezole, azamianserin, bazinaprine, befuraline, bifemelane, binodaline, bipenamol, brofaromine, bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, monirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, tofenacin, tofisopam, toloxatone, tomoxetine, veralipride, viqualine, zimelidine and zometapine and pharmaceutically acceptable salts thereof, and St. John's wort herb, or *Hypericum perforatum*, or extracts thereof.

Thus, the present invention also relates to the combination of a compound of formula (I) and another agent capable of preventing or treating depression. Said combination may be used as a medicine. The present invention also relates to a product containing (a) a compound of formula (I), and (b) another agent capable of preventing or treating depression, as a combined preparation for simultaneous, separate or sequential use in the prevention or treatment of depression. The different drugs may be combined in a single preparation together with pharmaceutically acceptable carriers.

When used as a medicament to prevent or treat pain, the compounds of formula (I) may be used in combination with other conventional drugs used to combat pain such as nonsteroidal anti-inflammatory drugs (NSAIDS), centrally acting analgesics.

Suitable nonsteroidal anti-inflammatory drugs include salicylates, such as for example acetylsalicylic acid, ethenzamide, salicylamide; para-aminophenol derivatives, such as for example paracetamol, propacetamol, phenidine; anthranilates, such as for example etofenamate, flufenamic acid, meclofenamic acid, mefenamic acid, niflumic acid; arylacetic acids, such as for example acemetacin, bufexamac, diclofenac, indomethacin, lonazolac, sulindac, tolmetin, nabumetone; arylpropionic acids, such as for example flurbiprofen, ibuprofen, ketoprofen, naproxen, tiaprofenic acid; pyrazolinone derivatives, such as for example metamizol, propyphenazone; pyrazolidine-3,5-diones, such as for example kebuzone, mofebutazone, oxyphenbutazone, phenylbutazone; arylsulfonamides, such as for example isoxicam, lomoxicam, piroxicam, tenoxicam; ketorolac; oxaprozine; Cox-2 inhibitors, such as for example celecoxib, etodolac, meloxicam, nimesulfide, rofecoxib.

Suitable centrally acting analgesics include opioid agonists, such as for example morphine and morphinane derivatives, e.g. morphine, codeine, ethylmorphine, diacetylmorphine, dihydrocodeine, etorphine, hydrocodone, hydromorphone, levorphanol, oxycodone, oxymorphone; such as for example piperidine derivatives, e.g. pethidine, ketobemidone, fentanyl, alfentanil, remifentanil, sufentanil; such as for example methadone and congeners, e.g. levomethadone, levomethadone acetate, dextromoramide, dextropropoxyphene, diphenoxylate, loperamide, piritramide; tilidine; tramadol; viminol.

Suitable centrally acting analgesics include mixed opioid agonist-antagonists and partial agonists, such as for example buprenorphine, butorphanol, dezocine, meptazinol, nalbuphine, nalorphine, pentazocine; opioid antagonists, such as for example levallorphan, naloxone, naltrexone; non-opioid compounds, such as for example carbamazepine, clonidine, flupirtine, nefopam.

Thus, the present invention also relates to the combination of a compound of formula (I) and another agent capable of preventing or treating pain. Said combination may be used as a medicine. The present invention also relates to a product containing (a) a compound of formula (I), and (b) another agent capable of preventing or treating pain, as a combined preparation for simultaneous, separate or sequential use in the prevention or treatment of bipolar disorder. The different drugs may be combined in a single preparation together with pharmaceutically acceptable carriers.

The following examples illustrate the present invention.

Experimental Part

Hereinafter, "DMF" is defined as N,N-dimethylformamide, "DIPE" is defined as diisopropylether, "DMSO" is defined as dimethylsulfoxide, "THF" is defined as tetrahydrofuran, "DMA" is defined as N,N-dimethylacetamide.

A. Preparation of the Intermediate Compounds

EXAMPLE A1 a. Preparation of Intermediate 1

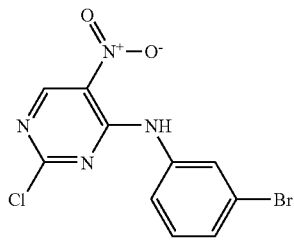

A mixture of 2,4-dichloro-5-nitropyrimidine (0.05 mol) in DMA (400 ml) was cooled to −20° C. and N-ethyl-N-(1-methylethyl)-2-propanamine (0.05 mol) was added, then a mixture of 3-bromo-benzeneamine (0.05 mol) in DMA (200 ml) was added dropwise at −20° C. and the reaction mixture was stirred at −20° C. for 2 hours. The reaction mixture containing intermediate 1 was used as such in the next reaction step.

b. Preparation of Intermediate 2

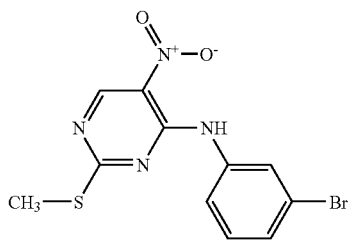

NaSCH$_3$, 21% in H$_2$O (0.05 mol) was added dropwise to intermediate 1 (0.05 mol) and the reaction mixture was stirred for 1.5 hours at room temperature, then the mixture was carefully poured out into H$_2$O. The resulting precipitate was stirred over the weekend, filtered off, washed and dried (vacuum). Yield: 15.73 g (92.5%). The product was crystallised from CH$_3$CN, then the resulting precipitate was filtered off, washed and dried (vacuum). Yield: intermediate 2.

c. Preparation of Intermediate 3

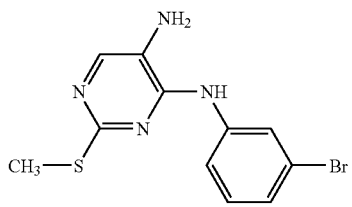

A mixture of intermediate 2 (0.028 mol) in CH$_3$OH (250 ml) was hydrogenated with Pt/C 5% (2g) as a catalyst in the presence of a solution of thiophene in DIPE (4% v/v, 1 ml). After uptake of H$_2$ (3 equiv.), the catalyst was filtered off and the filtrate was evaporated. The residue was crystallised from CH$_3$CN, then the resulting precipitate was filtered off, washed and dried (vacuum). Yield: 5.2 g of intermediate 3.

EXAMPLE A2 a. Preparation of Intermediate 4

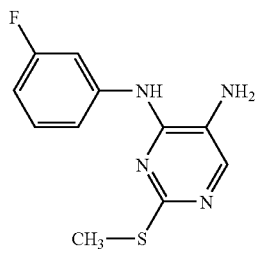

A mixture of

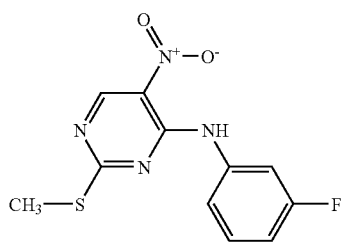

(prepared according to A1.b) (0.07 mol) and Et$_3$N (10 g) in THF (250 ml) was hydrogenated with Pd/C, 10% (5 g) as a catalyst in the presence of a solution of thiophene in DIPE (4% v/v, 5 ml). After uptake of H2 (3 equiv), the catalyst was filtered off and the filtrate was evaporated. The residue was stirred in DIPE with a small amount of CH$_3$CN. The precipitate was filtered off and dried. Yield: 12.3 g of intermediate 4 (70.2%). The filtrate was acidified with HCl/2-propanol while stirring. The mixture was stirred for 30 minutes. The resulting precipitate was filtered off and dried. Yield: 5.17 g of intermediate 4 (25.7%).

b. Preparation of Intermediate 5

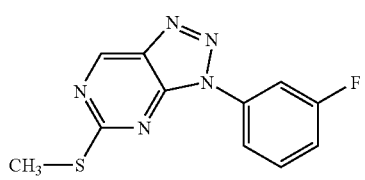

Intermediate 4 (0.08 mol) was dissolved in a mixture of 6N HCl (400 ml) and HOAc, p.a. (400 ml) and the whole was cooled to 0-5° C. A solution of NaNO$_2$ (0.1 mol) in H$_2$O (40 ml) was added dropwise over a 30 minutes period. Then, the reaction mixture was stirred for another 30 minutes while cooling on the ice-bath. Then, the mixture was stirred overnight at room temperature. The resulting precipitate was filtered off, rinsed with water, with 2-propanone, then with DIPE, and dried. Yield: 18.14 g of intermediate 5 (87%).

c-1. Preparation of Intermediate 6

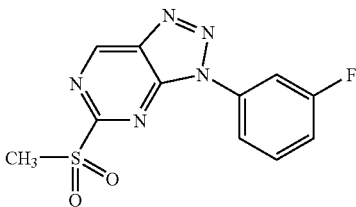

Intermediate 5 (15 g, 0.058 mol) was stirred in HOAc (700 ml) and cooled on an ice-bath. A solution of KMnO$_4$, p.a. (24 g, 0.15 mol) in demineralized H$_2$O (300 ml) was added dropwise over a 60 minutes period while cooling on an ice-bath. The mixture was stirred for one hour on the ice-bath, then for 2 hours at room temperature. Sodium bisulfite was added until a colour change resulted. EtOAc was added while stirring vigorously for a while. The mixture was stood overnight. The mixture was concentrated to ±50-ml volume. The aqueous concentrate was stirred for a while and the resulting 5 precipitate was filtered off and dried. Yield: 11.023 g of intermediate 6 (64.8%).

c-2. Preparation of Intermediate 34

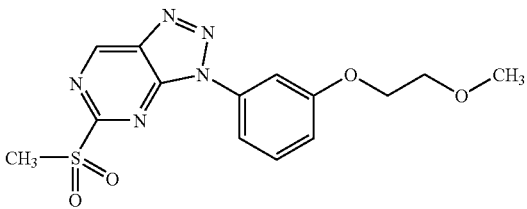

A mixture of 3-chlorobenzenecarboperoxoic acid (0.0125 mol, dry) in CH$_2$Cl$_2$ (100 ml) was dried (MgSO$_4$), filtered off and the filtrate was added dropwise to a solution of intermediate 33

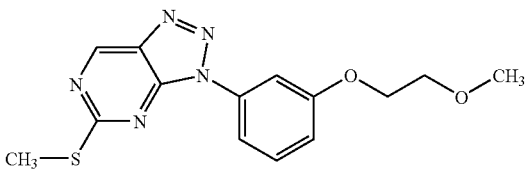

(prepared according to A2.b) (0.0063 mol) in CH$_2$Cl$_2$ (100 ml), then the reaction mixture was stirred overnight at room temperature and washed with a NaHCO$_3$/H$_2$O solution. The organic layer was separated, dried (MgSO$_4$), filtered off and the solvent was evaporated. The residue was suspended in DIPE/CH$_3$CN, then the desired product was filtered off, washed and dried (vacuum). Yield: 1.9 g of intermediate 34.

c-3. Preparation of Intermediate 36

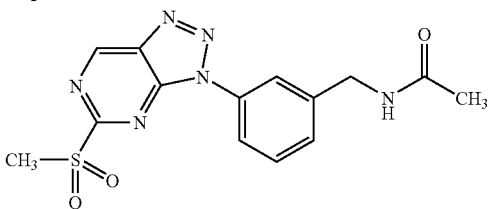

A mixture of intermediate 35

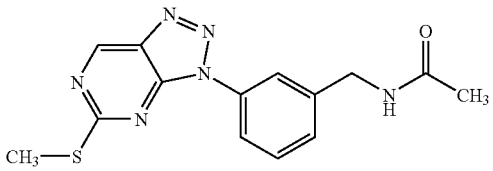

(prepared according to A2.b) (0.02 mol) in CH$_2$Cl$_2$, p.a. (250 ml) and methanol, p.a. (50 ml) was stirred at room temperature until complete dissolution and then 3-chlorobenzenecarboperoxoic acid (0.04 mol. 70%) was added portionwise. The reaction mixture was stirred for 2 hours at room temperature and extra 3-chlorobenzenecarboperoxoic acid (2×2.5 g, every half hour) was added. The resulting mixture was stirred overnight at room temperature and washed with a calculated NaHCO$_3$/H$_2$O solution. The organic layer was separated, dried (MgSO$_4$), filtered off and the solvent was evaporated. The residue was crystallised from CH$_3$CN, then the resulting precipitate was filtered off and dried.

The filtrate was evaporated and the residue was purified by Flash column chromatography (eluent: CH$_2$Cl$_2$/CH$_3$OH 98/2). The product fractions were collected and the solvent was evaporated. The residue was recrystallised from CH$_3$OH with a small amount of H$_2$O, then the resulting precipitate was filtered off and dried. Yield: 1.984 g of intermediate 36 (29%).

c-4a. Preparation of Intermediate 38

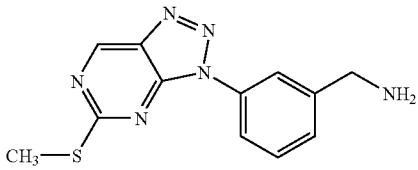

A mixture of intermediate 35

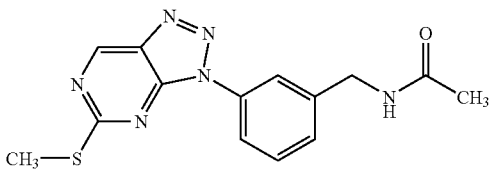

(prepared according to A2.b) (0.020 mol) in 12 N HCl, p.a. (100 ml) and H$_2$O (demineralised) (200 ml) was stirred and refluxed for 6 hours, then the reaction mixture was stirred over the weekend at room temperature. The resulting precipitate was filtered off and dried. Yield: 3.61 g of intermediate 38 (58.5%, m.p.: >260° C.).

c-4b. Preparation of Intermediate 39

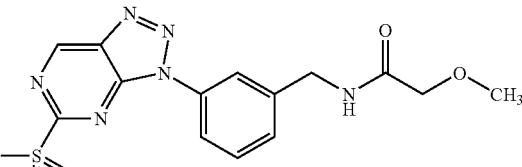

A mixture of intermediate 38 (prepared according to A2.c-4a) (0.001 mol) and Et$_3$N (0.0025 mol) in CH$_2$Cl$_2$, p.a. (15 ml) was stirred at room temperature and a mixture of methoxyacetyl chloride (0.0012 mol) in CH$_2$Cl$_2$, p.a. (1 ml) was added dropwise, then the reaction mixture was stirred overnight at room temperature and washed with H$_2$O. The organic layer was separated, dried, filtered off and the solvent was evaporated.

The residue was dissolved in CH$_2$Cl$_2$ (15 ml) and 3-chlorobenzenecarboperoxoic acid (0.002 mol, 70%) was added. The resulting mixture was stirred for 2 hours at room temperature and washed with a NaHCO$_3$ solution. The organic layer was separated, dried, filtered off and the solvent was evaporated. The residue was stirred overnight in DIPE and then the resulting precipitate was filtered off and dried. Yield: 0.392 g intermediate 39 (100%).

c-5. Preparation of Intermediate 41

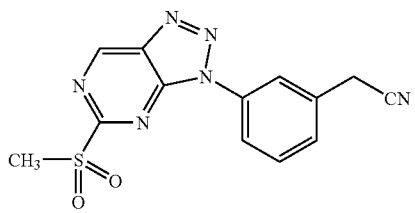

A mixture of intermediate 40

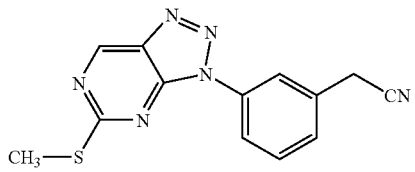

(prepared according to A2.b) (0.010 mol) in CH$_2$Cl$_2$ (80 ml) and methanol (20 ml) was stirred at room temperature and 3-chlorobenzenecarboperoxoic acid (0.024 mol) was added portionwise. The reaction mixture was stirred for 3 hours at room temperature, then a mixture of NaHCO$_3$ (0.025 mol) in H$_2$O was added and the resulting mixture was stirred firmly. When the generation of gas was stopped, the layers were separated. The organic layer was dried (MgSO$_4$), filtered off and the solvent was evaporated. The residue was stirred in DIPE with a small amount of CH$_3$CN, then the precipitate was filtered off and dried. Yield: 1.218 g of intermediate 41 (39%).

c-6. Preparation of Intermediate 42

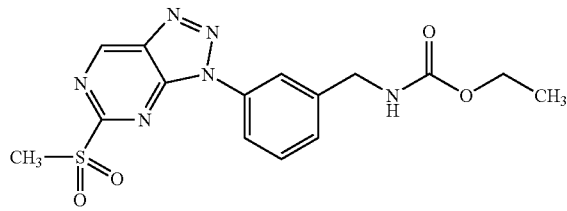

A mixture of intermediate 38 (prepared according to A2.c-4a) (0.005 mol) in CH$_2$Cl$_2$ (50 ml) was stirred at room temperature and morpholinomethyl Polystyrene HL resin (loading 4 mmol/g) (200-400 mesh) (0.020 molNovabiochem) was added, then a mixture of ethyl chloroformate (0.006 mol) in CH$_2$Cl$_2$ (20 ml) was added dropwise at room temperature and the reaction mixture was stirred over the weekend at room temperature. The mixture was filtered over a glass filter and the scavenger was rinsed with CH$_2$Cl$_2$/CH$_3$OH (30 ml; 80/20). 3-chlorobenzenecarboperoxoic acid (0.015 mol; 70%) was added to the filtrate and the resulting mixture was stirred overnight. Extra 3-chlorobenzenecarboperoxoic acid (1 g) was added and the mixture was stirred for another 8 hours, then (polystyrylmethyl)trimethylammonium bicarbonate scavenger (0.045 mol; loading: 3.7 mmol/g; 20-50 mesh; Novabiochem) was added and the reaction mixture was stirred overnight at room temperature. The scavenger was filtered off and the filtrate was evaporated, yielding intermediate 42.

EXAMPLE A2a a. Preparation of Intermediate 20

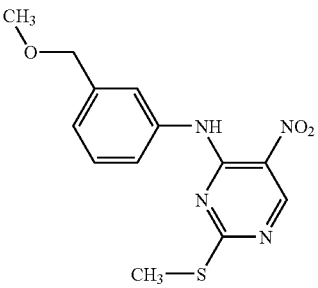

A solution of 2,4-dichloro-5-nitropyrimidine (0.047 mol) in DMF (100 ml) was cooled to −50° C. and a mixture of 3-(methoxymethyl)benzenamine (0.047 mol) in DMF (50 ml) was added dropwise, then the mixture was stirred at −50° C. for 4 hours and NaSCH$_3$ (0.1 mol) was added dropwise. The reaction mixture was stirred over the weekend at room temperature and the resulting precipitate was filtered off, washed with H$_2$O and dried (vacuum), yielding intermediate 20.

b. Preparation of Intermediate 21

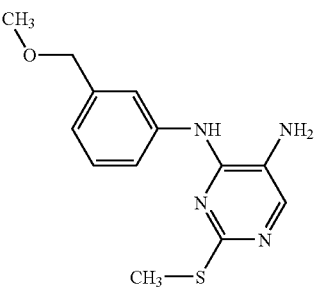

A mixture of intermediate 20 (prepared according to A2a.a) (0.029 mol) in methanol (150 ml) and THF (100 ml) was hydrogenated with Pd/C (2 g) as a catalyst in the presence of thiophene solutions (2 ml). After uptake of H$_2$ (3 equiv., 2181 ml), the catalyst was filtered off and the filtrate was evaporated. Yield: 9 g of intermediate 21.

c. Preparation of Intermediate 22

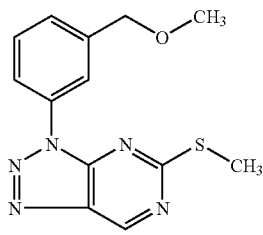

Intermediate 21 (prepared according to A2a.b) (0.029 mol) was stirred in acetic acid, p.a. (100 ml) at room temperature and 1N HCl, p.a. (30 ml) was added, then a mixture of NaNO$_2$ (0.03 mol) in H$_2$O (20 ml) was added dropwise and the reaction mixture was stirred at room temperature for 1 hour. H$_2$O (200 ml) and a saturated NaCl solution (50 ml) were added and the mixture was extracted 3 times with EtOAc. The organic layer was evaporated and the concentrate was purified over silica gel (eluent gradient: CH$_2$Cl$_2$/Hexane from 50/50 to 100/0). The product fractions were collected and the solvent was evaporated. Yield: 5 g intermediate 22 (60%).

d. Preparation of Intermediate 23

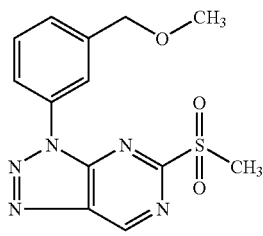

A mixture of intermediate 22 (prepared according to A2a.c) (0.017 mol) in CH$_2$Cl$_2$ (200 ml) was stirred and 3-chlorobenzenecarboperoxoic acid (0.04 mol) was added at room temperature, then the reaction mixture was stirred at room temperature and washed with a calculated NaHCO$_3$/H$_2$O-solution. The organic layer was dried (MgSO$_4$), filtered off and the solvent was evaporated. The residue was crystallised from CH$_3$CN and the resulting precipitate was filtered off and dried. Yield: 3.04 g (56 %) of intermediate 23. The filtrate was evaporated and the residue was crystallised from H$_2$O/CH$_3$OH. The precipitate was filtered off and dried. Yield: 1.086 g of intermediate 23 (20%).

EXAMPLE A2b a. Preparation of Intermediate 51

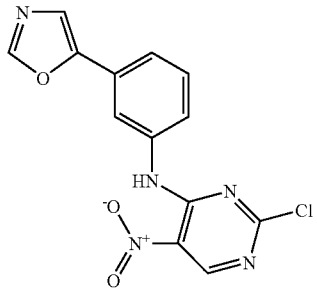

A mixture of 2,4-dichloro-5-nitropyrimidine (5 mmol) in CH$_2$Cl$_2$ (20 ml) was stirred at −30° C./−40° C. Alternately, a solution of 3-(5-oxazolyl)-benzenamine (5 mmol) in CH$_2$Cl$_2$ (10 ml) and a solution of N,N-diethylbenzenamine (5 mmol) in CH$_2$Cl$_2$ (10 ml) were added dropwise over a period of 1 hour, followed by stirring for 2 hours at −20 ° C./−30° C. The mixture was allowed to come to room temperature while stirring. The mixture was diluted with 50 ml of CH$_2$Cl$_2$ and 50 ml of ice water was added. The precipitate was filtered and dried. Yield: 490 mg of intermediate 51. Of the filtrate, the layers were separated and the organic layer was dried, filtered and evaporated. The residue was stirred in CH$_3$CN. The precipitate was filtered off and dried. Yield: 305 mg of intermediate 51.

b. Preparation of Intermediate 52

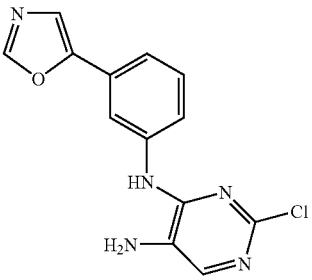

A mixture of intermediate 51 (1 mmol) in THF (50 ml) was hydrogenated with Pt/C 5% (0.2 g) as a catalyst in the presence of a solution of thiophene in DIPE (4% v/v, 0.5 ml) and in the presence of triethylamine (equimolar). After uptake of H$_2$, the catalyst was filtered off and the filtrate was evaporated. Yield: 300 mg of intermediate 52.

c. Preparation of Intermediate 45

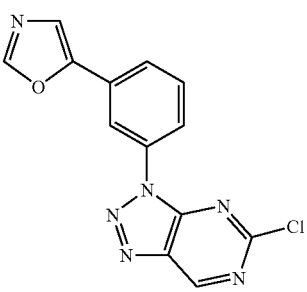

A mixture of intermediate 52 (prepared according to A2b.b) (0.001 mol) and HCl 1N (0.002 mol) in acetic acid (20 ml) was stirred at room temperature, then a mixture of NaNO$_2$ (0.001 mol) in H$_2$O (2 ml) was added dropwise and the reaction mixture was stirred overnight at room temperature. The solvent was evaporated and the residue was stirred in CH$_3$CN. The resulting precipitate was filtered off and dried. Yield: 0.190 g of intermediate 45.

EXAMPLE A3 a. Preparation of Intermediate 7

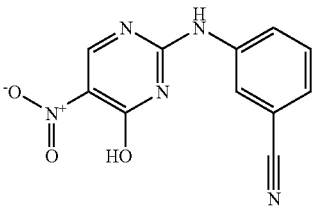

A mixture of 2-chloro-5-nitro-4(1H)-Pyrimidinone (0.005 mol) and 3-amino-benzonitrile (0.005 mol) in 2-methoxyethanol (25 ml, p.a.) was stirred for 3 hours at 100-110° C. The solvent was evaporated and the residue was stirred in CH$_3$CN with a small amount of CH$_3$OH. The resulting precipitate was filtered off and dried. Yield: 1.300 g of intermediate 7 (100%).

b. Preparation of Intermediate 8

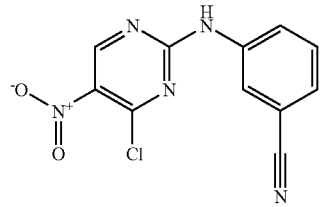

A mixture of intermediate 7 (0.006 mol) in POCl$_3$ (15 ml) was stirred for 2 hours at 95 °C., then the reaction mixture was stirred overnight at room temperature. The solvent was evaporated and the residue was stirred in 2-propanol/H$_2$O/CH$_3$OH. The resulting precipitate was filtered off and dried. Yield: 1.143 g of intermediate 8 (69%).

c. Preparation of Intermediate 9

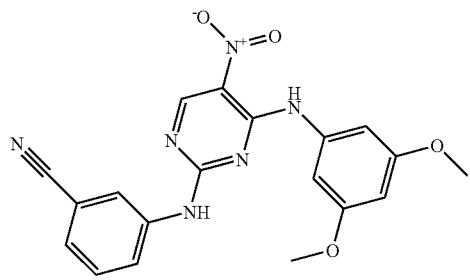

A mixture of 3,5-dimethoxybenzenamine (0.001 mol) and intermediate 8 (0.001 mol) in ethanol (20 ml) was heated to reflux (±10 minutes) and the reaction mixture was stirred overnight at room temperature. The resulting precipitate was filtered off and dried. Yield: 0.327 g of intermediate 9 (83%).

EXAMPLE A4 a. Preparation of Intermediate 10

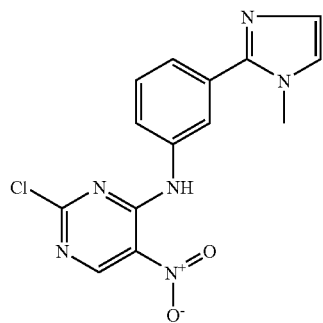

A solution of 2,4-dichloro-5-nitropyrimidine (0.0127 mol) in DMF (60 ml) was stirred at 0° C. N-ethyl-N-(1-methylethyl)-2-propanamine (0.0127 mol) was added. A solution of 3-(1-methyl-1H-imidazol-2-yl)benzenamine (0.0127 mol) in DMF (20 ml) was added dropwise and the resulting reaction mixture was stirred for one hour at 0° C., then overnight at room temperature. The reaction mixture containing intermediate 10 was used as such in the next reaction step.

b. Preparation of Intermediate 11

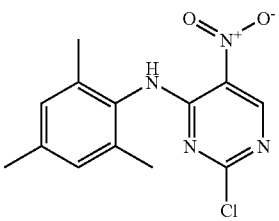

2,4,6-Trimethylbenzenamine (0.0259 mol), 2,4-dichloro-5-nitropyrimidine (0.0259 mol) and 1,4-dioxane (25 ml) were combined in a RB flask equipped with stirbar and reflux condenser under Ar and heated to reflux for 16 hours. The sample was concentrated by rotary evaporation onto silica gel and purified by column chromatography twice (Biotage 40M, 1:1 hexanes: methylene chloride, second purification: eluent: 25%-->40% methylene chloride in hexanes) to give intermediate 11.

EXAMPLE A5 a. Preparation of Intermediate 12

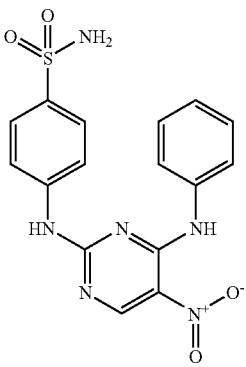

4-Aminobenzenesulfonamide (0.046 mol) was added to a solution of N-ethyl-N-(1-methylethyl)-2-propanamine (6 g) in 2-chloro-5-nitro-N-phenyl-4-pyrimidinamine (153 ml) and the reaction mixture was heated overnight at 60° C., then the mixture was added dropwise to ice-water (500 ml). The resulting solids were filtered off and dried in a vacuum oven at 60° C., then suspended in DIPE/CH$_3$OH. The suspension was recrystallised from diglyme (diethylene glycol dimethyl ether) and the resulting solids were collected. Yield: 4.7 g of intermediate 12.

b. Preparation of Intermediate 13

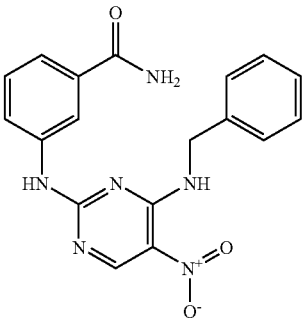

A solution of 2-chloro-5-nitro-N-(phenylmethyl)-4-pyrimidinamine (0.012 mol), 3-aminobenzamide (0.012 mol) and N,N-diethylethanamine (0.012 mol) in DMF (50 ml) was stirred for 2 hours at 60° C. The mixture was allowed to cool to room temperature and methanol (10 ml) was added. The mixture was stirred for 10 minutes and the resulting precipitate was filtered off, washed and dried. Yield: 3.3 g of intermediate 13 (77%).

c. Preparation of Intermediate 14

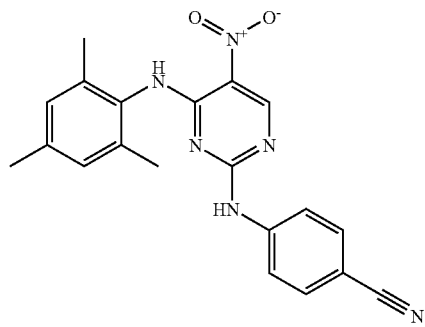

Intermediate 11 (0.0547 mol), 4-aminobenzonitrile (0.01367 mol) and 1,4-dioxane (30 ml) were combined and heated to 60° C. for 4 days. 1,4-Dioxane was removed by rotary evaporation. The pH of the reaction mixture was adjusted to >10 using 1 N NaOH. CH$_2$Cl$_2$ was added to the reaction mixture, the resulting emulsion was filtered and the yellow solid was washed with copious methylene chloride to give intermediate 14.

EXAMPLE A6

Preparation of Intermediate 15

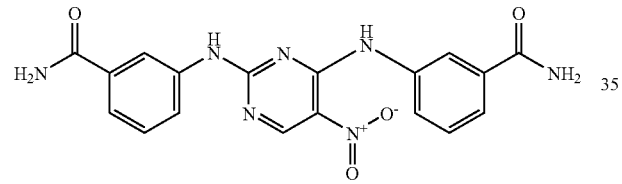

A mixture of 2,4-dichloro-5-nitropyrimidine (0.038 mol) in CH$_2$Cl$_2$ (100 ml) was cooled to 0° C. and N-ethyl-N-(1-methylethyl)-2-propanamine (0.038 mol) was added. A solution of 3-aminobenzamide (0.038 mol) in DMF (30 ml) was added dropwise. Then the reaction mixture was allowed to warm to room temperature and was stirred for the weekend. The formed precipitate was filtered off and washed. The filtrate was concentrated. Yield: 2.7 g of intermediate 15.

EXAMPLE A6a

Preparation of Intermediate 24

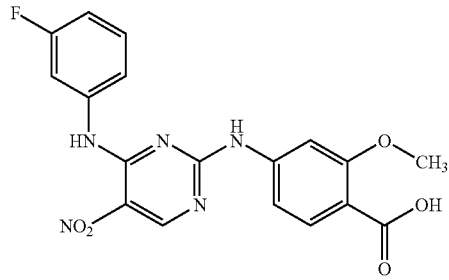

A solution of 2,4-dichloro-5-nitropyrimidine (0.005 mol) in DMF (25 ml) was cooled to −60° C., then a mixture of 3-fluorobenzenamine (0.005 mol) in DMF (12.5 ml) was slowly added dropwise and the mixture was stirred for 2 hours at −40° à −60° C. A mixture of 4-amino-2-methoxybenzoic acid (0.005 mol) in DMF (12.5 ml) was slowly added dropwise at −50° C. and the reaction mixture was stirred overnight. H$_2$O and CH$_3$CN were added, then the resulting precipitate was filtered off, washed and dried (vacuum), yielding intermediate 24.

EXAMPLE A7 a. Preparation of Intermediate 16

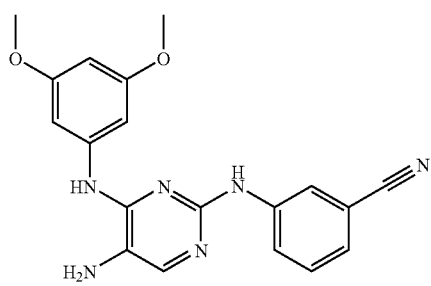

A mixture of intermediate 9 (0.0008 mol) in ethanol (40 ml) was hydrogenated with Pt/C 5% (0.050 g) as a catalyst in the presence of a solution of thiophene in DIPE (4% v/v, 0.05 ml). After uptake of hydrogen (3 equiv.), the catalyst was filtered off and the filtrate was evaporated. Yield: 10.5 g of intermediate 16 (100%).

b. Preparation of intermediate 17

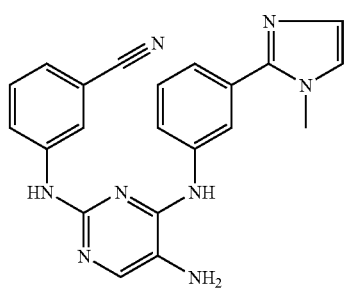

(0.0127 mol; prepared from intermediate 10 (A4a.) according to A5a.-A5b.) in DMF (80 ml) was hydrogenated at room temperature with Pd/C 10% (2 g) as a catalyst in the presence of a solution of thiophene in DIPE (4% v/v, 2 ml). After uptake of hydrogen (3 equiv), the catalyst was filtered off and the solvent was evaporated, yielding intermediate 17.

c. Preparation of Intermediate 18

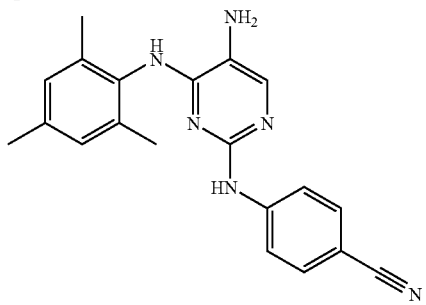

Intermediate 14 (0.001 mol), Pd/C 10% (0.025 g), ethanol (20 ml), and NH$_2$—NH$_2$ (0.030 mol) were combined to form a slurry and stirred at room temperature for 16 hours. The solvent was removed by rotary evaporation. The residue was taken up in THF (20 ml) and methanol (1 ml). A second portion of NH$_2$—NH$_2$ (0.5 g) was added, and the reaction was stirred for 16 hours at room temperature. A third portion of NH$_2$—NH$_2$ (0.5 ml) was added and the reaction was stirred for an additional 16 hours at room temperature. The sample was concentrated by rotary evaporation onto silica gel (1 g) and purified by flash chromatography (Biotage 40S, eluent: 0.5, 1,2% 10% (NH$_4$OH in CH$_3$OH) in CH$_2$Cl$_2$) to give a solid. Trituration with a variety of solvents was done and the portions were recombined and purified by preparatory HPLC to give the final solid after the combined HPLC fractions were lyophilized. Yield: 0.24 g of intermediate 18 (70%).

EXAMPLE A8

Preparation of Intermediate 19

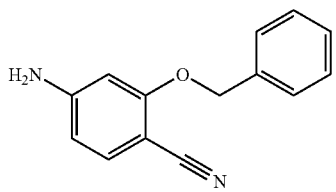

A mixture of Fe (0.12 mol) in 0.78 N NH$_4$Cl solution (70 ml) was stirred at reflux temperature. 4-nitro-2-(phenylmethoxy)benzonitrile (0.047 mol) was added in small portions. The resultant reaction mixture was stirred and refluxed for 4 hours, then cooled, filtered and the residue was extracted on Soxhlet with toluene. The extract's solvent was evaporated. The residue was dried in vacuo. Yield: 8.2 g of intermediate 19 (78%).

EXAMPLE A9 a. Preparation of Intermediate 25

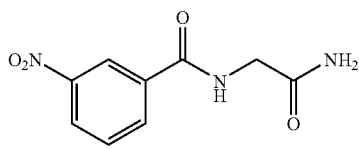

A solution of 3-nitrobenzoyl chloride (18.6 g, 0.10 mol) in acetone (100 ml) was added dropwise to a stirred solution of glycinamide hydrogen chloride (11.1 g, 0.10 mol) and sodium bicarbonate (16.8 g, 0.20 mol) in water (50 ml) at room temperature. The reaction was stirred for a further 2 hours, after which the solvent was removed by rotary evaporation. The residue was triturated under water, and dried in vacuo. Yield: 18.2 g of intermediate 25 (82%).

b. Preparation of Intermediate 26

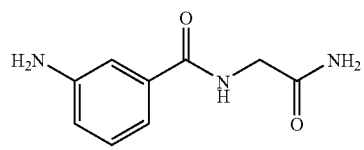

A solution of intermediate 25 (prepared according to A9.a) (18.2 g, 0.082 mol) in methanol (250 ml) was stirred over Pd/C (5%, 2 g) under an atmosphere of hydrogen for 16 hours. The mixture was filtered through celite, and the celite washed with methanol. The solvent was removed by rotary evaporation, and the residue triturated under diethyl ether. The residue was dried in vacuo. Yield: 14.4 g of intermediate 26.

EXAMPLE A10 a. Preparation of Intermediate 27

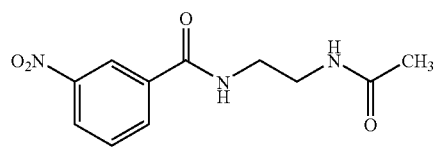

A solution of 3-nitrobenzoyl chloride (18.6 g, 0.10 mol) in acetone (100 ml) was added dropwise to a stirred solution of 2-acetylaminoethylamine (11.1 g, 0.10 mol) and sodium bicarbonate (8.4 g, 0.10 mol) in water (50 ml) at room temperature. The reaction was stirred for a further 2 hours, after which the solvent was removed by rotary evaporation. The residue was triturated under water, and dried in vacuo. Yield: 14.2 g of intermediate 27 (57%).

b. Preparation of Intermediate 28

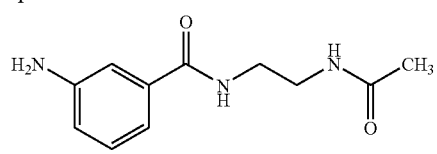

A solution of intermediate 27 (prepared according to A10.a) (14.2 g, 0.082 mol) in methanol (250 ml) was stirred over Pd/C (5%, 2 g) under an atmosphere of hydrogen for 16 hours. The mixture was filtered through celite, and the celite washed with methanol. The solvent was removed by rotary evaporation, and the residue triturated under diethyl ether. The residue was dried in vacuo. Yield: 10.6 g of intermediate 28 (85%).

EXAMPLE A11 a. Preparation of Intermediate 29

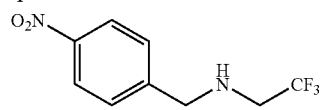

A mixture of 4-nitrobenzaldehyde (0.045 mol), 2,2,2-trifluoroethanamine (0.050 mol), HOAc (q.s.) and molecular sieves (q.s.) in CH$_2$Cl$_2$ (q.s.) was stirred for 1 hour at 20° C., then NaBH(OAc)$_3$ (q.s.) was added and the reaction mixture was stirred for 48 hours. The mixture was filtered over celite and the filtrate was partitioned between EtOAc and a saturated aqueous NaHCO₃ solution. The organic layer was washed with water and with brine, then dried (MgSO₄) and the solvent was evaporated. Yield: 10 g of intermediate 29.

b. Preparation of Intermediate 30

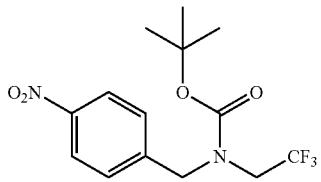

Bis(1,1-dimethylethyl)dicarbonic acid ester (0.043 mol) was added portionwise to a solution of intermediate 29 (prepared according to A11.a) (0.043 mol) in CH₂Cl₂ (500 ml) on an ice-water bath, then the reaction mixture was allowed to reach 20° C. and was stirred for 16 hours. Extra bis(1,1-dimethylethyl)dicarbonic acid ester (9 g) was added, followed by N,N-dimethyl-4-pyridinamine (1 g) and the resulting mixture was stirred for 24 hours. Again extra bis(1,1-dimethylethyl)dicarbonic acid ester (5 g) and N,N-dimethyl-4-pyridinamine (2 g) were added and after stirring for 24 hours, the mixture was cooled to 0° C. NH₃/CH₃OH (7 M) was added (to quench the remaining bis(1,1-dimethylethyl) dicarbonic acid ester) and the mixture was washed with an 80% saturated aqueous NaHCO₃ solution, with H₂O and then with brine. The organic layer was separated, dried (MgSO₄) and the solvent was evaporated. The residue was filtered over silica gel (eluent: CH₂Cl₂) and the obtained residue was collected. Yield: 12 g of intermediate 30.

c. Preparation of Intermediate 31

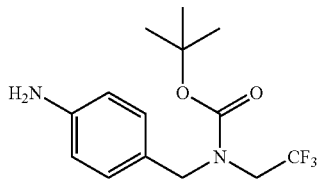

A mixture of intermediate 30 (prepared according to A11.b) (0.036 mol) in methanol (250 ml) was hydrogenated at 50° C. with Pd/C 10% (2 g) as a catalyst in the presence of thiophene solution, 4% in DIPE (1ml). After uptake of H₂ (3 equivalents), the catalyst was filtered off and the solvent was evaporated. The residue was purified by flash column chromatography (eluent gradient: CH₂Cl₂/CH₃OH 100/0 to 98.5/1.5). The product fractions were collected and the solvent was evaporated. Yield: 10 g of intermediate 31 (91%).

B. Preparation of the Final Compounds

EXAMPLE B1 a-1) Preparation of Compound 1

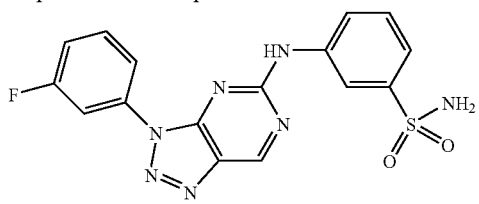

A mixture of intermediate 6 (prepared according to A2.c-1) (0.00034 mol) and 3-aminobenzenesulfonamide (0.00034 mol) in DMSO (2 ml) was stirred overnight at 100° C., then H₂O and CH₃CN were added and the reaction mixture was warmed. The resulting precipitate was filtered off, washed and dried (vacuum). Yield: 0.032 g of compound 1 (m.p. 177° C.)

a-2). Preparation of Compound 32

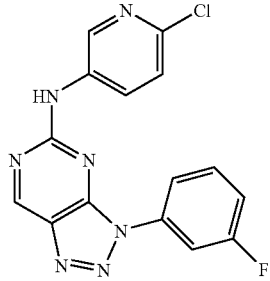

A mixture of intermediate 6 (prepared according to A2.c-1) (0.0001 mol) and 6-chloro-3-pyridinamine (0.0002 mol) in DMSO (0.5 ml) was stirred at 100° C. for 3 hours and then the reaction mixture was cooled and further purified by reverse phase LCMS. The product fractions were collected and the solvent was evaporated, yielding compound 32.

b-1) Preparation of Compound 2

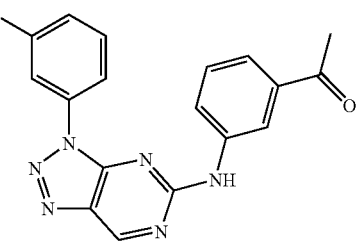

A mixture of intermediate 6 (prepared according to A2.c-1) (0.001 mol) and 1-(3-aminophenyl)ethanone (0.002 mol) in 2-methoxyethanol (10 ml) was stirred and refluxed for 16 hours and the solution was cooled. The resulting precipitate was filtered off, rinsed with EtOH/DIPE and dried. Yield: 0.250 g of compound 2 (72%, m.p. 220-224° C.). The filtrate was evaporated and the residue was stirred in CH₃CN/CH₃OH (2 ml/2 ml). The mixture was stirred for a while, then the precipitate was filtered off and dried. Yield: 0.098 g of compound 2 (28%).

b-2). Preparation of Compound 287

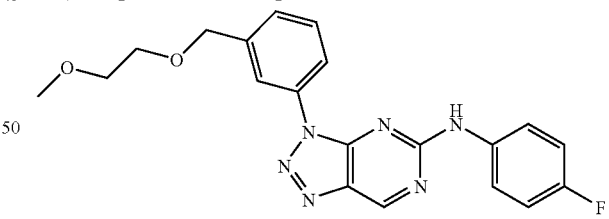

A mixture of intermediate 49 (prepared according to A2a.d)

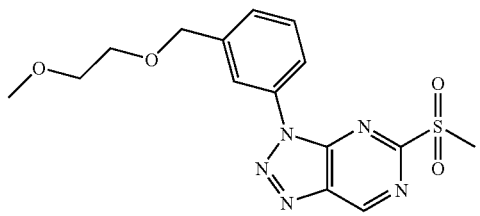

(0.00028 mol) and 4-fluorobenzenamine (0.00055 mol) in 2-methoxyethanol (2 ml) was stirred overnight at 100° C. and the reaction mixture was cooled to room temperature, then H₂O and CH₃CN were added. After crystallisation, the resulting precipitate was filtered off, washed and dried (vacuum). Yield: 0.0739 g of compound 287, m.p.: 148° C.)

b-3). Preparation of Compound 214

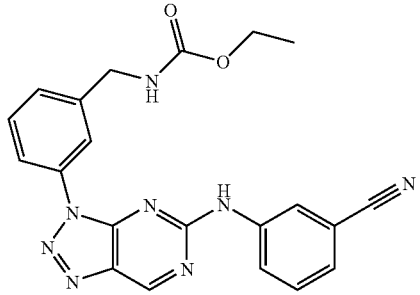

A mixture of intermediate 42 (prepared according to A2.c-6) (0.0002 mol) and 3-aminobenzonitrile (0.0004 mol) in 2-methoxyethanol (2 ml) was stirred for 20 hours at 120° C. and then the crude mixture was purified by high-performance liquid chromatography. The pure product fractions were collected and the solvent was evaporated. The obtained residue was dissolved in CH₃OH and then the solvent was evaporated. Yield: 0.006 g of compound 214.

b-4). Preparation of Compound 27

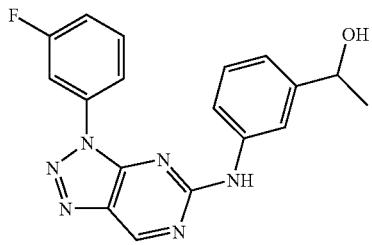

A mixture of intermediate 6 (prepared according to A2.c-1) (0.0005 mol) and 3-amino-a-methylbenzenemethanol (0.001 mol) in 2-methoxyethanol (2 ml) was stirred for 30 minutes at 80° C. and then the solvent was evaporated. The residue was crystallised from CH₃CN; the resulting precipitate was filtered off and dried. Yield: 0.155 g of compound 27, (m.p.: 150-154° C.).

b-5). Preparation of Compound 28

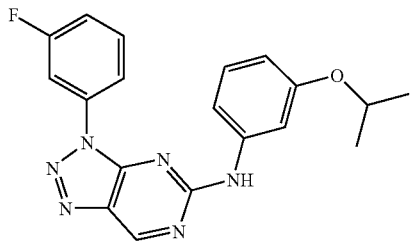

A mixture of intermediate 6 (prepared according to A2.c-1) (0.0005 mol) and 3-(1-methylethoxy)benzenamine (0.001 mol) in 2-methoxyethanol (2 ml, p.a.) was stirred for 30 minutes at 80° C., then the reaction mixture was allowed to cool and blown dry under N₂ to ½ of the initial volume. The concentrate was diluted with CH₃OH (2 ml) and the mixture was recrystallised. The resulting precipitate was filtered off and the solvent was evaporated. Yield: 0.134 g of compound 28 (74%, m.p.: 142-146° C.)

b-6). Preparation of Compound 55

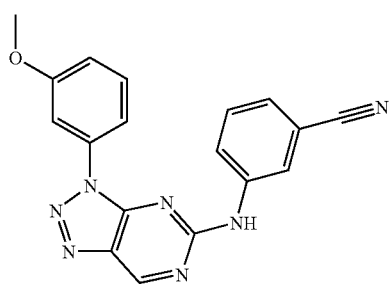

A mixture of intermediate 50

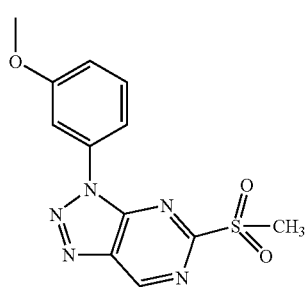

(prepared according to A2a.d) (0.0005 mol) and 3-aminobenzonitrile (0.0005 mol) in 2-methoxybenzenamine (2 ml) was stirred for 10 hours at 100° C., then stirred at 70° C. for 48 hours. The reaction mixture was diluted with CH₃OH (2 ml) and stirred at room temperature. The resulting precipitate was filtered off and crystallised from CH₃CN (3 ml), EtOH (2 ml) and from DMF (1 ml). Finally, the resulting precipitate was filtered off and dried. Yield: 0.068 g of compound 55 (40%, m.p.: 228-231 ° C.).

b-7a). Preparation of Compound 148

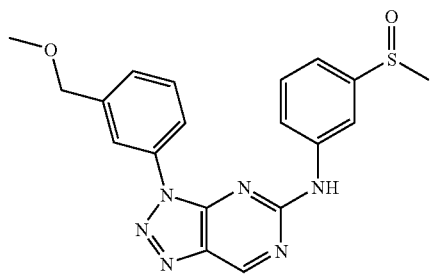

A mixture of intermediate 23 (prepared according to A2a.d) (0.0003 mol), 3-(methylsulfinyl)benzenamine (0.0003 mol) and N-ethyl-N-(1-methylethyl)-2-propanamine (0.0003 mol) in 2-propanol (3 ml) was stirred for 16 hours at 80° C. and then the solvent was evaporated. The residue was taken up in H₂O and the mixture was extracted with CH₂Cl₂. The organic layer was separated, dried, filtered off and the solvent was evaporated. The residue was purified by Flash column chromatography (eluent: CH₂Cl₂/CH₃OH 98/2). The product fractions were collected and the solvent was evaporated. The residue was crystallised from CH₃CN with a small amount of H₂O, then the resulting precipitate was filtered off and dried. Yield: 0.037 g of compound 148 (31%, m.p.: 142-146° C.).

b-7b). Preparation of Compound 152

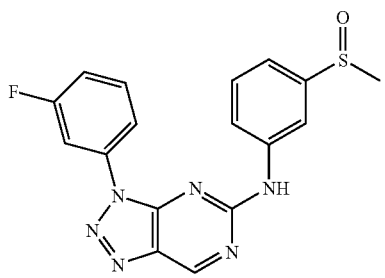

A mixture of intermediate 6 (prepared according to A2.c-1) (0.0005 mol) and 3-(methylsulfinyl)benzenamine (0.0005 mol) in 2-methoxyethanol (3 ml, p.a.) was stirred and N-ethyl-N-(1-methylethyl)-2-propanamine (0.0005 mol) was added, then the reaction mixture was stirred for 16 hours at 80° C. and the solvent was evaporated. The residue was purified by column chromatography over silica gel (eluent gradient: $CH_2Cl_2/CH_3OH$ 100/0 to 98/2). The product fractions were collected and the solvent was evaporated. The residue was crystallised from $CH_3CN$ and then the resulting precipitate was filtered off and dried. Yield: 0.102 g of compound 152 (55%, m.p.: 168-172° C.)

b-8). Preparation of Compound 297

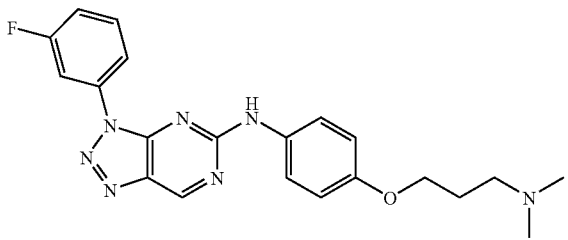

A mixture of intermediate 6 (prepared according to A2.c-1) (0.00025 mol) and 4-[3-(dimethylamino)propoxy]benzenamine (0.0005 mol) in 2-methoxyethanol (2 ml) was stirred for 90 minutes at 100° C. and then the solvent was evaporated. The residue was purified by high-performance liquid chromatography. The desired fractions were evaporated in the Genevac and each residual fraction was dissolved in $CH_3OH$, then the fractions were combined and the solvent was evaporated. Yield: 0.0388 g of compound 297 (m.p.: 137° C.).

b-9). Preparation of Compound 313

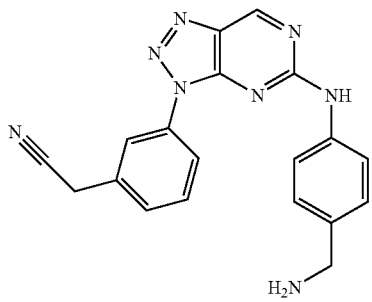

A mixture of intermediate 32

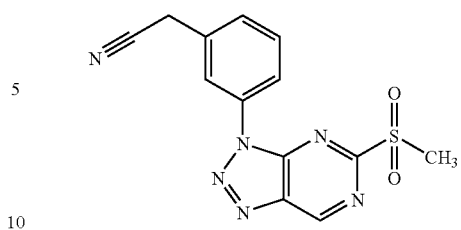

(prepared according to A2a.d) (0.00040 mol) and [(4-aminophenyl)methyl]carbamic acid 1,1-dimethylethyl ester (0.00060 mol) in 2-methoxyethanol (0.8 ml) was shaken under gentle heating until complete dissolution and then the reaction mixture was shaken for 1 hour at 100° C. After cooling, the mixture was filtered and washed with $CH_3CN$ and with DIPE. The obtained residue was dissolved in warm 2-methoxyethanol (q.s.) and the solution was heated to 60° C. HCl, 6M in 2-propanol (0.5 ml) was added and the resulting mixture was allowed to cool to 20° C. over 16 hours while stirring. The solvent was evaporated and the obtained residue was triturated under $CH_3CN$, then the desired product was filtered off, washed with $CH_3CN$ and with DIPE and dried for 16 hours in a vacuum oven, yielding compound 313.

b-10). Preparation of Compound 202

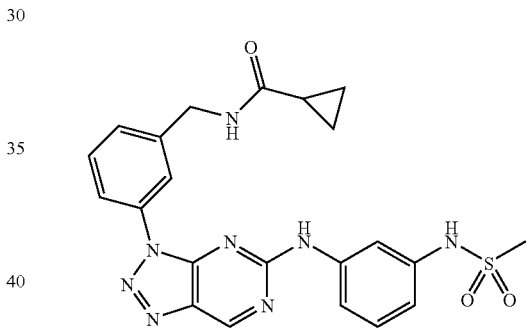

A mixture of intermediate 43

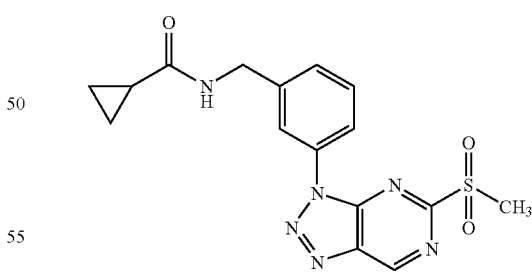

(prepared according to A2.c-6) (0.0002 mol), N-(3-aminophenyl)methane sulfonamide (0.0004 mol) in 2-methoxyethanol (2 ml) was stirred at least overnight at at least 80° C. and then the crude mixture was purified by high-performance liquid chromatography. The product fractions were collected and the solvent was evaporated (Genevac). The obtained residue was dissolved in $CH_3OH$ and then the solvent was evaporated (Genevac), yielding compound 202.

b-11). Preparation of Compound 231

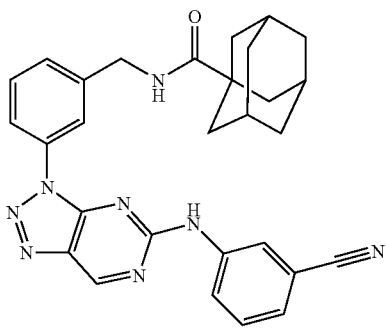

A mixture of intermediate 44

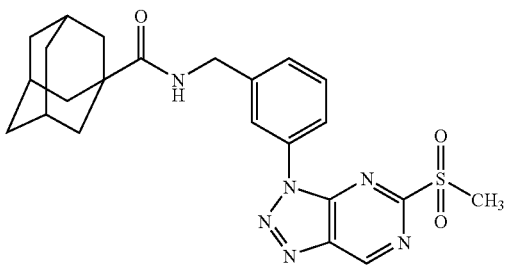

(0.0002 mol) and 3-aminobenzonitrie (0.0004 mol) in 2-methoxyethanol (2 ml) was stirred for at least 48 hours at 120° C. and then the crude mixture was purified by high-performance liquid chromatography. The product fractions were collected and the solvent was evaporated. The obtained residue was dissolved in EtOH and then the solvent was evaporated. Yield: 0.017 g of compound 231.

c). Preparation of Compound 3

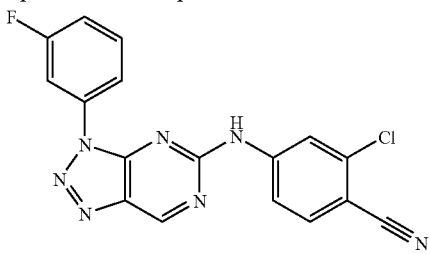

A mixture of 4-amino-2-chlorobenzonitrile (0.00034 mol) and NaH (0.00034 mol) in N,N-dimethylformamide (3 ml) was stirred at room temperature for 1 hour and intermediate 6 (0.00034 mol) was added, then the reaction mixture was stirred overnight at room temperature. H₂O and CH₃CN were added and the mixture was heated until complete dissolution, then stirred at room temperature for a few hours. The resulting precipitate was filtered off, washed and dried (vacuum). Yield: 0.0275 g of compound 3 (m.p.: >260 ° C.).

d). Preparation of Compound 57

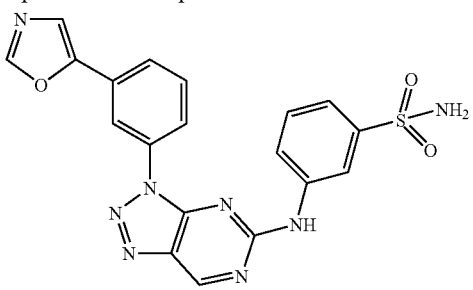

A mixture of intermediate 45

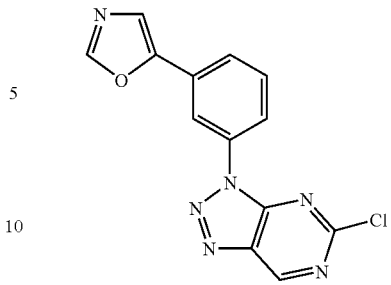

(prepared according to A2b.c) (0.0002 mol) and 3-aminobenzenesulfonamide (0.0004 mol) in 2-methoxyethanol (2 ml) was stirred for 1 hour at 100° C., then the reaction mixture was stirred in boiling CH₃CN (1 ml) with EtOH (1 ml) and the mixture was stirred overnight. The resulting precipitate was filtered off and dried. Yield: 0.043 g of compound 57 (49%, m.p.: >250° C.).

e). Preparation of Compound 249

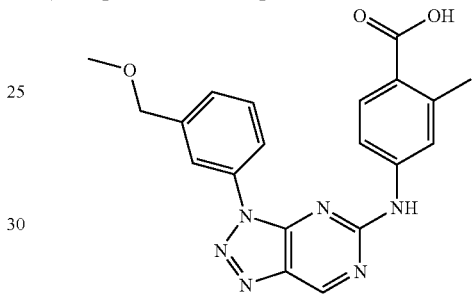

A mixture of intermediate 23 (prepared according to A2a.d) (0.0002 mol), 4-amino-2-methylbenzoic acid (0.0004 mol) and 2,6-dimethylpyridine (0.0006 mol) in DMF, p.a. (2 ml) was stirred for 20 hours at 60° C. and the solvent was evaporated. The residue was purified by high-performance liquid chromatography and then the desired fractions were collected. The solvent was evaporated and the residue was crystallised from H₂O, then the resulting precipitate was filtered off and dried. Yield: 0.011 g of compound 249.

EXAMPLE B2 a. Preparation of Compound 4

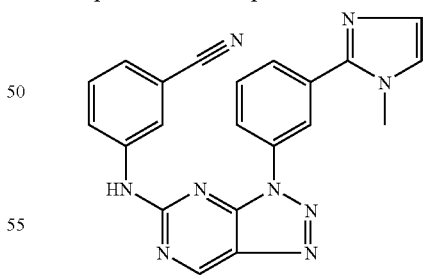

Intermediate 17 (prepared according to A7.b) (0.0127 mol) in HCl 6N (50 ml) was cooled to 0° C. Sodium nitrite (0.015 mol) in water (10 ml) was added dropwise. The mixture was stirred at room temperature for 18 hours; then neutralized with a NaOH solution. The formed precipitate was filtered off, washed and dried. This fraction was dissolved in MeOH/HCl/H₂O. The precipitate was filtered off. The filtrate was purified by high performance liquid chromatography over hyperprep C18 BDS (eluent: (0.5% NH₄OAc in H₂O/CH₃CN)/MeOH/CH₃CN 75/25/0; 0/50/50; 0/0/100). The desired fractions were collected and the solvent was evaporated. The residue was stirred in DIPE. The precipitate was filtered off, washed and dried (vacuum; 50° C.). Yield: 0.22 g of compound 4.

b. Preparation of Compound 5

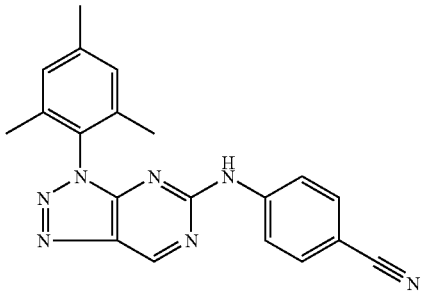

Sodium nitrite (0.00290 mol) was added to intermediate 18 (prepared according to A7.c) (0.00290 mol) in concentrated HCl (60 ml). The mixture was stirred at room temperature for 4 hours. The sample was cooled in an ice-bath and free based with solid NaOH. A solid was collected by filtration. This solid was air dried for 2.5 days. The sample was adsorbed onto silica gel (2.0 g) and purified by column chromatography (Biotage 40 M, eluent 10%, 50%, 60% EtOAc in hexanes). The desired fractions were rotary evaporated to a solid which was dried at room temperature in vacuo for 18 hours to yield 0.56 g of compound 5 (54%).

c. Preparation of Compound 6

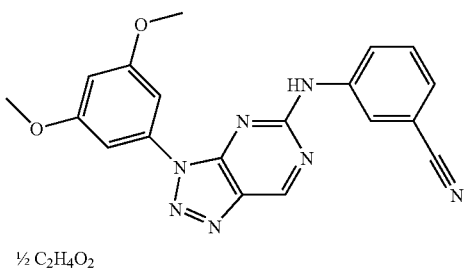

½ C₂H₄O₂

Intermediate 16 (prepared according to A7.a) (0.0008 mol) was stirred in HCl 6N (10 ml) and acetic acid (10 ml) at room temperature. A solution of sodium nitrite (0.0010 mol) in water (1 ml) was added dropwise and the reaction mixture was stirred for 1 hour. The precipitate was filtered off, washed with H₂O, with CH₃OH and with DIPE and then dried. Yield: 0.184 g of compound 6 (62%, m.p.: 228-232° C.).

d-1. Preparation of Compound 46

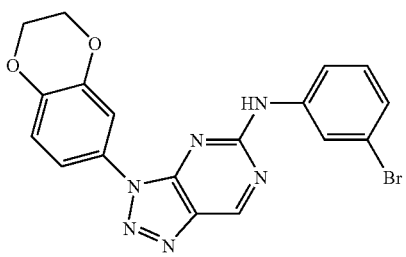

Intermediate 46

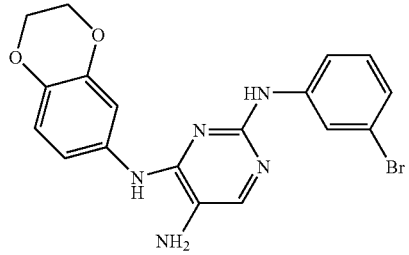

(prepared according to A7.a) (0.00022 mol) was suspended in HOAc (5 ml). HCl, 6N (1.1 ml; 30 equiv.) was added and the mixture was cooled to 0° C. A solution of NaNO₂ (0.000275 mol; 1.25 equiv.) in H₂O (0.5 ml) was added slowly, dropwise. The reaction mixture was stirred for 1 hour at 0° C., then for 1 hour at room temperature. The mixture was evaporated. The residue was triturated under water and some 2-propanone, filtered, washed with water on the funnel, then dried. Yield: 0.060 g of compound 46 (64%).

d-2). Preparation of Compound 7

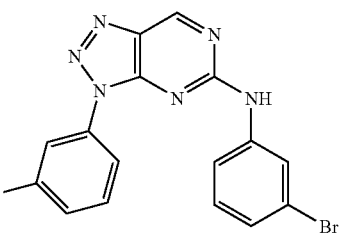

6N HCl (0.144 mol) was added to a solution of intermediate 47

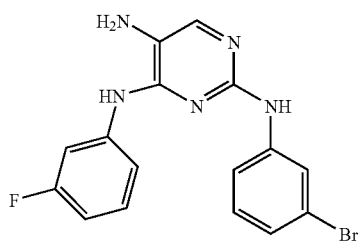

(prepared according to A7) (0.0048 mol) in acetic acid (24 ml) and the resulting thick suspension was cooled to 0° C., then a solution of NaNO₂ (0.006 mol) in H₂O (6 ml) was slowly added dropwise. Halfway through the addition, extra acetic acid (10 ml) and H₂O (10 ml) were added. Again extra acetic acid (70 ml) was added and after complete addition of the NaNO₂ solution, the reaction mixture was stirred for 1 hour at 0° C. and then stirred overnight at room temperature. The resulting solids were filtered off and washed with H₂O, then triturated on the funnel under 2-propanone/H₂O and washed with H₂O again. The crude solid (HCl-salt) was dissolved in DMF and a saturated NH₄OH solution (1 ml) was added to alkalise the solution. H₂O was added and the resulting precipitate was filtered off, then washed with H₂O and dried (vacuum). Yield: 1.67 g of compound 7 (90%, m.p.: 212-213° C.).

e). Preparation of Compound 298

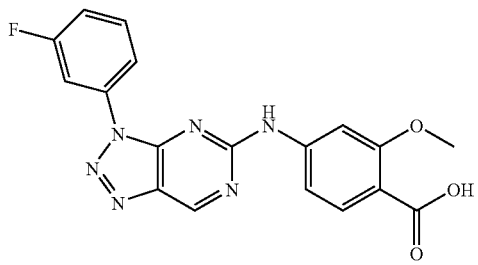

1N HCl (0.00027 mol) was added to a solution of intermediate 48

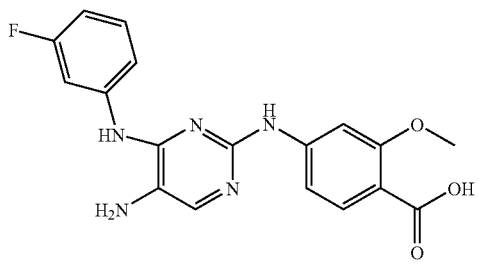

(prepared according to A2a.b) (0.00027 mol) in acetic acid (2.7 ml), then a mixture of NaNO$_2$ (0.0003 mol) in H$_2$O (0.30 ml) was added dropwise and the reaction mixture was stirred overnight at room temperature. The solvent was evaporated and the residue was purified by Biotage column chromatography (eluent gradient: CH$_2$Cl$_2$/CH$_3$OH 100/0 to 95/5). The product fractions were collected and the solvent was evaporated. The obtained residue was suspended in DIPE, filtered off, washed and dried (vacuum). Yield: 0.0020 g of compound 298 (m.p.: 232° C.).

EXAMPLE B3

Preparation of Compound 8

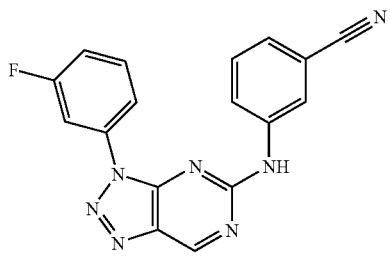

A mixture of compound 7 (prepared according to B2.d-2) (0.00052 mol), Pd$_2$(dba)$_3$ (0.025 g), 1,1'-bis(diphenylphosphino)ferrocene (0.033 g) and Zn+Zn (CN)$_2$ (0.012 g+0.105 g) in DMA (10 ml) was reacted according to the following procedure. The reaction mixture was reacted in a microwave for 15 minutes at 150 °C., then the mixture was filtered over dicalite and washed thoroughly with DMF. The solvent was evaporated and the residue was stirred in CH$_3$CN. The resulting precipitate was filtered off and dried. This fraction was purified over silica gel (eluent: CH$_2$Cl$_2$/CH$_3$OH 98/2). The product fractions were collected and the solvent was evaporated. The residue was stirred in DIPE/CH$_3$CN (1/1), then the resulting precipitate was filtered off and dried. Yield: 0.127 g of compound 8 (73%, m.p.: 228-230 °C.).

EXAMPLE B4 a). Preparation of Compound 9

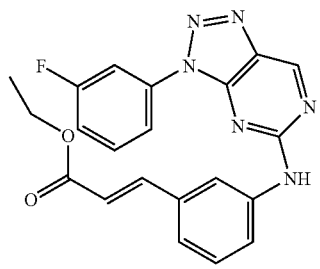

A mixture of compound 7 (prepared according to B2.d-2) (0.0013 mol), ethyl 2-propenoic acid ester (0.025 mol), Pd(OAc)$_2$ (0.0002 mol) and 1,3-bis(diphenylphosphino)propane (0.0004 mol) in Et$_3$N (3 ml) and THF (100 ml) was stirred for 16 hours in autoclave at 125° C., the solvent was evaporated and the residue was stirred in boiling CH$_3$CN. The precipitate was filtered off and dried. Yield: 0.374 g of compound 9 (71%, m.p.: 214-218.1° C.).

b). Preparation of Compound 10

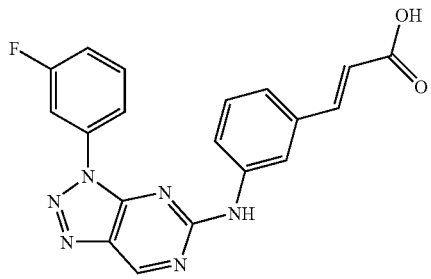

A mixture of compound 9 (prepared according to B4.a) (0.001 mol) and NaOH (1N) (0.015 mol) in THF, p.a. (35 ml) was stirred for 20 hours at room temperature, then the reaction mixture was stirred for 4 hours at 60° C. and the solution was stirred overnight at room temperature. The organic solvent (THF) was evaporated, the aqueous concentrate was diluted with H$_2$O (20 ml) and neutralised with HCl (15 ml, 1N). The mixture was stirred for a few hours and the resulting precipitate was filtered off. This fraction was taken up in H$_2$O/DMSO and NaOH (10 ml, 1N) was added, then the mixture was warmed until complete dissolution, filtered over a pleated paper filter and cooled. The residue was washed 5 times with EtOAc and the aqueous layer was neutralised with HCl (10 ml, 1N). The mixture was stirred overnight, then the resulting precipitate was filtered off and dried (vacuum). Yield: 0.202 g of compound 10 (54%, m.p.: >250° C.).

EXAMPLE B5 a) Preparation of Compound 12

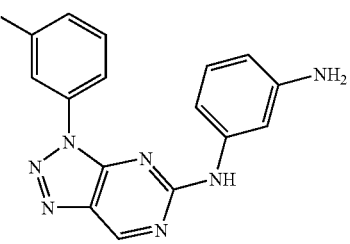

A mixture of

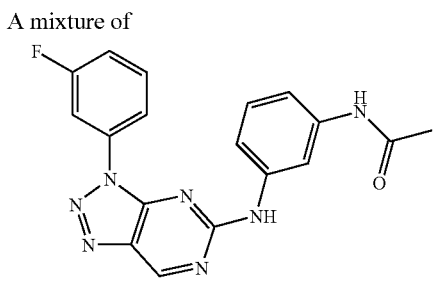

(compound 11 and prepared according to B1.b-2) (0.00019 mol) in HCl 12N (2 ml) and ethanol (3 ml) was stirred for 2 hours at 90° C., then the reaction mixture was cooled and the solvent was evaporated. The residue was crystallised from CH₃OH, the resulting precipitate was filtered off and dried. Yield: 0.027 g of compound 12 (m.p.: 224° C.).

b). Preparation of Compound 305

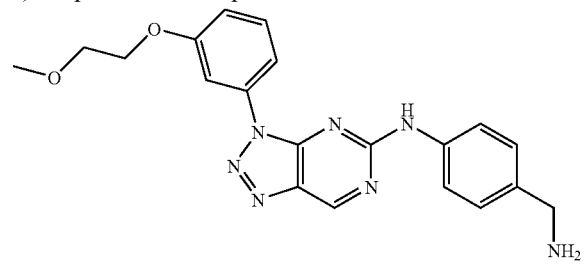

Compound 302 (prepared according to B1.b-2) (0.0002 mol) was added to 2-methoxyethanol (3 ml) and heated until complete dissolution, then HCl/2-propanol (few drops) was added to the solution and the reaction mixture was stirred for 2 hours at 80° C. After stirring overnight at room temperature, H₂O was added with a few drops of 1M NaOH. The resulting precipitate was filtered off, washed and dried (vacuum), yielding compound 305 (m.p.: 157° C.).

EXAMPLE B6

Preparation of Compound 69

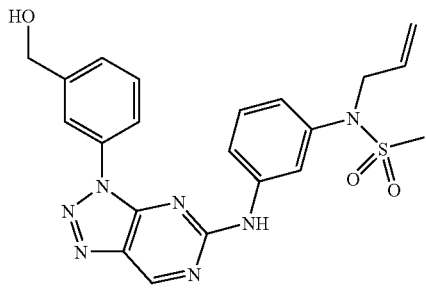

A mixture of compound 62 (prepared according to B1.b-2) (0.0003 mol) in DMF, p.a. (5 ml) was stirred and NaH (60%) (0.0003 mol) was added under N₂, then the mixture was stirred for 30 minutes at room temperature and a mixture of 3-bromo-1-propene (0.0003 mol) in DMF, p.a (1 ml) was added dropwise. The reaction mixture was stirred for 2 hours at room temperature, then the mixture was poured out into ice-water and extracted 3 times with CH₂Cl₂. The organic layer was dried (MgSO₄), filtered off and the solvent was evaporated. The residue was stirred in DIPE with a small amount of CH₃CN and the resulting precipitate was filtered off, then dried. The filtrate was evaporated and the residue was purified by column chromatography over silica gel (eluent: CH₂Cl₂/(CH₃OH/NH₃) 98/2). The product fractions were collected and the solvent was evaporated. The residue was crystallised from CH₃OH, then the resulting precipitate was filtered off and dried. Yield: 0.067 g of compound 69 (50%, m.p.: 158-162° C.)

EXAMPLE B7

Preparation of Compound 279

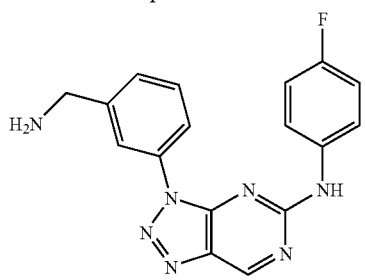

A mixture of compound 270 (prepared according to B1.b-1) (0.00015 mol) in 2-propanol/HCl (6M) (1 ml) and dioxane/HCl (4M) (3 ml) was stirred for 20 hours at room temperature, then the resulting precipitate was filtered off and dried, yielding compound 279.

EXAMPLE B8

Preparation of Compound 322 and 323 compound 322

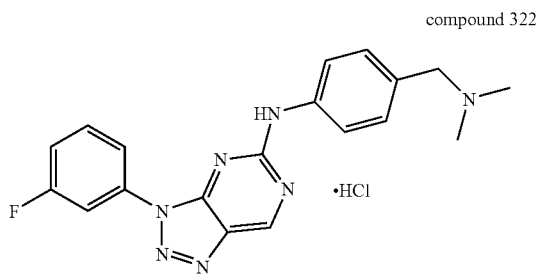

compound 323

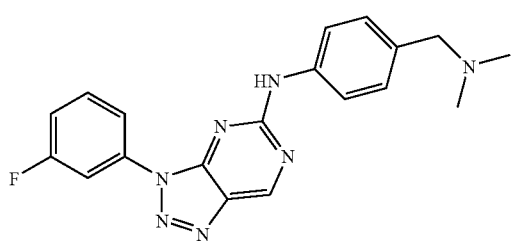

Compound 295 (prepared according to B5.b) was taken up into (a minimal amount of water)/CH₃OH/KOAc. This mixture was extracted with CH₂Cl₂. The organic layer was separated, washed with 80% NaHCO₃/H₂O, dried (MgSO₄), filtered and the solvent was evaporated to give free base residue A*. A mixture of A* (0.000388 mol) and poly(oxymethylene) (0.2 g) in methanol (50 ml) was hydrogenated at 50° C. for 16 hours with Pd/C 10% (0.1 g) as a catalyst in the presence of thiophene solution, 4% in DIPE (0.1 ml). After uptake of H₂ (2 equivalents), the catalyst was filtered off and the solvent was evaporated. The residue was dissolved in CH₂Cl₂ (100 ml) and washed with an 80% saturated Na₂CO₃ solution (aqueous), then dried (MgSO₄) and the crude product was purified by flash chromatography on Redisep cartridge. The product fractions were collected and the solvent was evaporated. The residue was triturated under CH₃CN/DIPE and the desired fractions were collected. Yield: Fraction 1: final compound 323 (m.p.: 192-196° C.). Yield: Fraction 2: 0.061 g of final compound 322 (39%).

EXAMPLE B9

Preparation of Compound 76

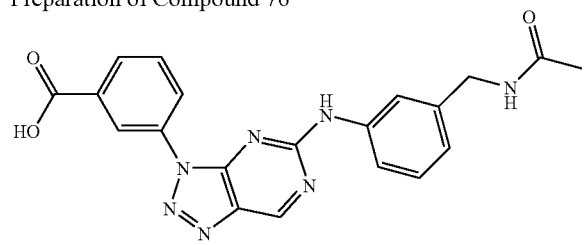

A mixture of compound 74 (prepared according to B1.b-1) (0.00016 mol) and NaOH (1N, p.a.) (0.0005 mol) in dioxane, p.a. (3.5 ml) and DMSO, p.a. (0.5 ml) was stirred for 24 hours at room temperature and the solvent was evaporated, then the residue was stirred in $H_2O$ and the mixture was neutralised with HCl (1N, 0.5 ml). The resulting precipitate was filtered off and dried. Yield: 0.013 g of compound 76 (20%, m.p.: >260° C.).

Table 1 lists the compounds that were prepared according to one of the above Examples.

TABLE 1

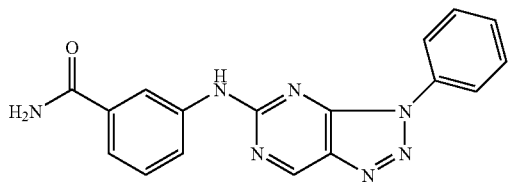

Co. No. 38; Ex. B2c;

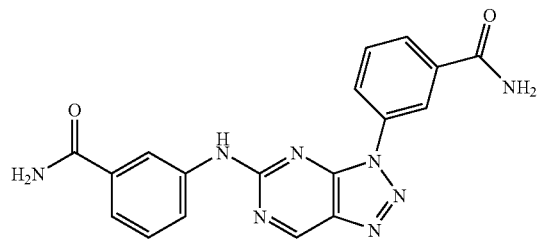

Co. No. 39; Ex. B2c;

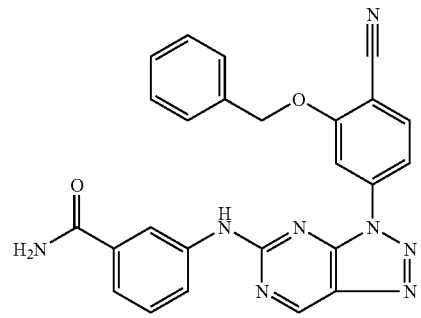

Co. No. 40; Ex. B2c;

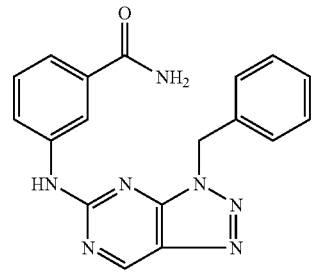

Co. No. 41; Ex. B2c;

TABLE 1-continued
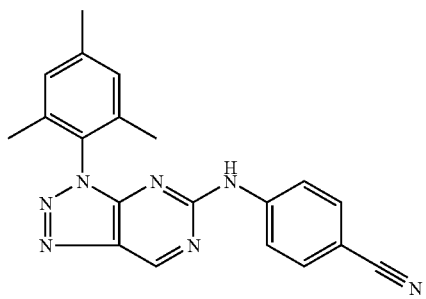
Co. No. 5; Ex. B2b;
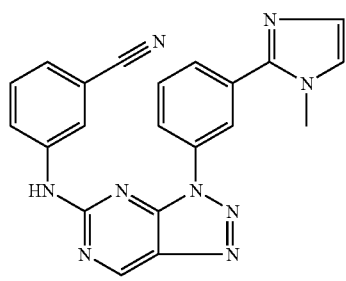
Co. No. 4; Ex. B2a;
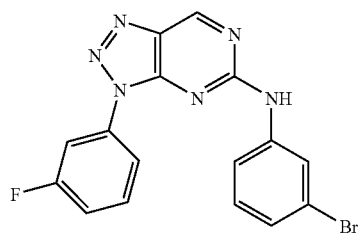
Co. No. 7; Ex. B2d-2; mp. 212° C.;
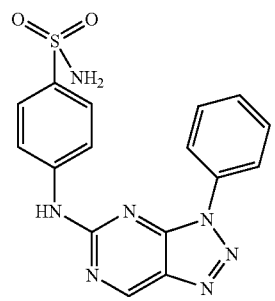
Co. No. 37; Ex. B2c; mp. 286° C.;

TABLE 1-continued
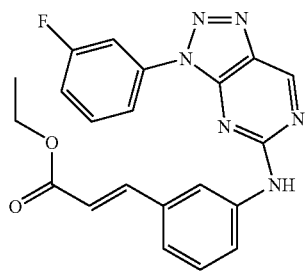
Co. No. 9; Ex. B4a; mp. 214° C.;
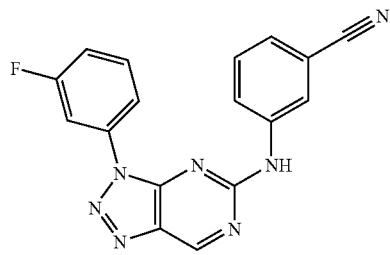
Co. No. 8; Ex. B3; mp. 228° C.;
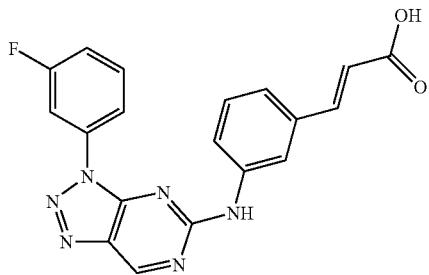
Co. No. 10; Ex. B4b; mp. >250° C.;
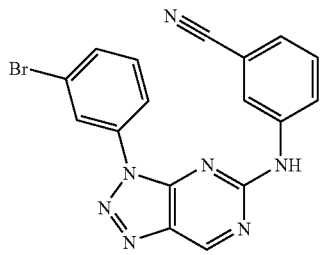
Co. No. 33; Ex. B1a-1; mp. 252° C.;
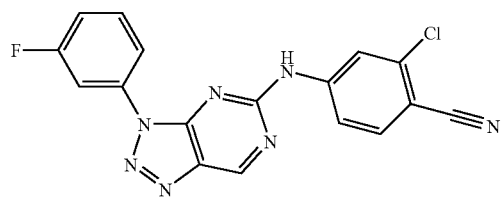
Co. No. 3; Ex. B1c; mp. >260° C.;

TABLE 1-continued
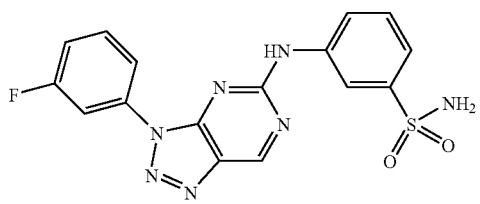
Co. No. 1; Ex. B1a-1; mp. 177° C.;
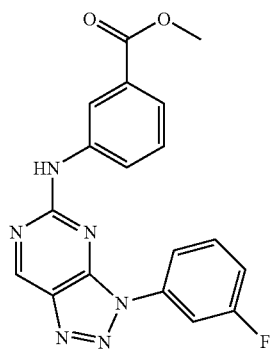
Co. No. 13; Ex. B1a-2;
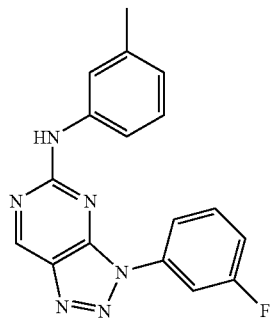
Co. No. 14; Ex. B1a-2;
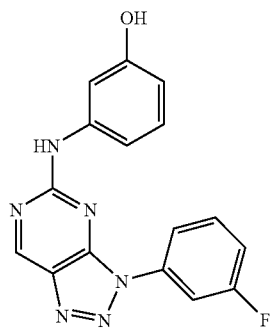
Co. No. 15; Ex. B1a-2; mp. >260° C.;

TABLE 1-continued
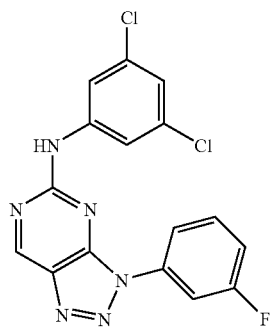
Co. No. 16; Ex. B1a-2;
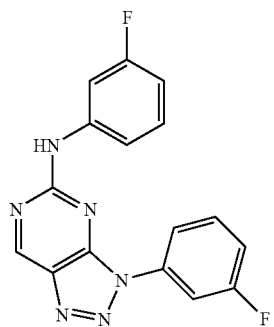
Co. No. 17; Ex. B1a-2; mp. 192° C.;
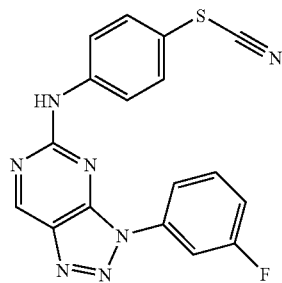
Co. No. 18; Ex. B1a-2;
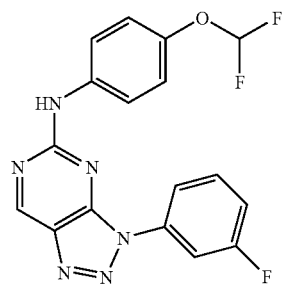
Co. No. 19; Ex. B1a-2;

TABLE 1-continued
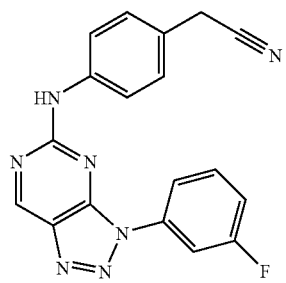
Co. No. 20; Ex. B1a-2;
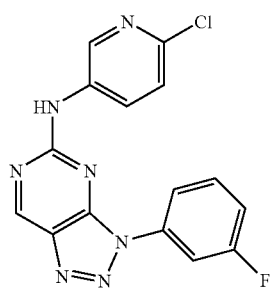
Co. No. 32; Ex. B1a-2;
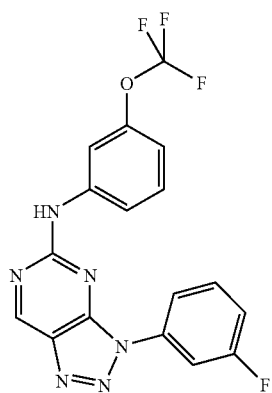
Co. No. 22; Ex. B1a-2;
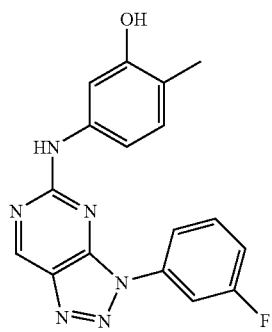
Co. No. 21; Ex. B1a-2; mp. 174° C.;

TABLE 1-continued
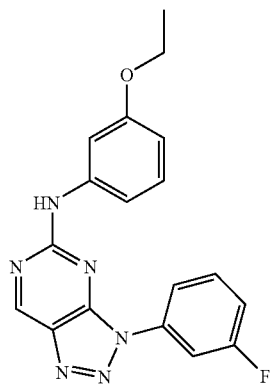
Co. No. 23; Ex. B1a-2; mp. 167° C.;
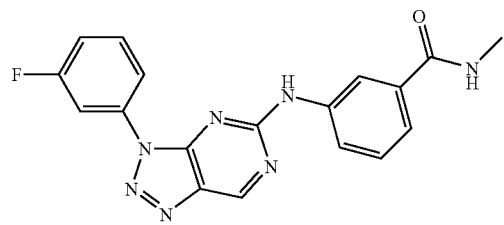
Co. No. 24; Ex. B1a-1;
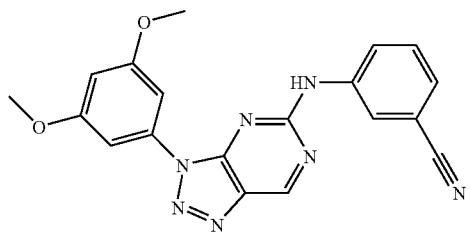
Co. No. 6; Ex. B2c; mp. 228° C.;
.0.5$C_2H_4O_2$
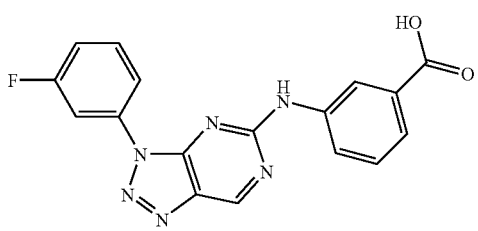
Co. No. 29; Ex. B1a-1/B1b-1; mp. >260° C.;
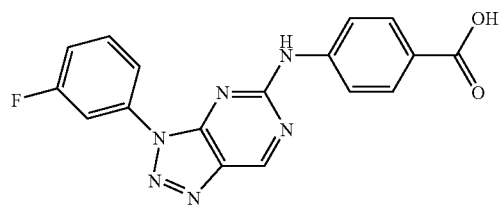
Co. No. 30; Ex. B1a-1; mp. >260° C.;

TABLE 1-continued
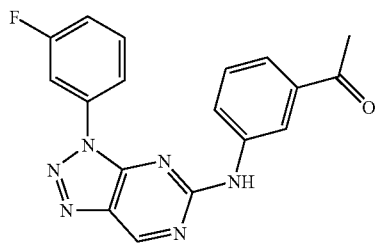
Co. No. 2; Ex. B1b-1; mp. 220° C.;
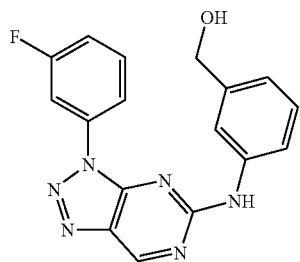
Co. No. 31; Ex. B1a-1/B1b-1; mp. 188° C.;
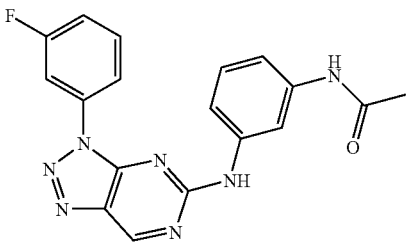
Co. No. 11; Ex. B1b-2; mp. 238° C.
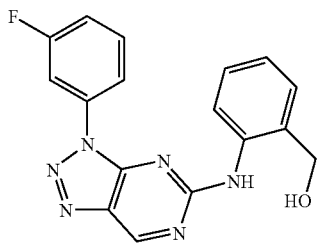
Co. No. 26; Ex. B1b-3; mp. 232° C.
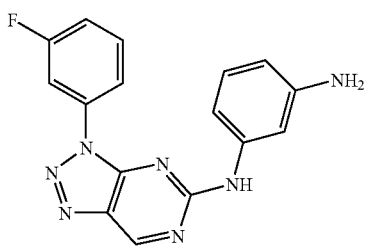
Co. No. 12; Ex. B5; mp. 222° C. .HCl TABLE 1-continued
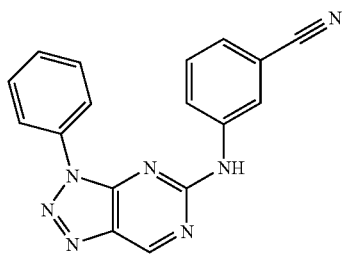
Co. No. 34; Ex. B2c; mp. 190° C.
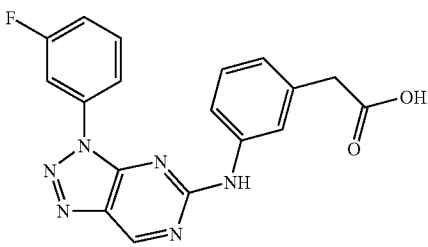
Co. No. 25; Ex. B1b-1; mp. 238° C.
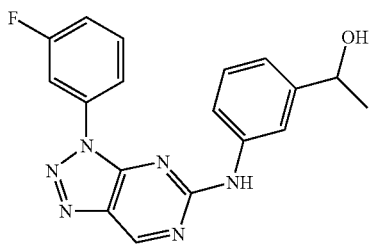
Co. No. 27; Ex. B1b-4; mp. 150° C.
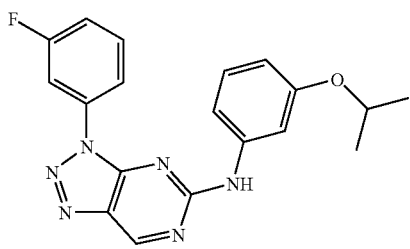
Co. No. 28; Ex. B1b-5; mp. 142° C.
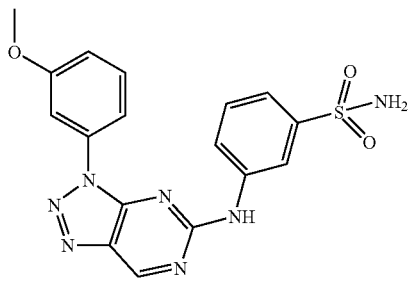
Co. No. 35; Ex. B1b-4; mp. 220° C.

TABLE 1-continued
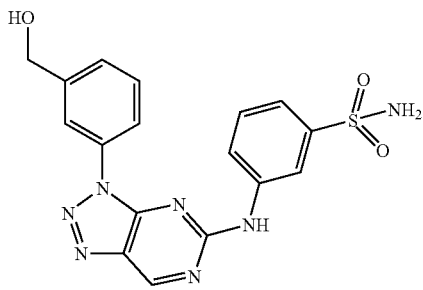
Co. No. 36; Ex. B2c; mp. 222° C.
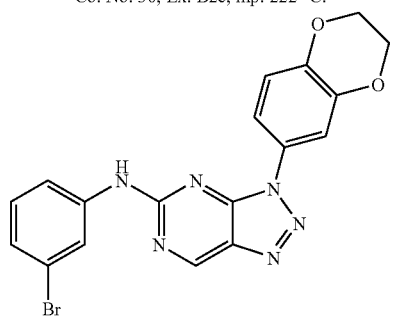
Co. No. 46; Ex. B2d;
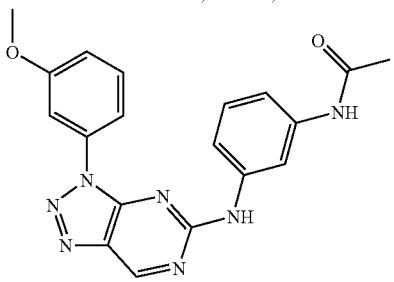
Co. No. 42; Ex. B1b-4; mp. 214° C.
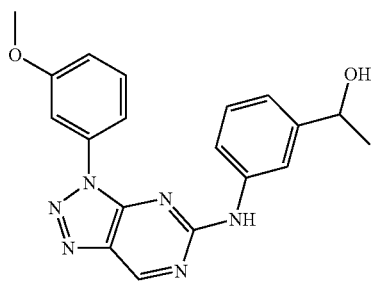
Co. No. 43; Ex. B1b-4; mp. 126° C.
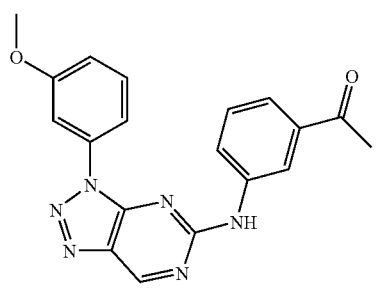
Co. No. 51; Ex. B1b-4; mp. 186° C.

TABLE 1-continued
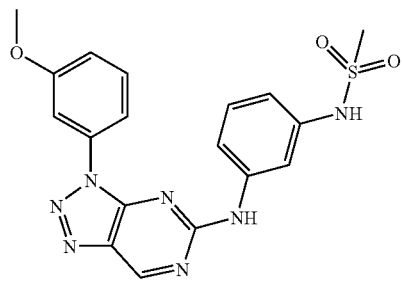
Co. No. 52; Ex. B1b-4; mp. 214° C.
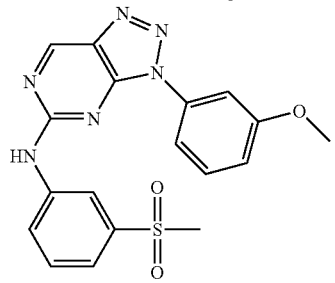
Co. No. 53; Ex. B1b-4; mp. 212° C.
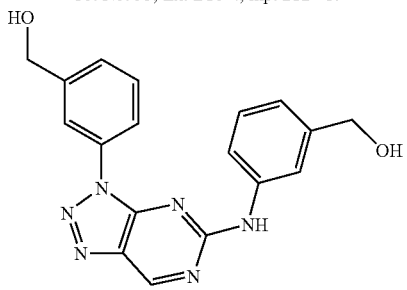
Co. No. 54; Ex. B2c; mp. 172° C.
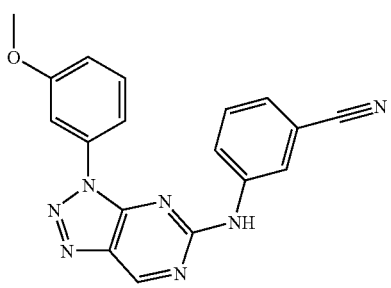
Co. No. 55; Ex. B1b-6; mp. 228° C.
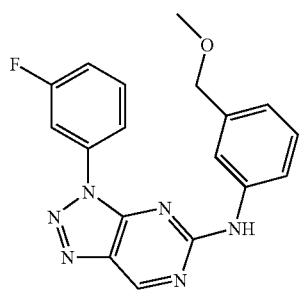
Co. No. 56; Ex. B1b-2; mp. 160° C.

TABLE 1-continued
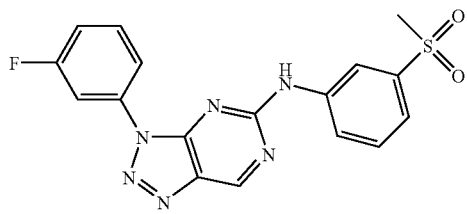
Co. No. 44; Ex. B1b-1; mp. 216° C.
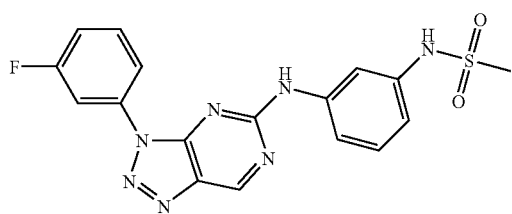
Co. No. 45; Ex. B1a-1; mp. 216° C.
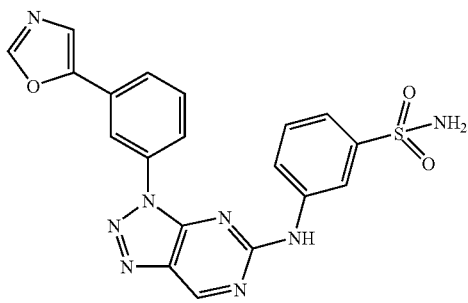
Co. No. 57; Ex. B1d; mp. >260° C.
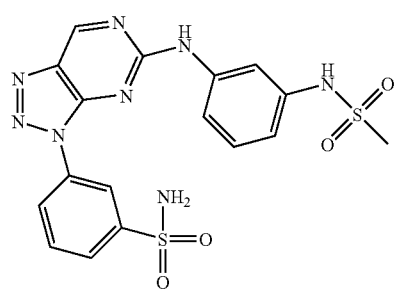
Co. No. 58; Ex. B1b-2; mp. 263° C.
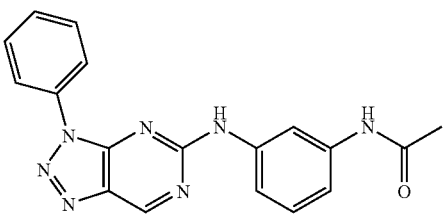
Co. No. 59; Ex. B1b-1; mp. 250° C.

TABLE 1-continued
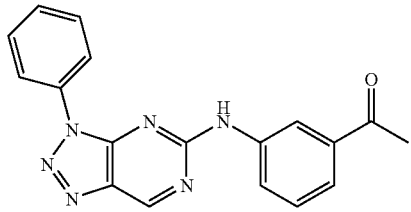
Co. No. 60; Ex. B1b-4; mp. 186° C.
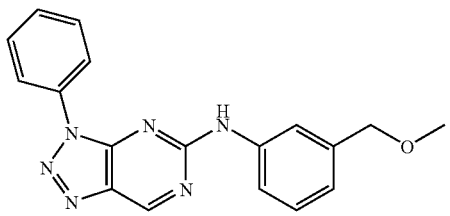
Co. No. 61; Ex. B1b-4; mp. 140° C.
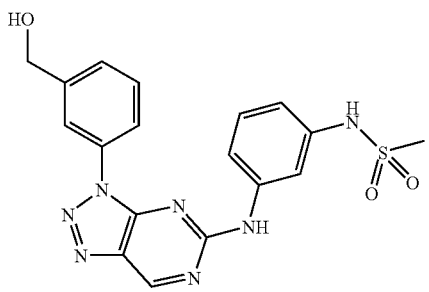
Co. No. 62; Ex. B1b-3; mp. 178° C.
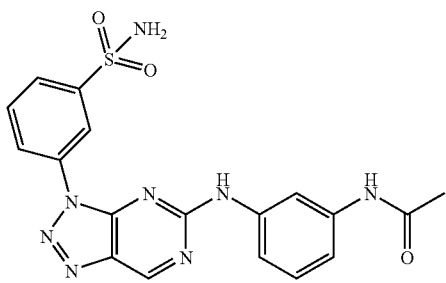
Co. No. 63; Ex. B1b-1; mp. 251° C.
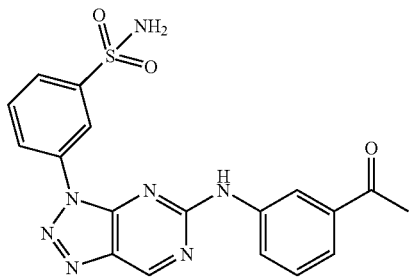
Co. No. 64; Ex. B1b-4; mp. 185° C.

TABLE 1-continued
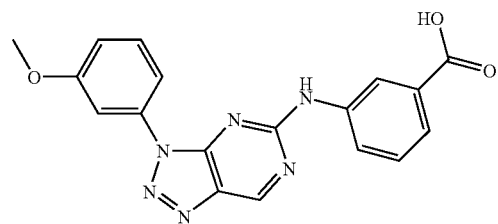
Co. No. 66; Ex. B1b-1; mp. >260° C.
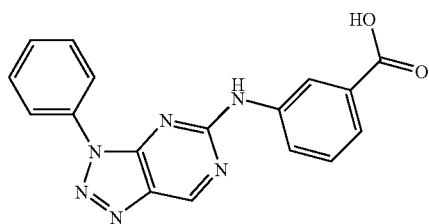
Co. No. 67; Ex. B1b-1; mp. >260° C.
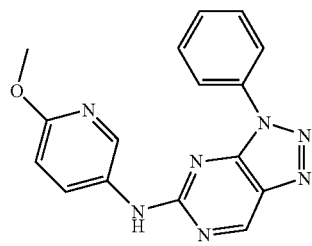
Co. No. 47; Ex. B1b-1; mp. 202° C.
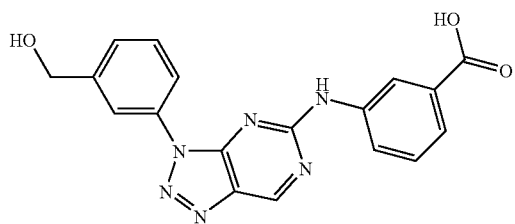
Co. No. 68; Ex. B1b-2; mp. 256° C.
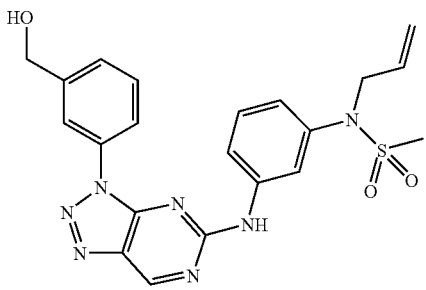
Co. No. 69; Ex. B6; mp. 158° C.

TABLE 1-continued
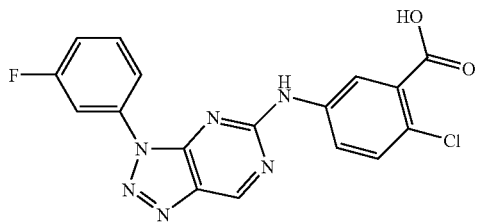
Co. No. 70; Ex. B1b-1; mp. >260° C.
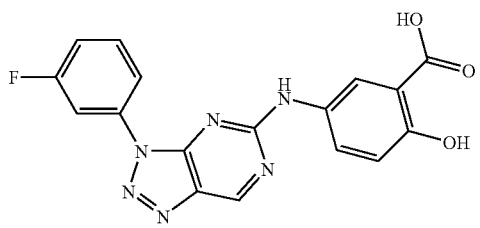
Co. No. 71; Ex. B1b-2; mp. >260° C.
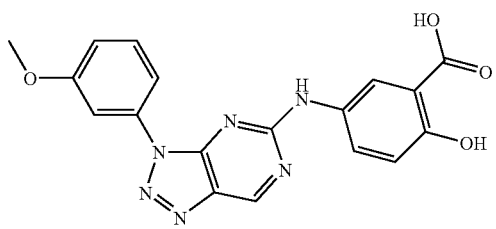
Co. No. 72; Ex. B1b-1; mp. >260° C.
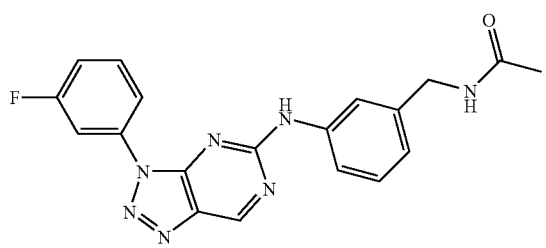
Co. No. 73; Ex. B1b-2; mp. 204° C.
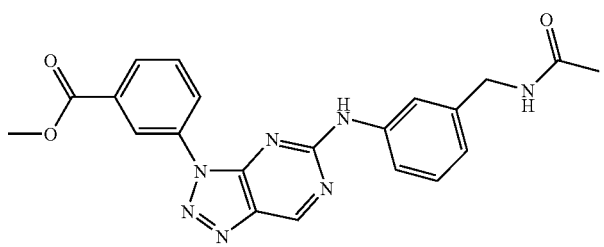
Co. No. 74; Ex. B1b-1; mp. 224° C.

TABLE 1-continued
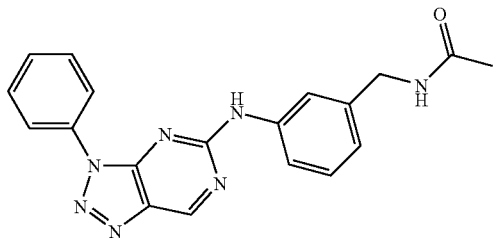
Co. No. 75; Ex. B1b-2; mp. 212° C.
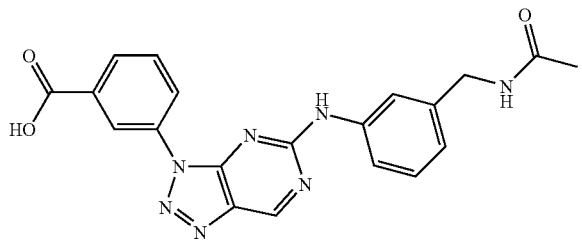
Co. No. 76; Ex. B9; mp. >260° C.
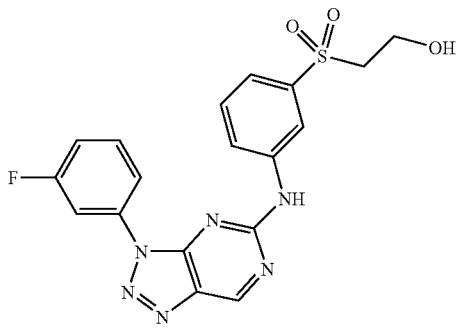
Co. No. 77; Ex. B1b-4; mp. 210° C.
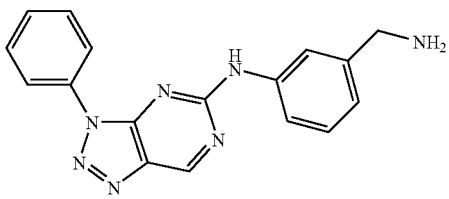
Co. No. 78; Ex. B5a; mp. >260° C.
.HCl
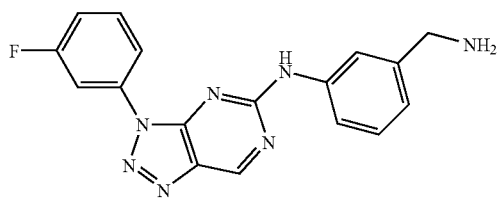
Co. No. 79; Ex. B5a; mp. >260° C.
.HCl TABLE 1-continued
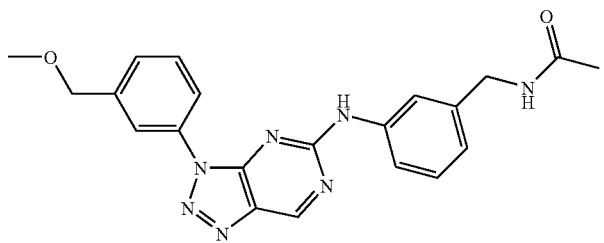
Co. No. 80; Ex. B1b-4; mp. 154° C.
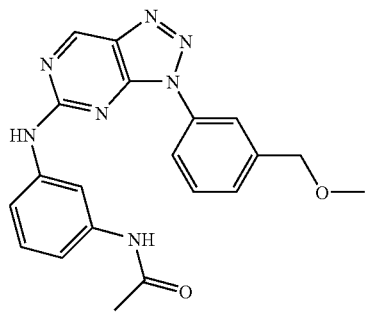
Co. No. 81; Ex. B1b-4; mp. 184° C.
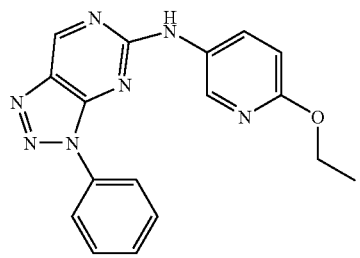
Co. No. 82; Ex. B1b-2; mp. 190° C.
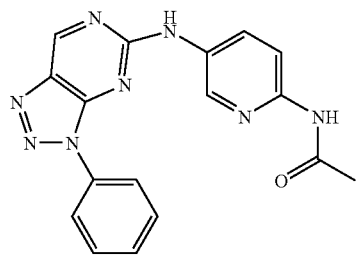
Co. No. 83; Ex. B1b-2; mp. 234° C.
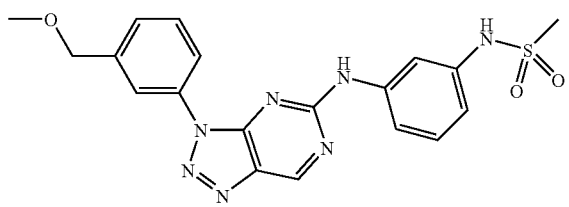
Co. No. 84; Ex. B1b-3; mp. 174° C.

TABLE 1-continued
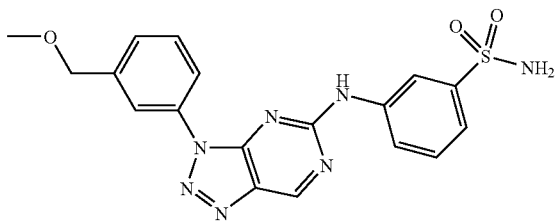
Co. No. 85; Ex. B1b-4; mp. 198° C.
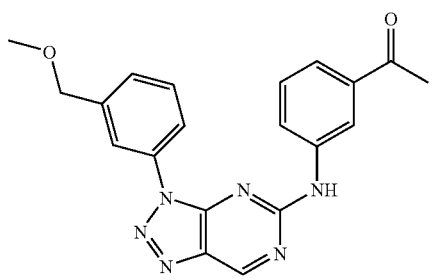
Co. No. 86; Ex. B1b-3; mp. 138° C.
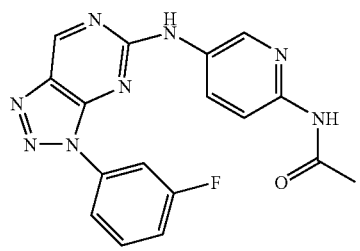
Co. No. 87; Ex. B1b-2; mp. >260° C.
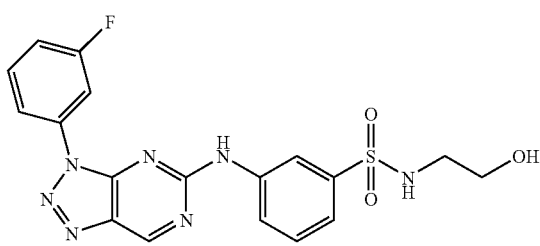
Co. No. 88; Ex. B1b-2; mp. 209° C.
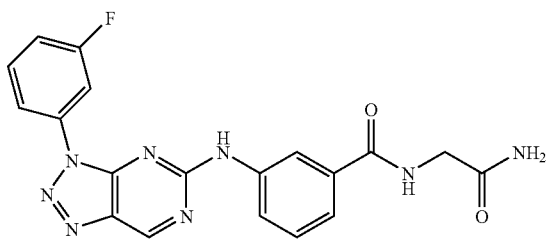
Co. No. 89; Ex. B1b-2; mp. >260° C.

TABLE 1-continued
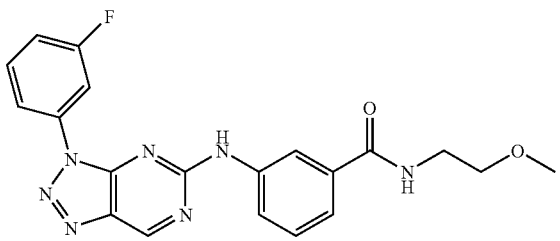
Co. No. 90; Ex. B1b-2; mp. 205° C.
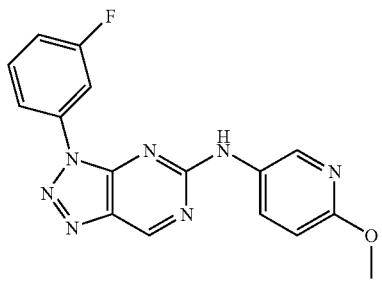
Co. No. 91; Ex. B1b-2; mp. 180° C.
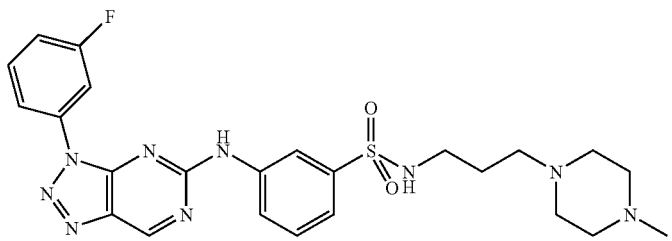
Co. No. 92; Ex. B1b-2; mp. 119° C.
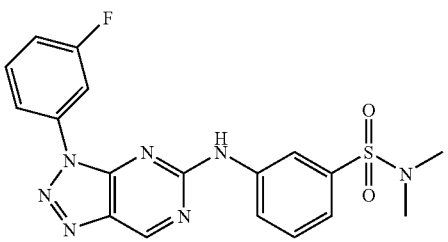
Co. No. 94; Ex. B1b-2; mp. 200° C.
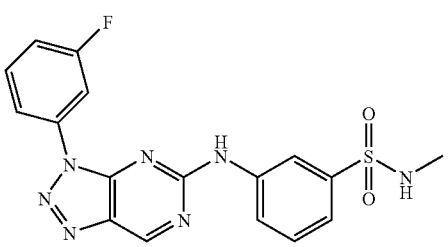
Co. No. 95; Ex. B1b-2; mp. 236° C.

TABLE 1-continued
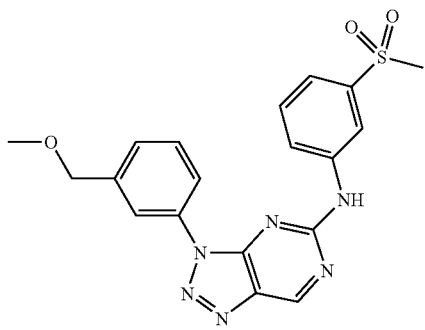
Co. No. 96; Ex. B1b-3; mp. 178° C.
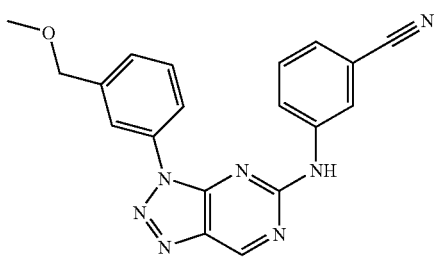
Co. No. 97; Ex. B1b-3; mp. 174° C.
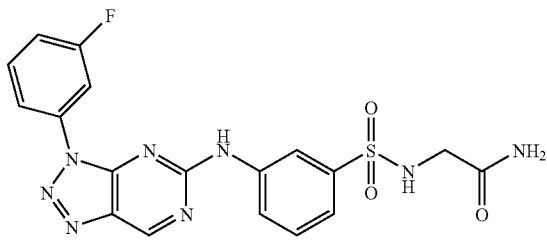
Co. No. 98; Ex. B1b-2; mp. 262° C.
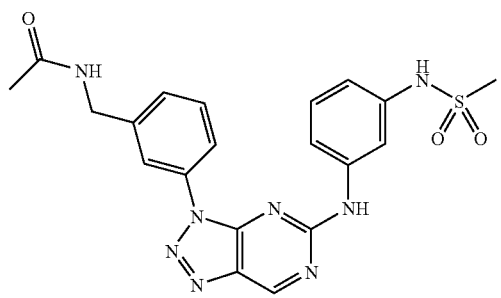
Co. No. 99; Ex. B1b-4; mp. 208° C.
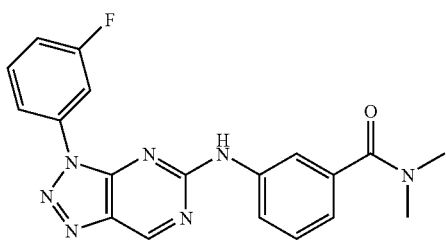
Co. No. 100; Ex. B1b-2; mp. 198° C.

TABLE 1-continued
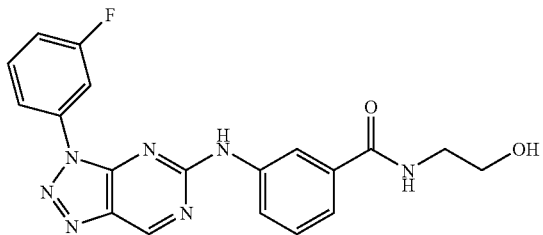
Co. No. 101; Ex. B1b-2; mp. 222° C.
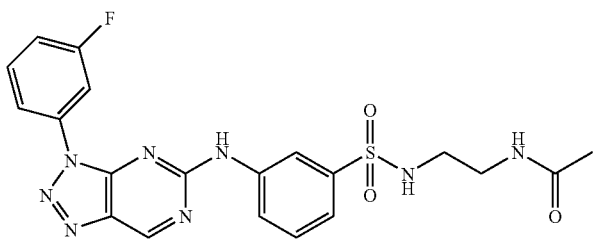
Co. No. 102; Ex. B1b-2; mp. 247° C.
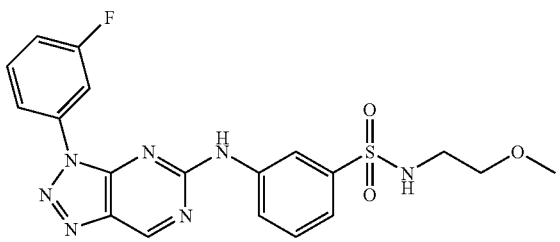
Co. No. 103; Ex. B1b-2; mp. 196° C.
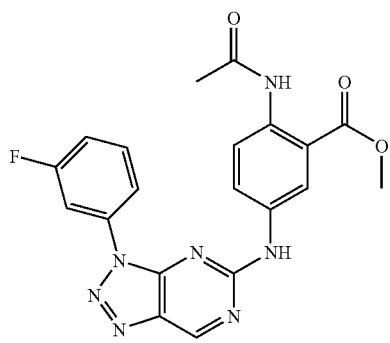
Co. No. 104; Ex. B1b-1; mp. >260° C.
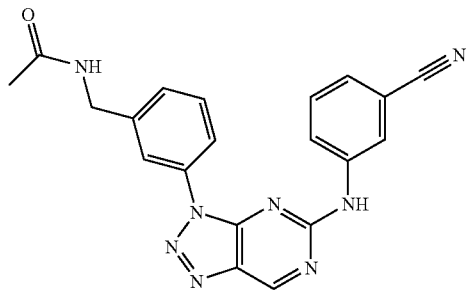
Co. No. 107; Ex. B1b-2; mp. 238° C.

TABLE 1-continued
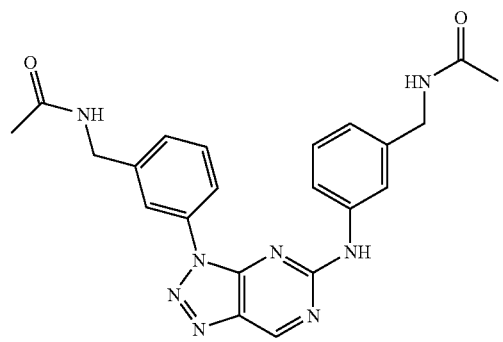
Co. No. 108; Ex. B1b-2; mp. 212° C.
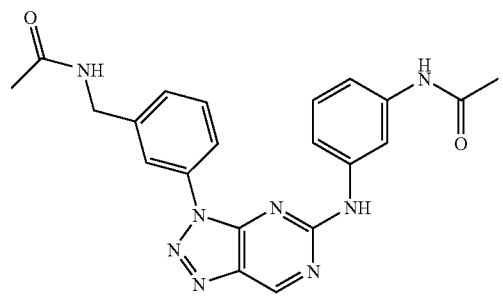
Co. No. 109; Ex. B1b-2; mp. >260° C.
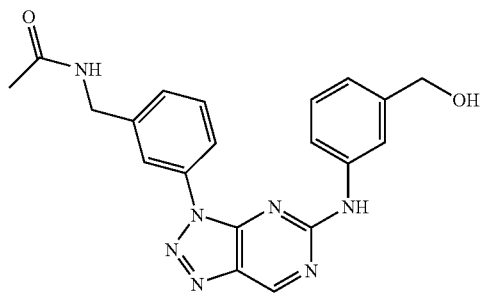
Co. No. 110; Ex. B1b-2; mp. 224° C.
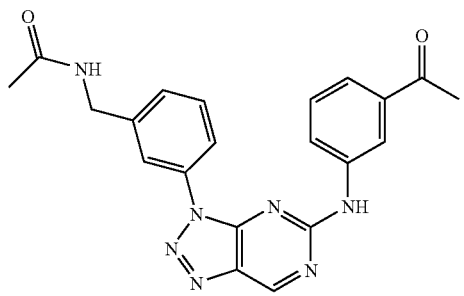
Co. No. 111; Ex. B1b-2; mp. 226° C.

TABLE 1-continued
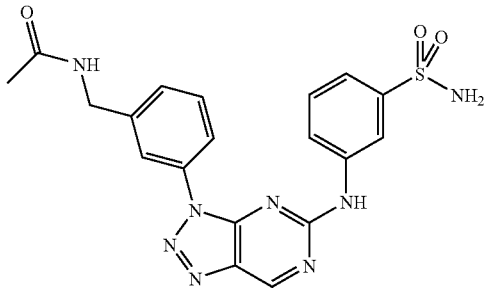
Co. No. 112; Ex. B1b-2; mp. 240° C.
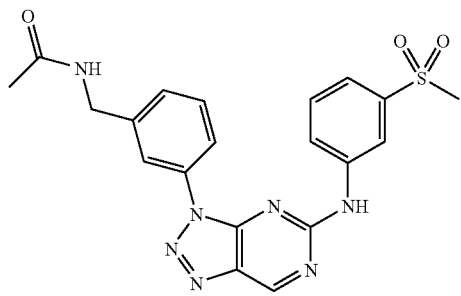
Co. No. 113; Ex. B1b-2; mp. 190° C.
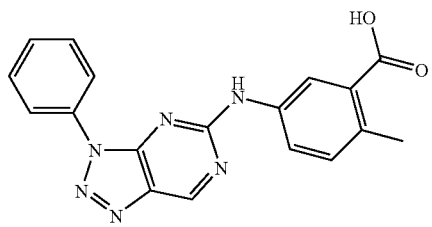
Co. No. 114; Ex. B1b-1; mp. >280° C.
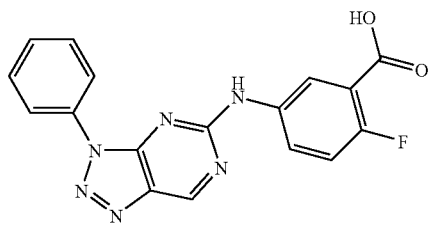
Co. No. 115; Ex. B1b-1; mp. >280° C.
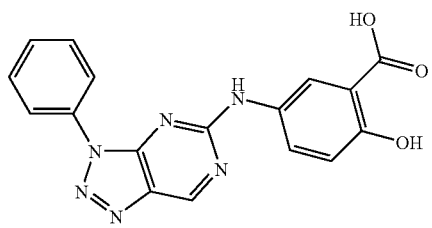
Co. No. 116; Ex. B1b-1; mp. >280° C.

TABLE 1-continued
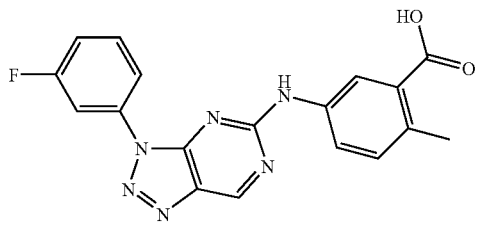
Co. No. 117; Ex. B1b-1; mp. >280° C.
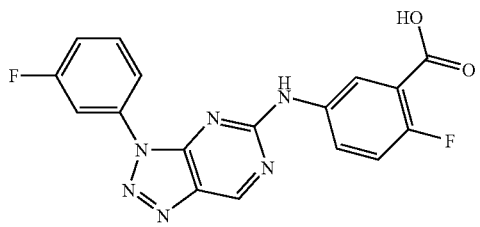
Co. No. 118; Ex. B1b-1; mp. >280° C.
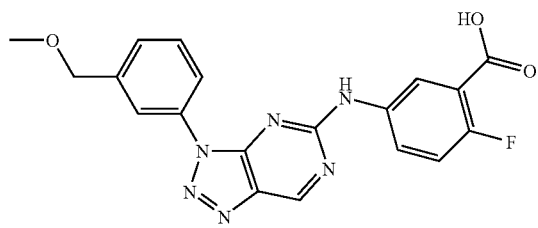
Co. No. 119; Ex. B1b-1; mp. 266° C.
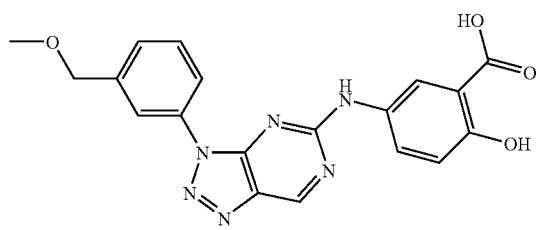
Co. No. 120; Ex. B1b-1; mp. >280° C.
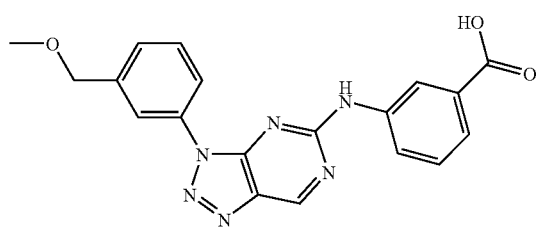
Co. No. 121; Ex. B1b-1; mp. 226° C.
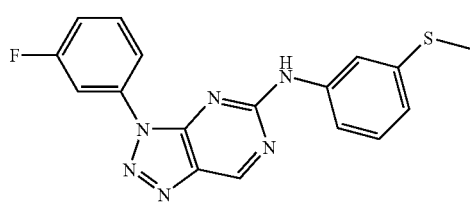
Co. No. 122; Ex. B1b-1; mp. 186° C.

TABLE 1-continued
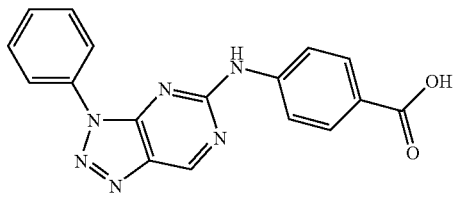
Co. No. 123; Ex. B1b-1; mp. >280° C.
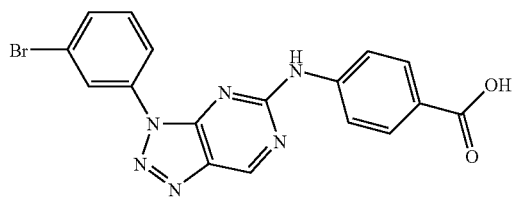
Co. No. 124; Ex. B1b-1; mp. >280° C.
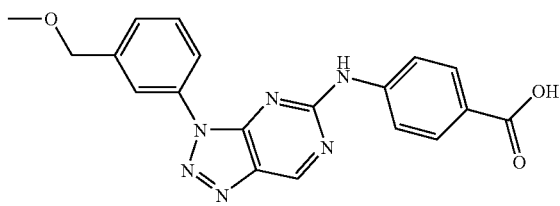
Co. No. 125; Ex. B1b-1; mp. >280° C.
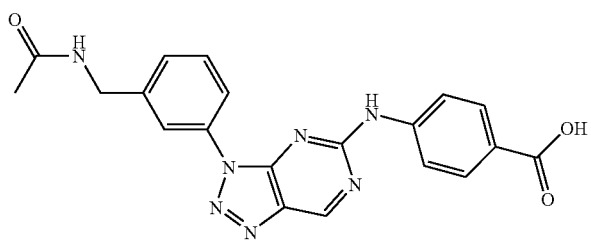
Co. No. 126; Ex. B1b-1; mp. >280° C.
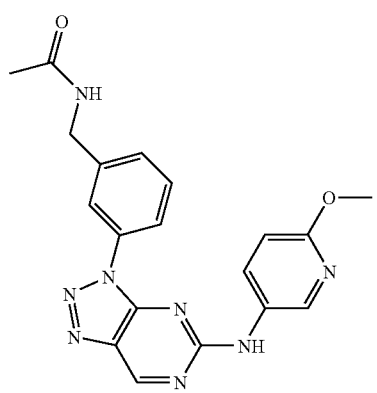
Co. No. 127; Ex. B1b-1; mp. 234° C.

TABLE 1-continued
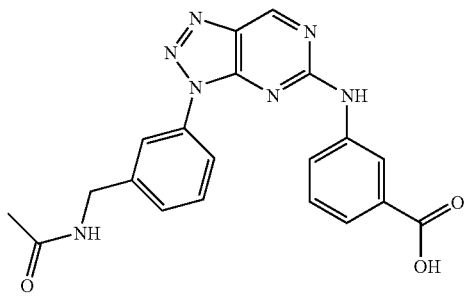
Co. No. 128; Ex. B1b-1; mp. 266° C.
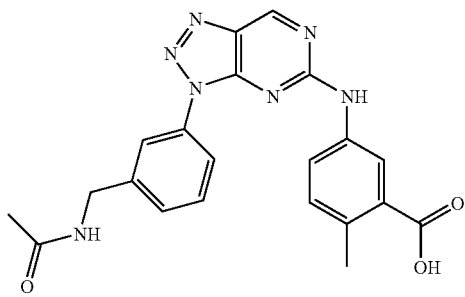
Co. No. 129; Ex. B1b-1; mp. 260° C.
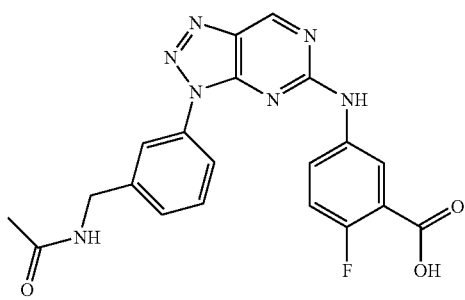
Co. No. 130; Ex. B1b-1; mp. 250° C.
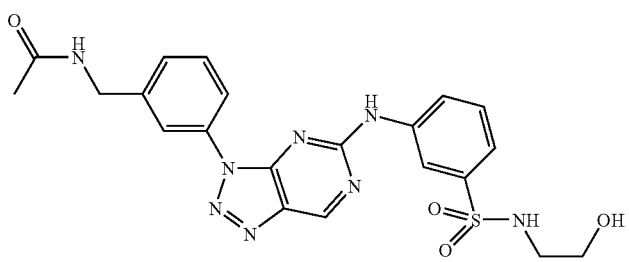
Co. No. 131; Ex. B1b-1; mp. 230° C.
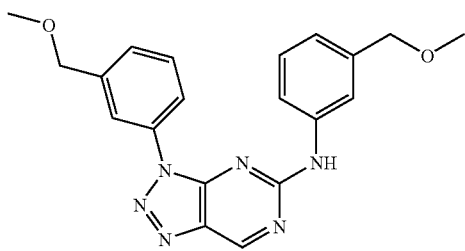
Co. No. 132; Ex. B1b-2; mp. 120° C.

TABLE 1-continued
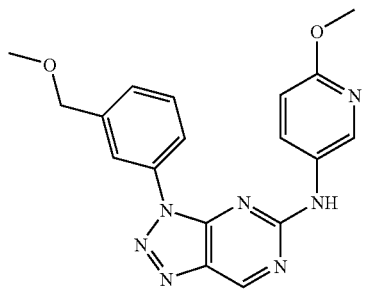
Co. No. 133; Ex. B1b-2; mp. 168° C.
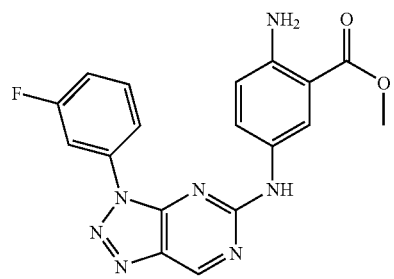
Co. No. 134; Ex. B1b-1; mp. 228° C.
.0.5H₂O.1.4HCl
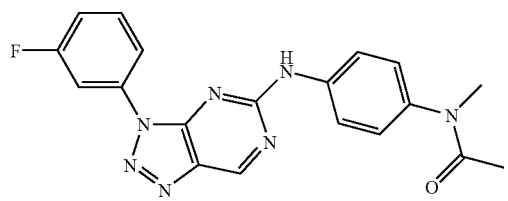
Co. No. 135; Ex. B1b-1; mp. 248° C.
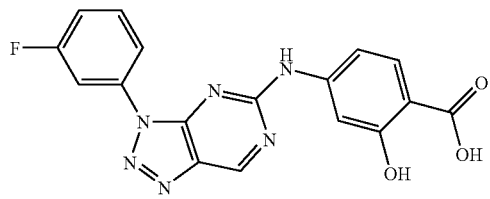
Co. No. 136; Ex. B1b-1; mp. >280° C.
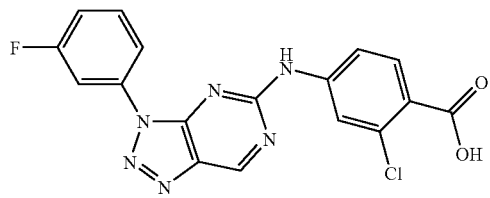
Co. No. 137; Ex. B1b-1; mp. >280° C.

TABLE 1-continued
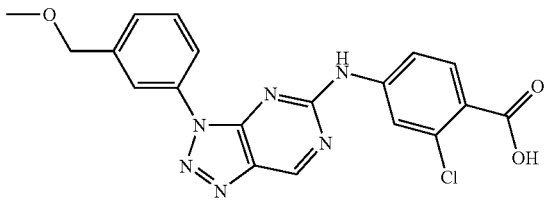
Co. No. 138; Ex. B1b-1; mp. >270° C.
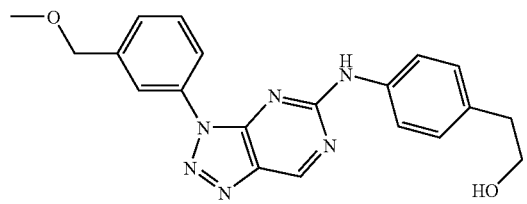
Co. No. 139; Ex. B1b-1; mp. 170° C.
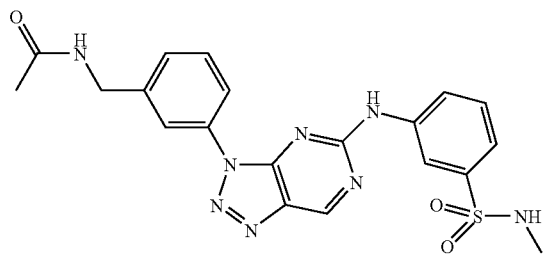
Co. No. 140; Ex. B1b-1; mp. 230° C.
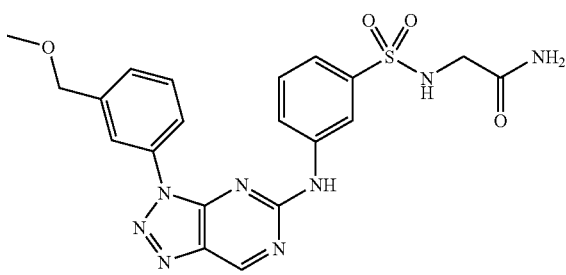
Co. No. 141; Ex. B1b-2; mp. 224° C.
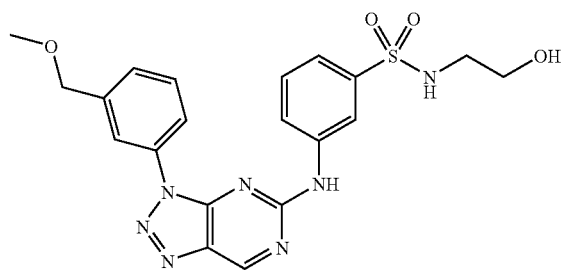
Co. No. 142; Ex. B1b-2; mp. 174° C.

TABLE 1-continued
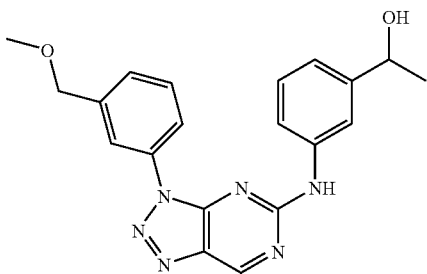
Co. No. 143; Ex. B1b-2; mp. 118° C.
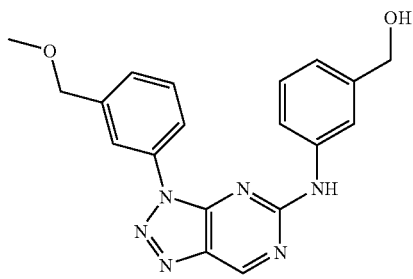
Co. No. 144; Ex. B1b-2; mp. 112° C.
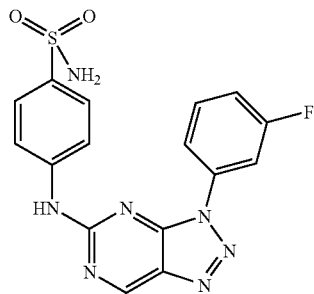
Co. No. 145; Ex. B1b-1; mp. 270° C.
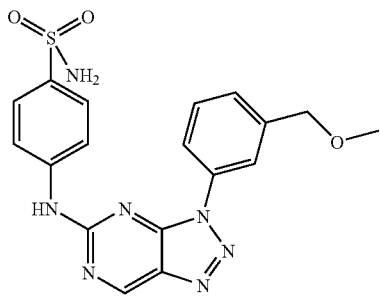
Co. No. 146; Ex. B1b-1; mp. 194° C.

TABLE 1-continued
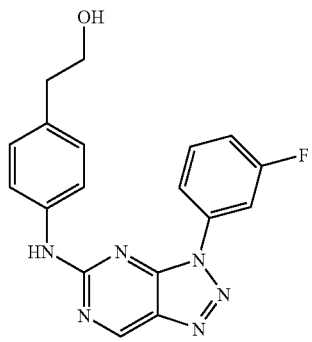
Co. No. 147; Ex. B1b-1; mp. 196° C.
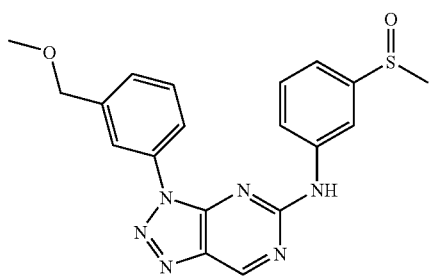
Co. No. 148; Ex. B1b-7a; mp. 142° C.
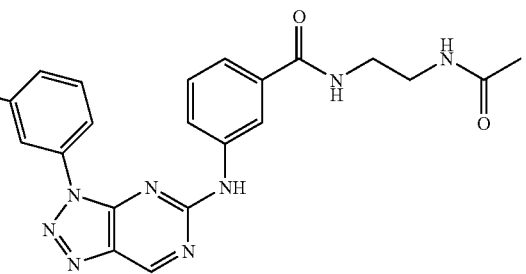
Co. No. 149; Ex. B1b-2; mp. 210° C.
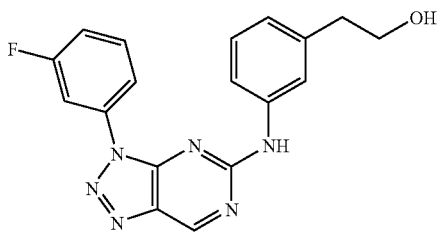
Co. No. 150; Ex. B1b-2; mp. 148° C.
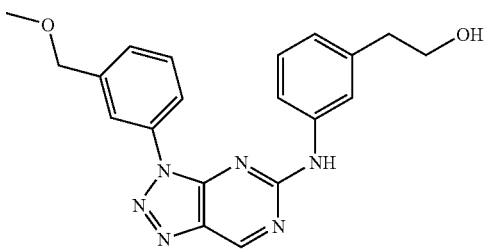
Co. No. 151; Ex. B1b-2; mp. 120° C.

TABLE 1-continued
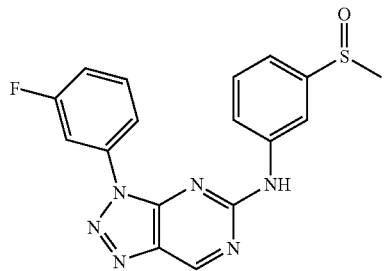
Co. No. 152; Ex. B1b-7b; mp. 168° C.
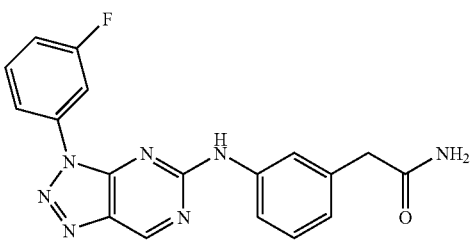
Co. No. 153; Ex. B1b-2; mp. 232° C.
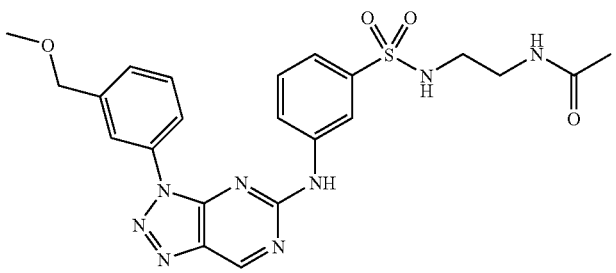
Co. No. 154; Ex. B1b-2; mp. 202° C.
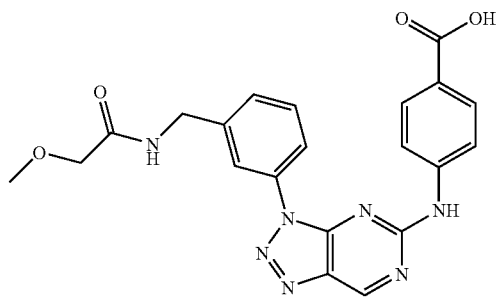
Co. No. 155; Ex. B1b-1; mp. >260° C.
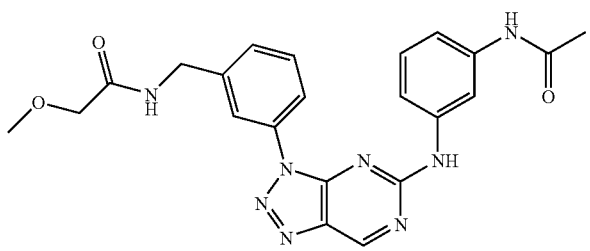
Co. No. 156; Ex. B1b-4; mp. 212° C.

TABLE 1-continued
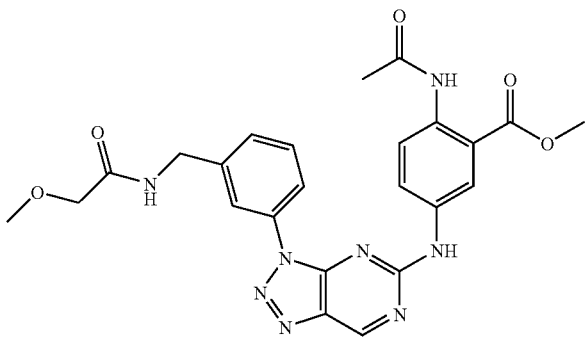
Co. No. 157; Ex. B1b-4; mp. 226° C.
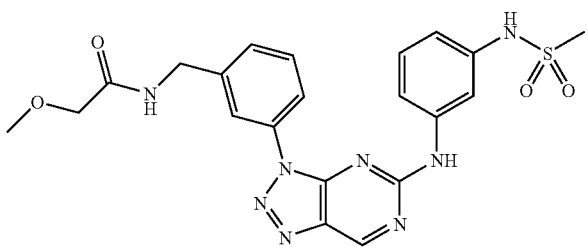
Co. No. 158; Ex. B1b-4; mp. 146° C.
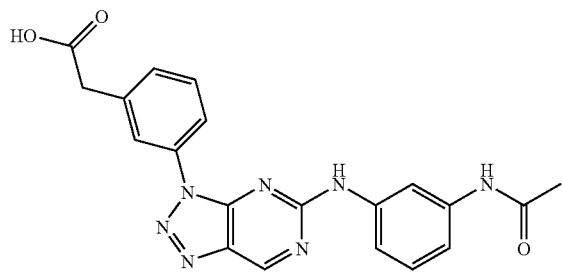
Co. No. 159; Ex. B1b-2; mp. >260° C.
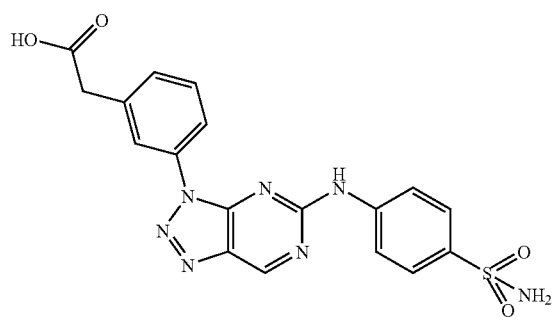
Co. No. 160; Ex. B1a-1; mp. 166° C.

TABLE 1-continued
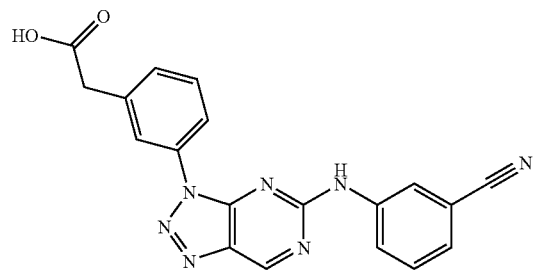
Co. No. 161; Ex. B1a-1; mp. 255° C.
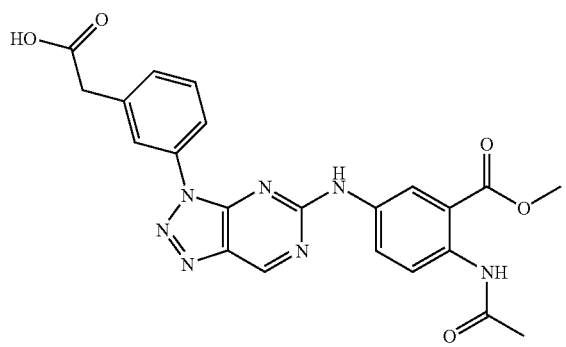
Co. No. 162; Ex. B1a-1; mp. >260° C.
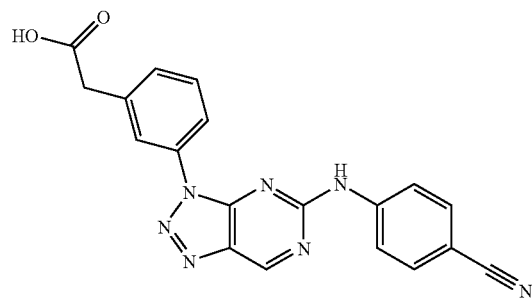
Co. No. 163; Ex. B1a-1; mp. >260° C.
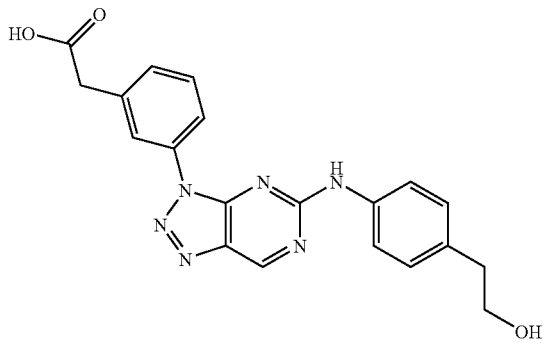
Co. No. 164; Ex. B1a-1; mp. 226° C.

TABLE 1-continued
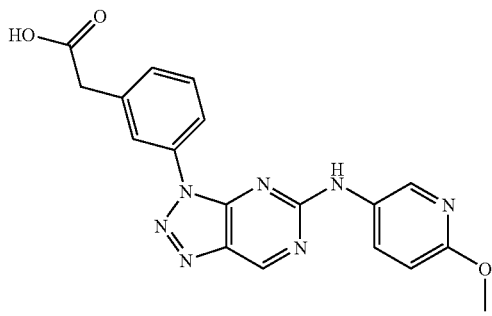
Co. No. 165; Ex. B1a-1; mp. 225° C.
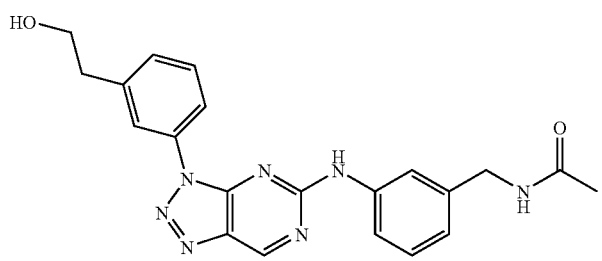
Co. No. 167; Ex. B1b-2; mp. 139° C.
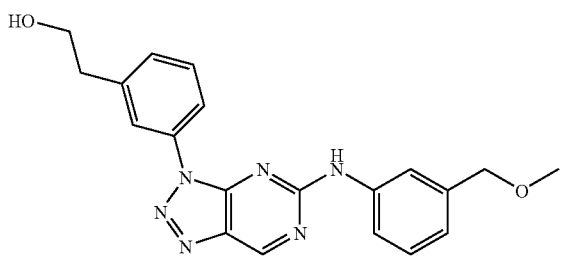
Co. No. 168; Ex. B1b-2; mp. 140° C.
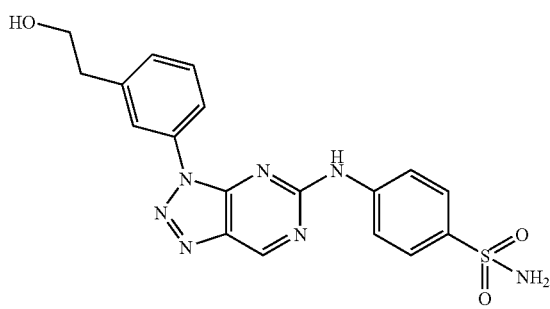
Co. No. 169; Ex. B1b-2; mp. 213° C.
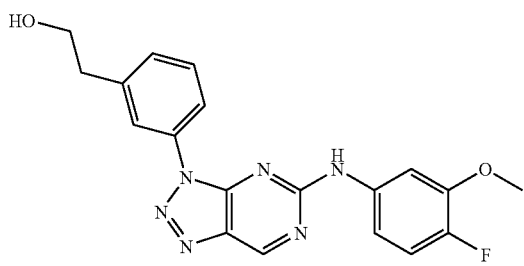
Co. No. 171; Ex. B1b-2; mp. 168° C.

TABLE 1-continued
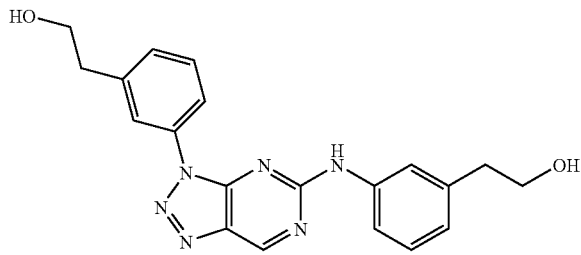
Co. No. 172; Ex. B1b-2; mp. 186° C.
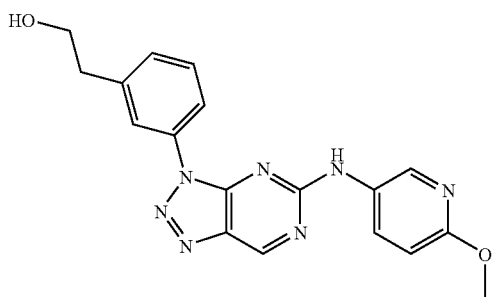
Co. No. 173; Ex. B1b-2; mp. 172° C.
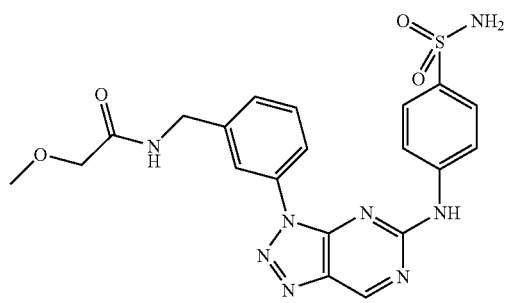
Co. No. 174; Ex. B1b-3; mp. 216° C.
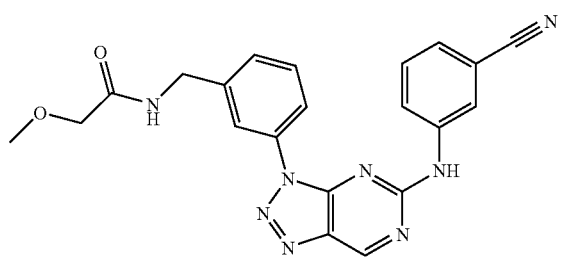
Co. No. 175; Ex. B1b-3; mp. 208° C.
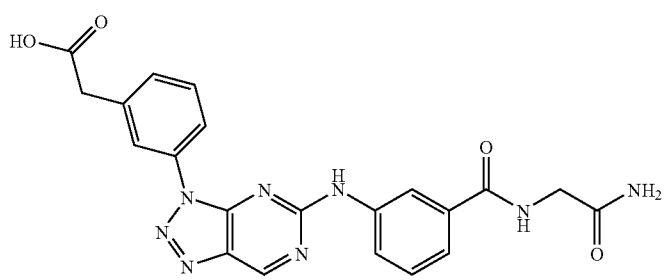
Co. No. 176; Ex. B1a-1; mp. 249° C.

TABLE 1-continued
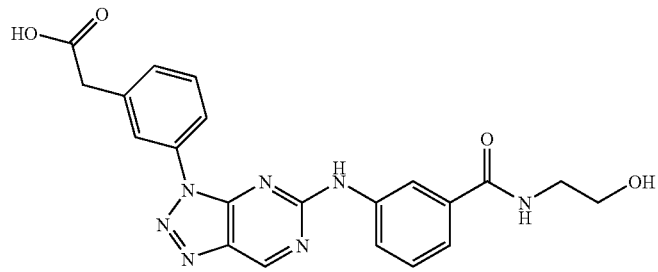
Co. No. 177; Ex. B1a-1; mp. 234° C.
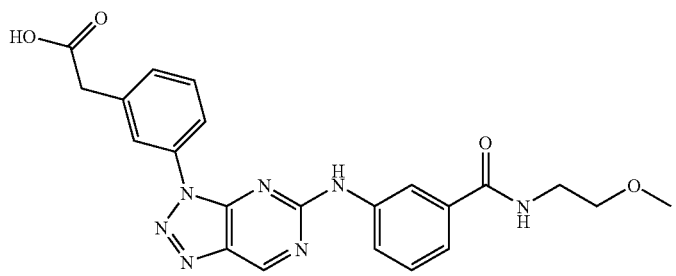
Co. No. 178; Ex. B1a-1; mp. 236° C.
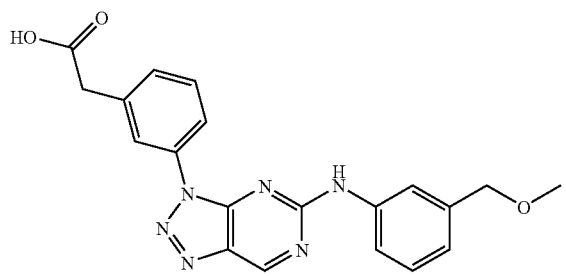
Co. No. 179; Ex. B1a-1; mp. 231° C.
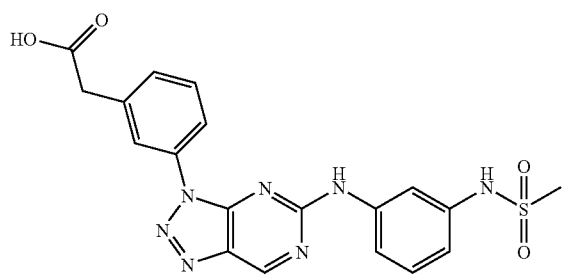
Co. No. 180; Ex. B1a-1; mp. 262° C.
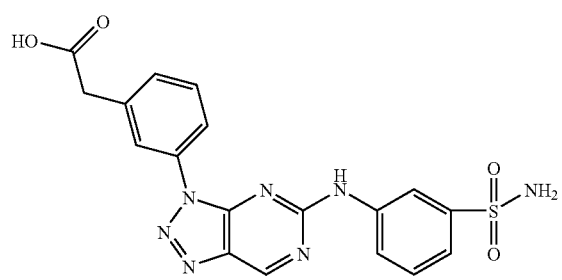
Co. No. 181; Ex. B1a-1; mp. 262° C.

TABLE 1-continued
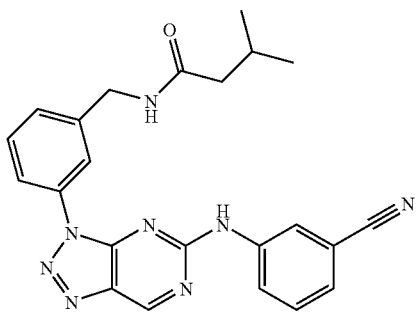
Co. No. 185; Ex. B1b-10;
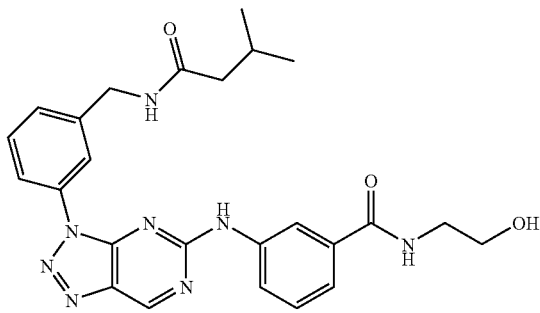
Co. No. 186; Ex. B1b-10;
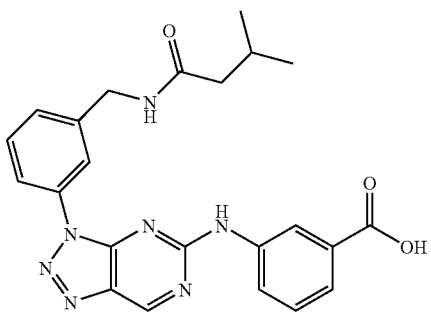
Co. No. 187; Ex. B1b-10;
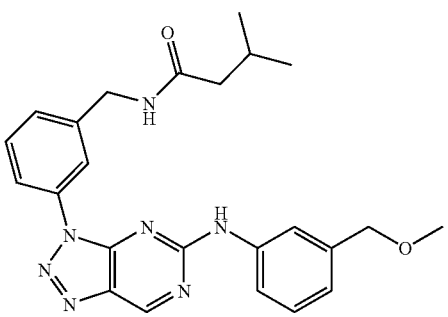
Co. No. 188; Ex. B1b-10;

TABLE 1-continued
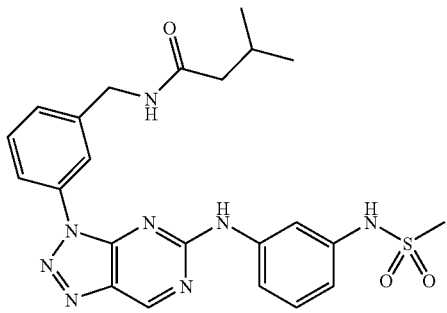
Co. No. 189; Ex. B1b-10;
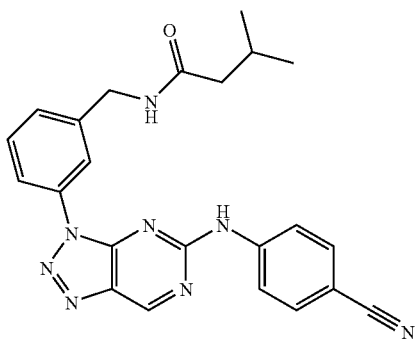
Co. No. 190; Ex. B1b-10;
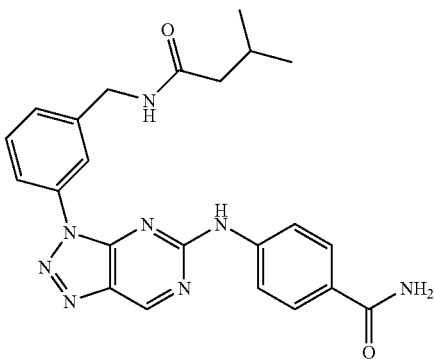
Co. No. 191; Ex. B1b-10;
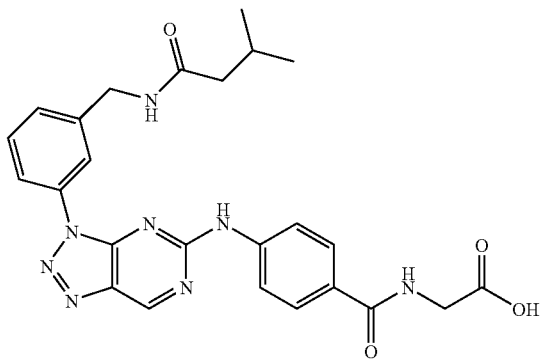
Co. No. 192; Ex. B1b-10;

TABLE 1-continued
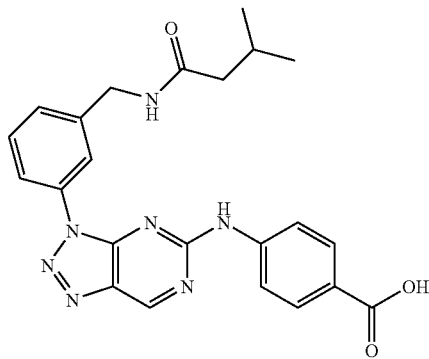
Co. No. 193; Ex. B1b-10; mp. ° C.
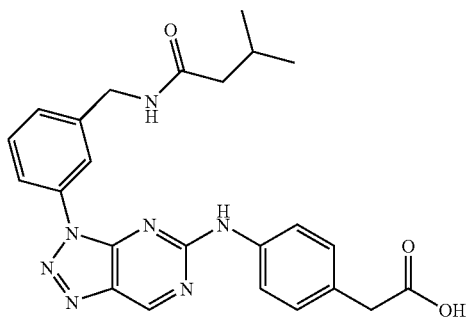
Co. No. 194; Ex. B1b-10; mp. ° C.
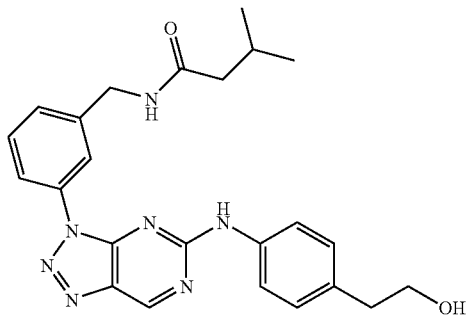
Co. No. 195; Ex. B1b-10;
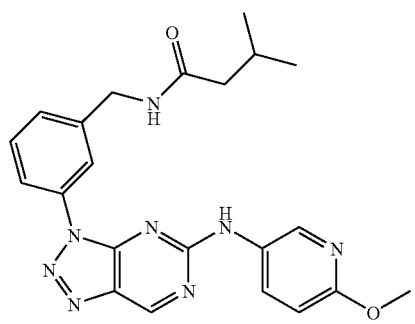
Co. No. 196; Ex. B1b-10;

TABLE 1-continued
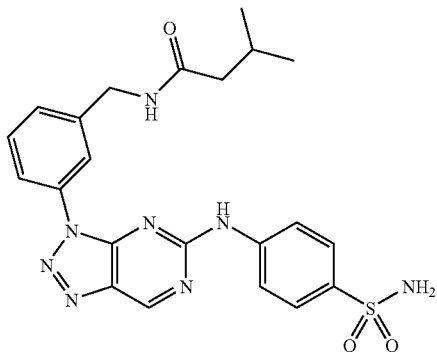
Co. No. 197; Ex. B1b-10;
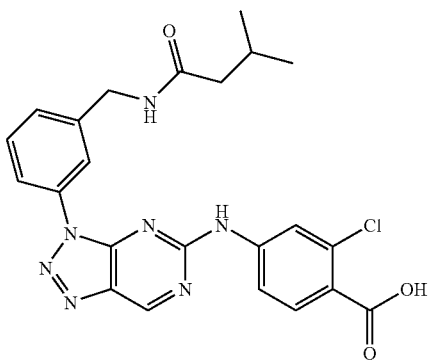
Co. No. 199; Ex. B1b-10;
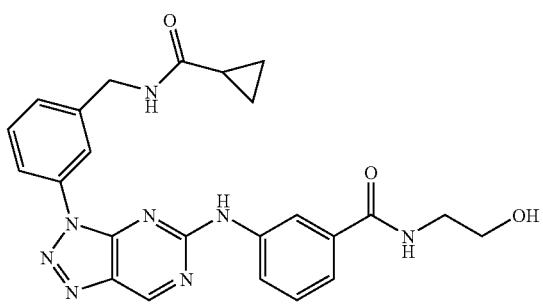
Co. No. 200; Ex. B1b-10;
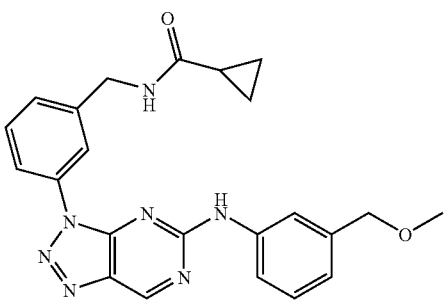
Co. No. 201; Ex. B1b-10;

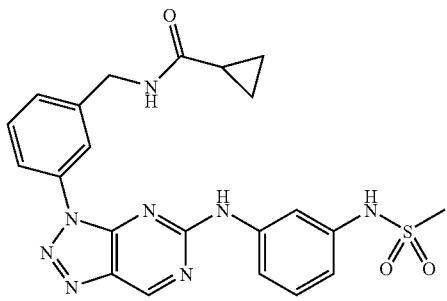
Co. No. 202; Ex. B1b-10;
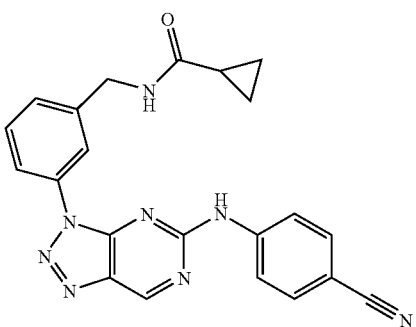
Co. No. 203; Ex. B1b-10;
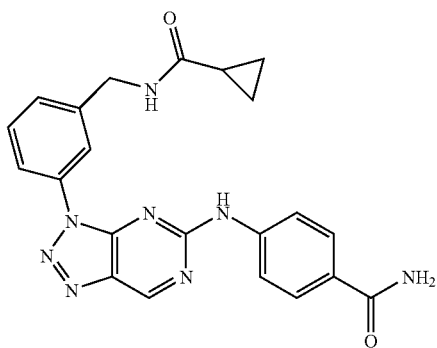
Co. No. 204; Ex. B1b-10;
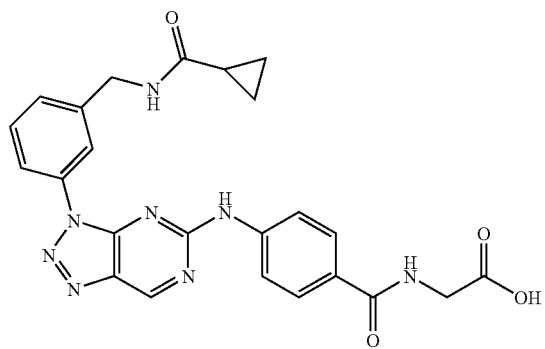
Co. No. 205; Ex. B1b-10;

TABLE 1-continued
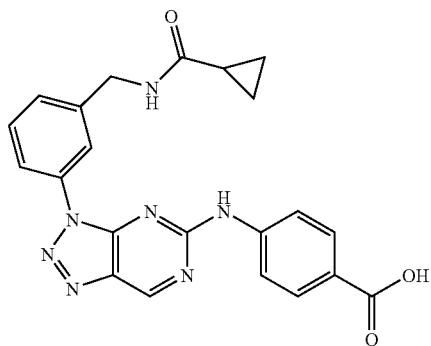
Co. No. 206; Ex. B1b-10;
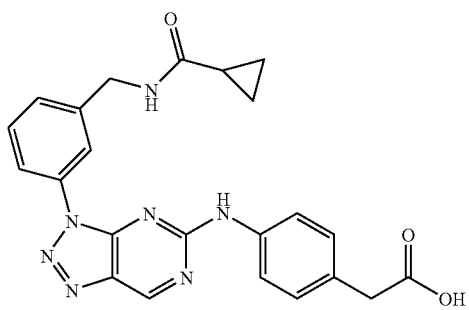
Co. No. 207; Ex. B1b-10;
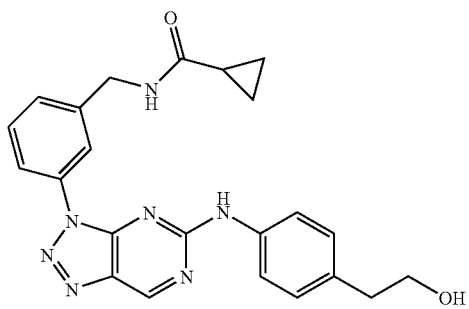
Co. No. 208; Ex. B1b-10;
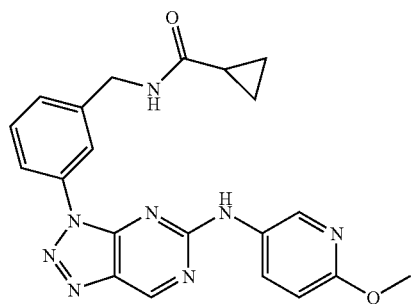
Co. No. 209; Ex. B1b-10;

TABLE 1-continued
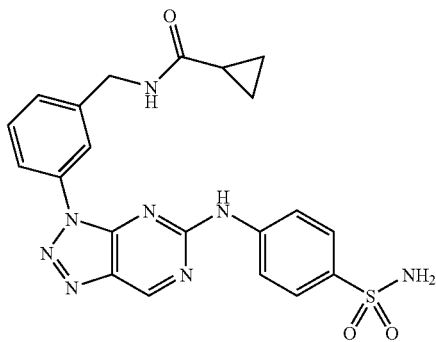
Co. No. 210; Ex. B1b-10;
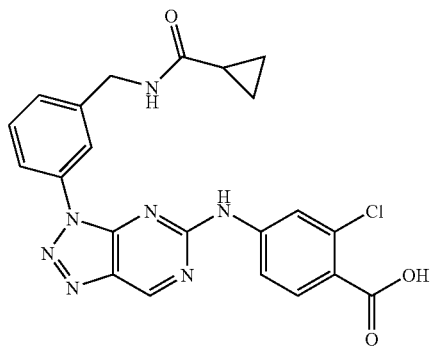
Co. No. 212; Ex. B1b-10;
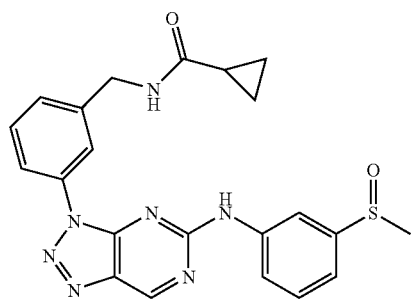
Co. No. 213; Ex. B1b-10;
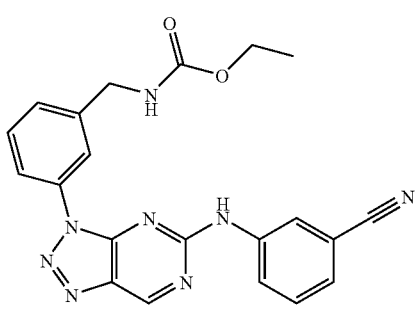
Co. No. 214; Ex. B1b-3;

TABLE 1-continued
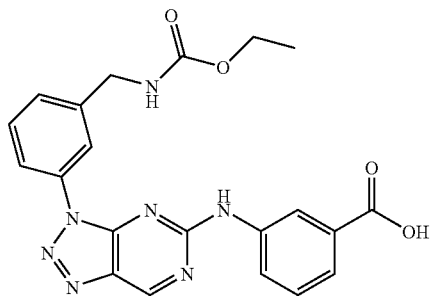
Co. No. 215; Ex. B1b-3;
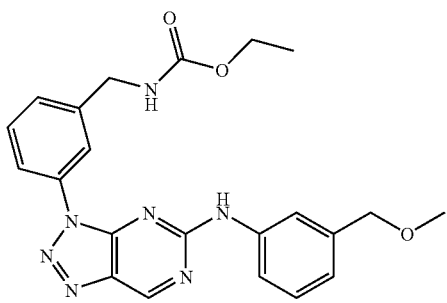
Co. No. 216; Ex. B1b-3;
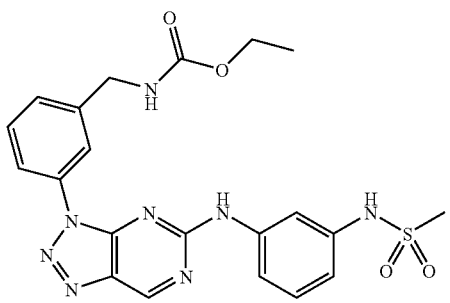
Co. No. 217; Ex. B1b-3; mp. 202° C.
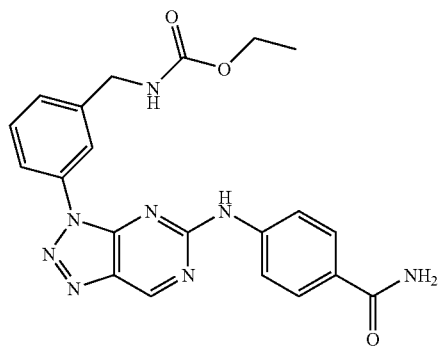
Co. No. 218; Ex. B1b-3;

TABLE 1-continued
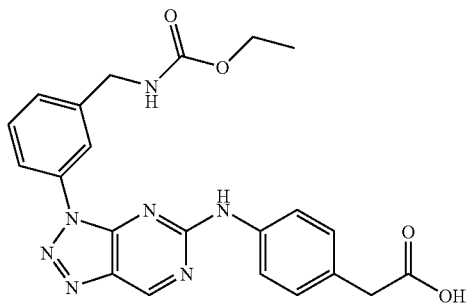
Co. No. 219; Ex. B1b-3;
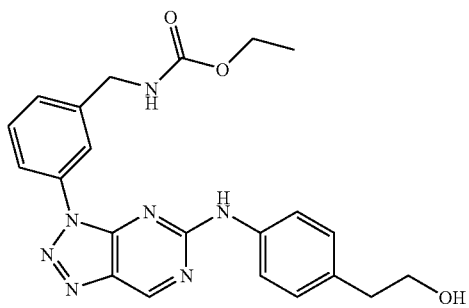
Co. No. 220; Ex. B1b-3;
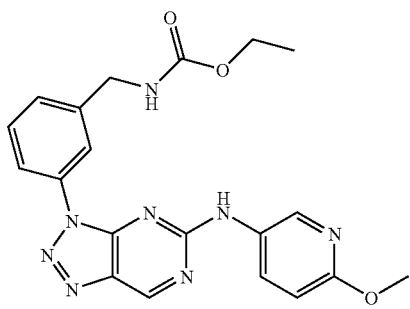
Co. No. 221; Ex. B1b-3;
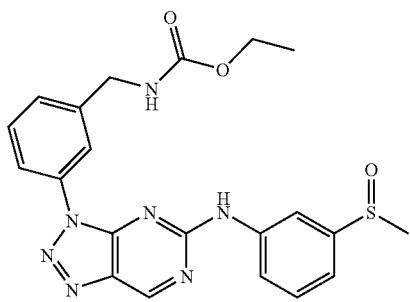
Co. No. 223; Ex. B1b-3;

TABLE 1-continued
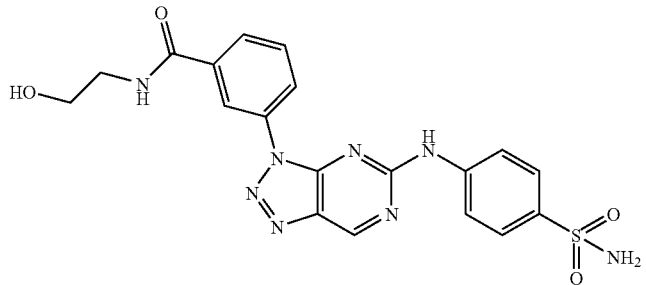
Co. No. 227; Ex. B2c; mp. 216° C.
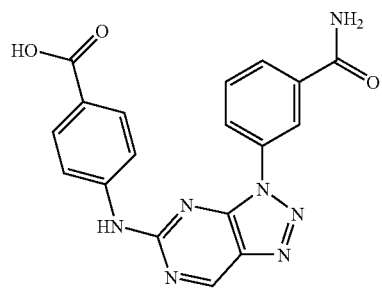
Co. No. 228; Ex. B2c; mp. >260° C.
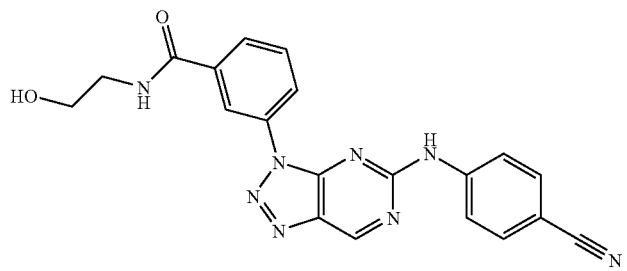
Co. No. 229; Ex. B2c; mp. 242° C.
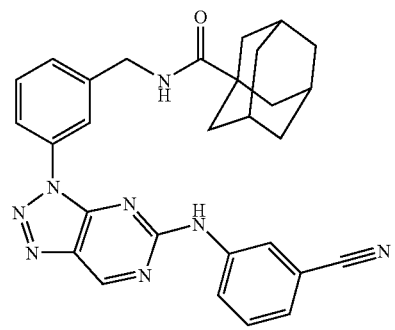
Co. No. 231; Ex. B1b-11;

TABLE 1-continued
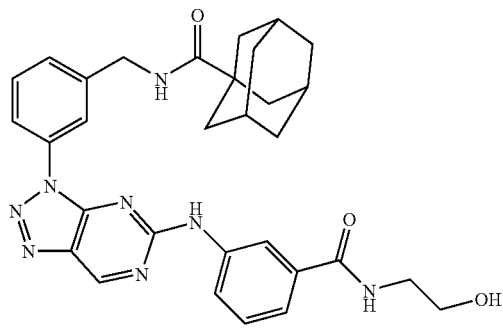
Co. No. 232; Ex. B1b-11;
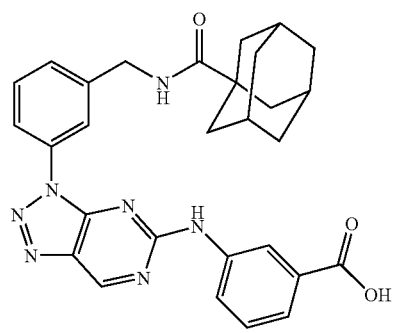
Co. No. 233; Ex. B1b-11;
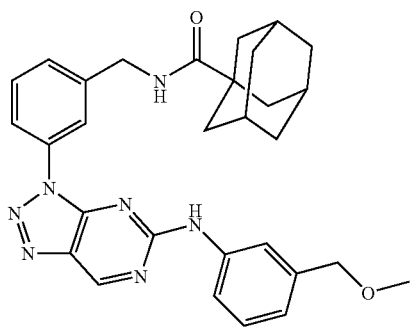
Co. No. 234; Ex. B1b-11;
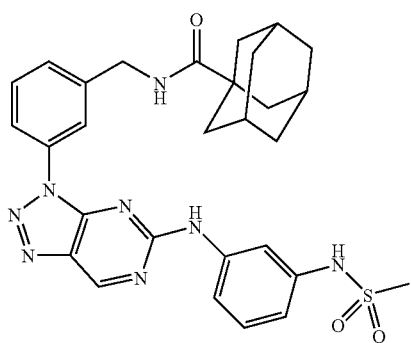
Co. No. 235; Ex. B1b-11;

TABLE 1-continued
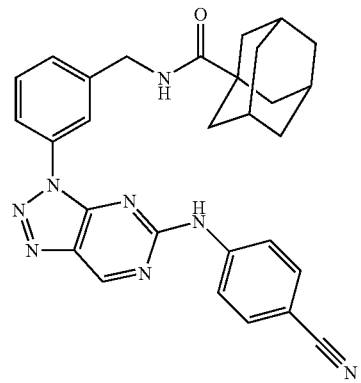
Co. No. 236; Ex. B1b-11;
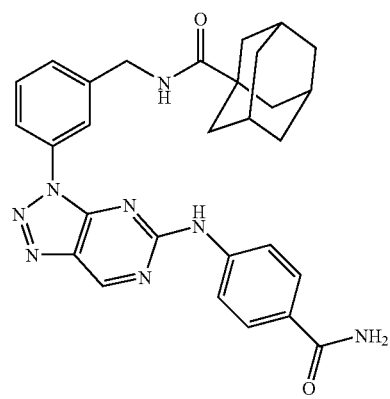
Co. No. 237; Ex. B1b-11;
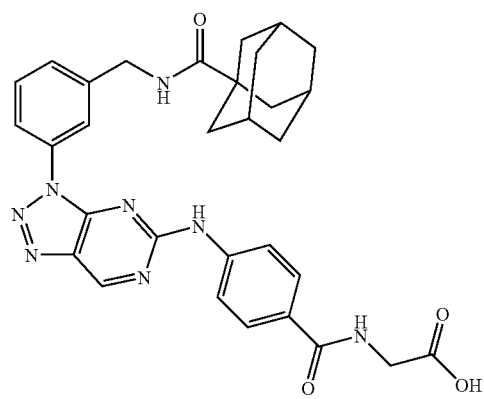
Co. No. 238; Ex. B1b-11;

TABLE 1-continued
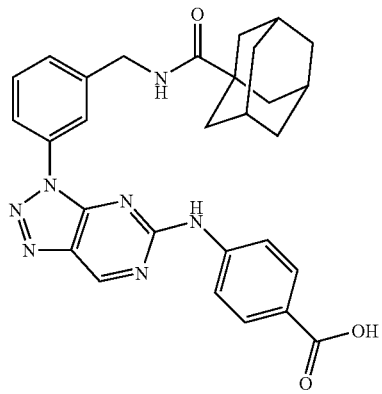
Co. No. 239; Ex. B1b-11;
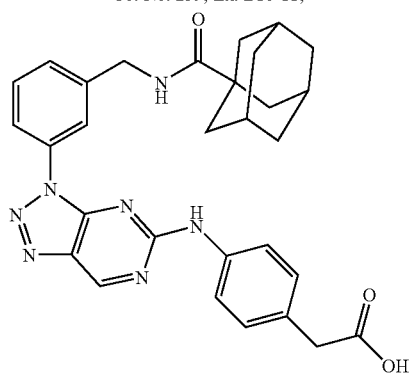
Co. No. 240; Ex. B1b-11;
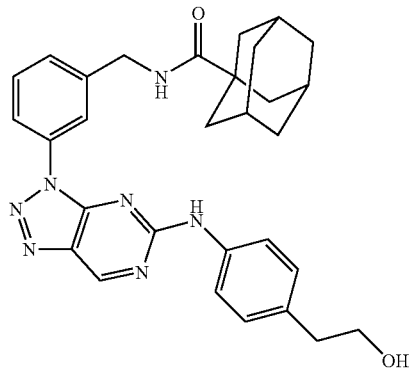
Co. No. 241; Ex. B1b-11;
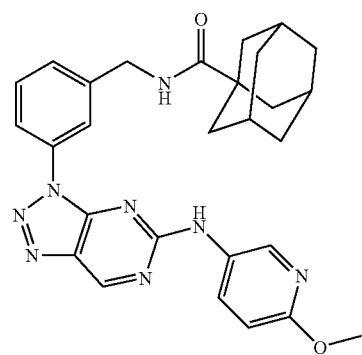
Co. No. 242; Ex. B1b-11;

TABLE 1-continued
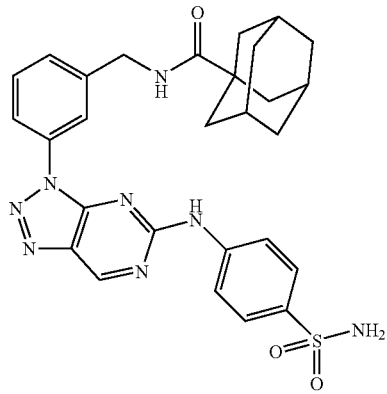
Co. No. 243; Ex. B1b-11;
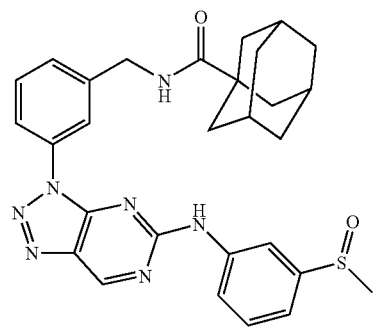
Co. No. 245; Ex. B1b-11;
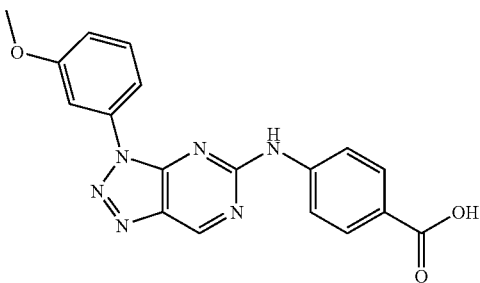
Co. No. 246; Ex. B2c; mp. >260° C.
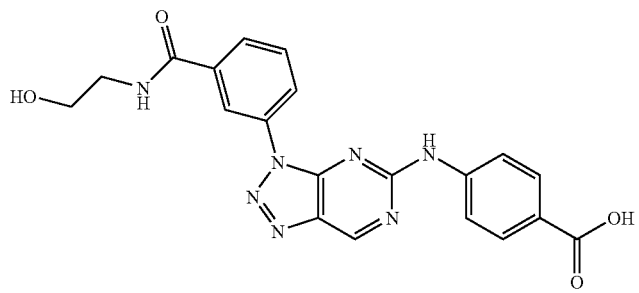
Co. No. 247; Ex. B2c; mp. >260° C.

TABLE 1-continued
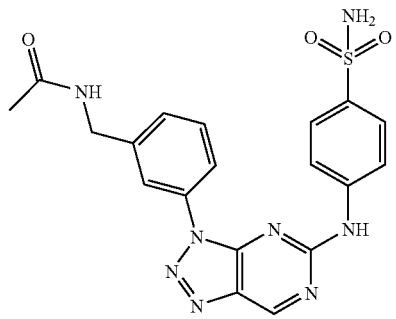
Co. No. 248; Ex. B1b-1;
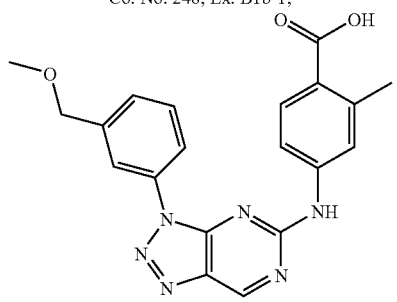
Co. No. 249; Ex. B1e;
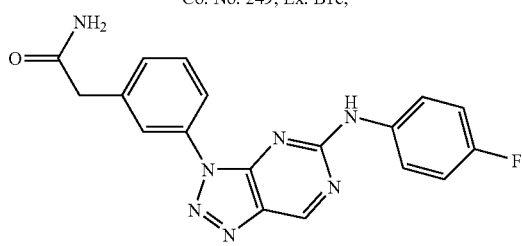
Co. No. 254; Ex. B1b-1; mp. 216° C.
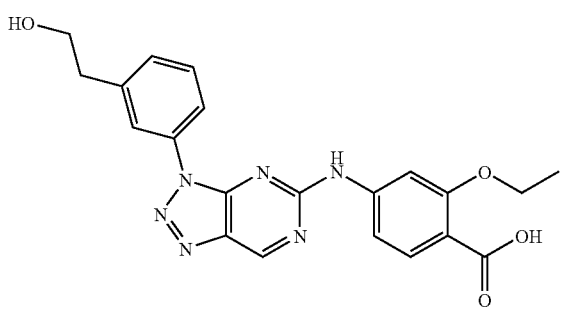
Co. No. 255; Ex. B2c; mp. 170° C.
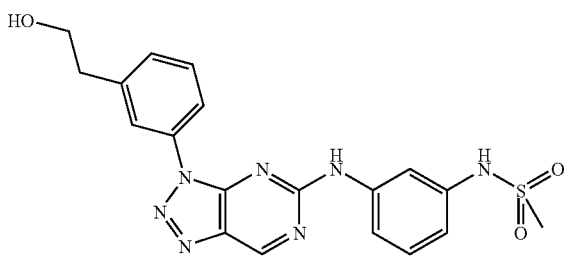
Co. No. 256; Ex. B1b-2; mp. 205° C.

TABLE 1-continued
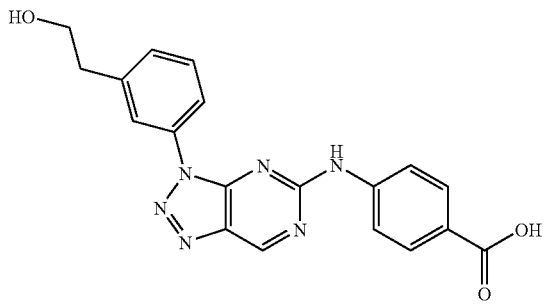
Co. No. 257; Ex. B1b-2; mp. >260° C.
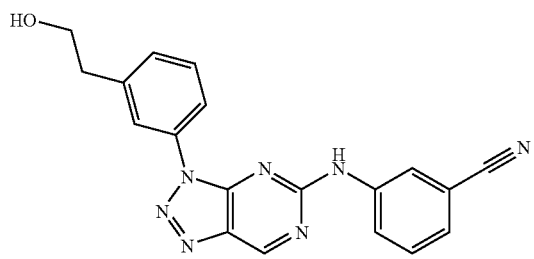
Co. No. 258; Ex. B1b-2; mp. 177° C.
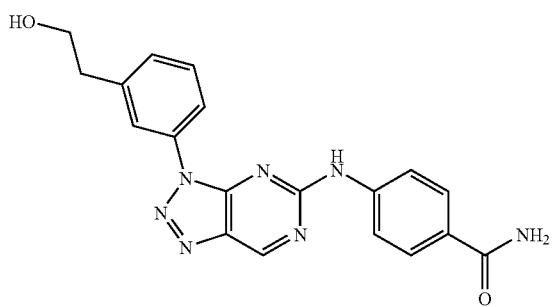
Co. No. 259; Ex. B1b-2; mp. 234° C.
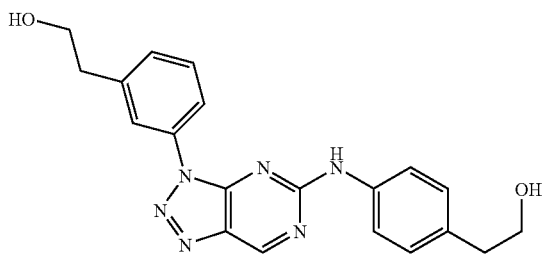
Co. No. 260; Ex. B1b-2; mp. 184° C.
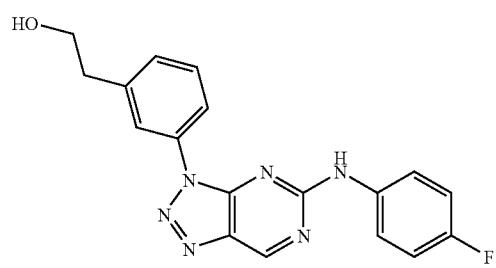
Co. No. 261; Ex. B1b-2; mp. 150° C.

TABLE 1-continued
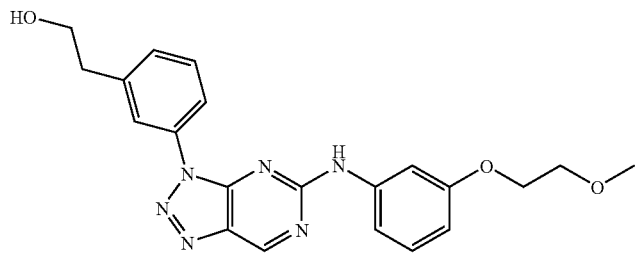
Co. No. 262; Ex. B1b-2; mp. 114° C.
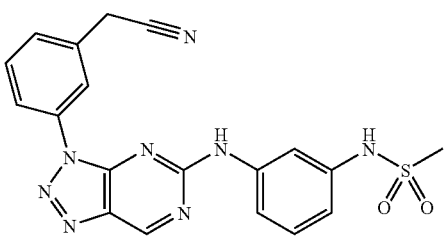
Co. No. 264; Ex. B1b-1; mp. >260° C.
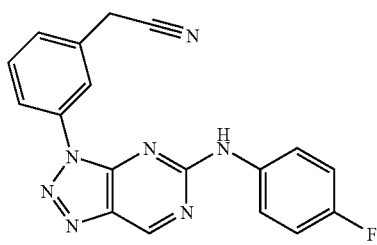
Co. No. 265; Ex. B1b-2; mp. 246° C.
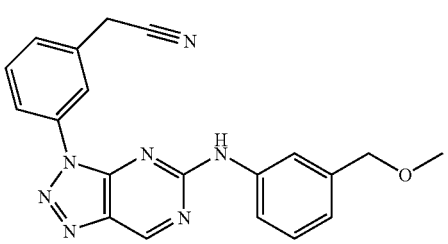
Co. No. 266; Ex. B1b-2; mp. 158° C.
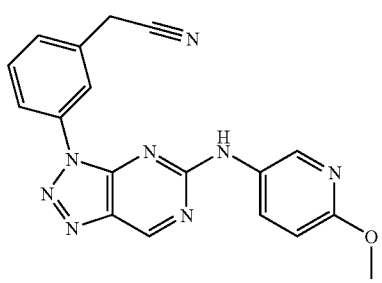
Co. No. 267; Ex. B1b-2; mp. 208° C.

TABLE 1-continued
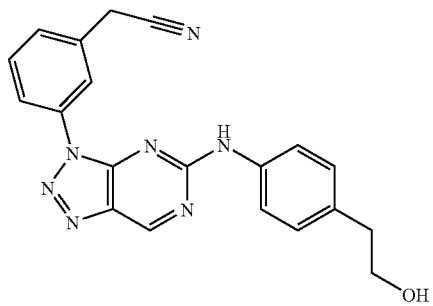
Co. No. 268; Ex. B1b-1; mp. 192° C.
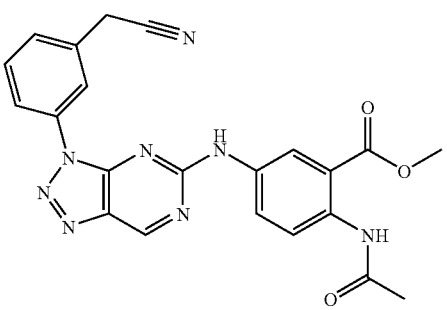
Co. No. 269; Ex. B1b-1; mp. 242° C.
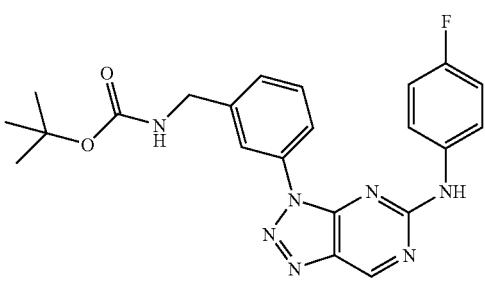
Co. No. 270; Ex. B1b-1; mp. 194° C.
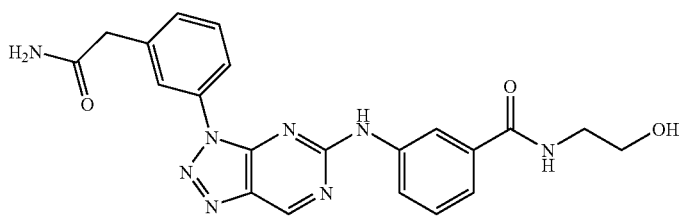
Co. No. 271; Ex. B1b-2; mp. 210° C.
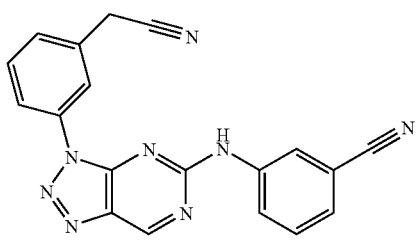
Co. No. 272; Ex. B1b-1; mp. 216° C.

TABLE 1-continued
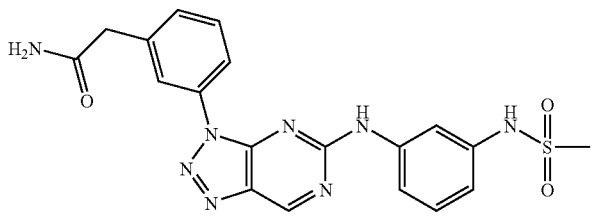
Co. No. 273; Ex. B1b-2; mp. 242° C.
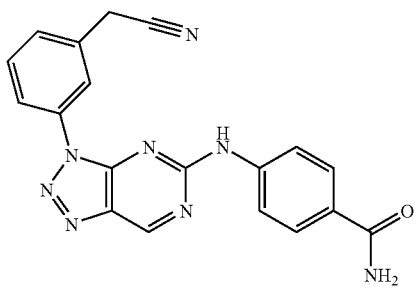
Co. No. 274; Ex. B1b-1; mp. 250° C.
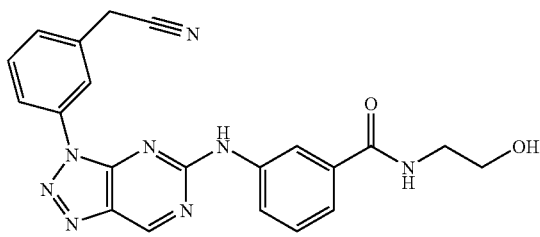
Co. No. 275; Ex. B1b-2; mp. 242° C.
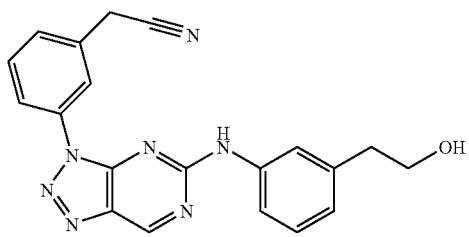
Co. No. 276; Ex. B1b-4; mp. 162° C.
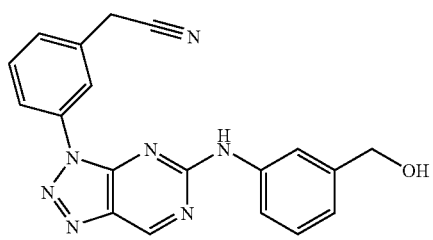
Co. No. 277; Ex. B1b-2; mp. 143° C.

TABLE 1-continued
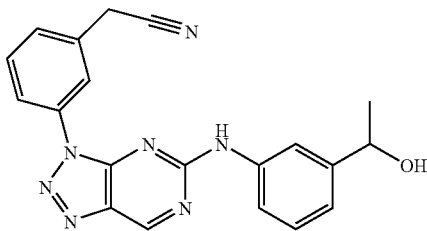
Co. No. 278; Ex. B1b-2; mp. 193° C.
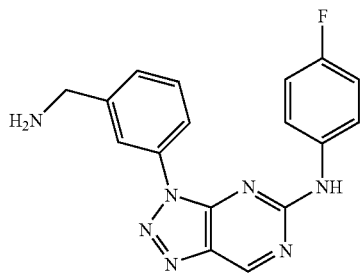
Co. No. 279; Ex. B7;
.2HCl
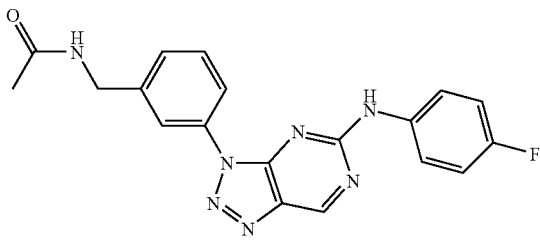
Co. No. 280; Ex. B1b-1; mp. 220° C.
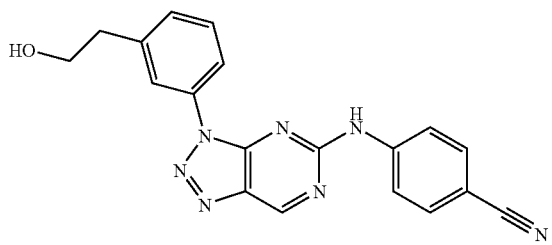
Co. No. 285; Ex. B1b-2; mp. 204° C.
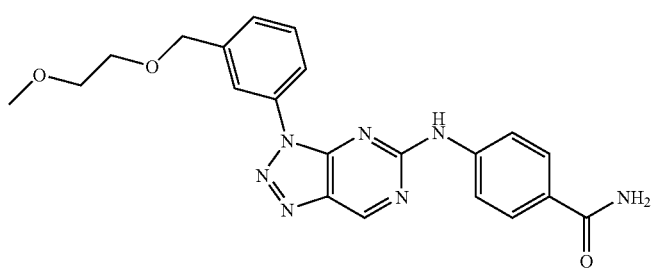
Co. No. 286; Ex. B1b-2; mp. 226° C.

TABLE 1-continued
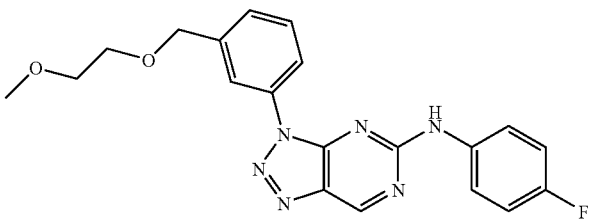
Co. No. 287; Ex. B1b-2; mp. 148° C.
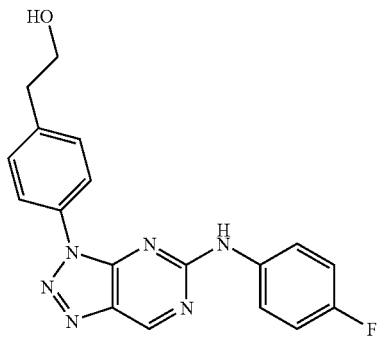
Co. No. 291; Ex. B1b-2; mp. 202° C.
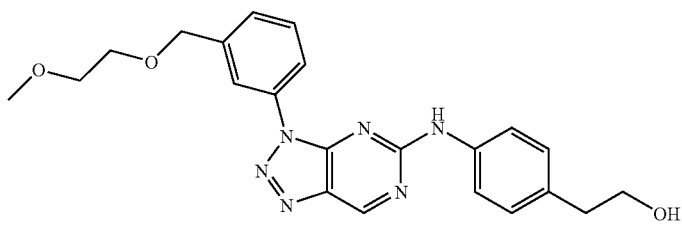
Co. No. 289; Ex. B1b-2; mp. 159° C.
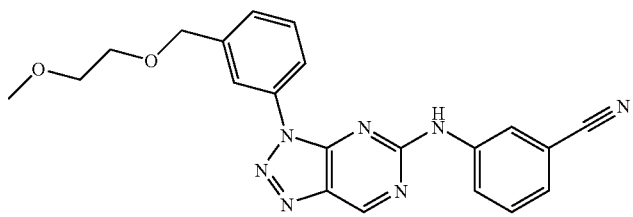
Co. No. 290; Ex. B1b-2; mp. 158° C.
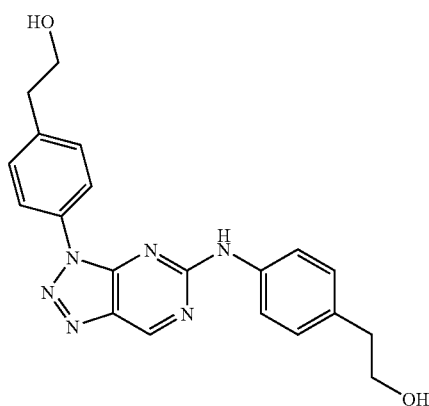
Co. No. 293; Ex. B1b-2; mp. 215° C.

TABLE 1-continued
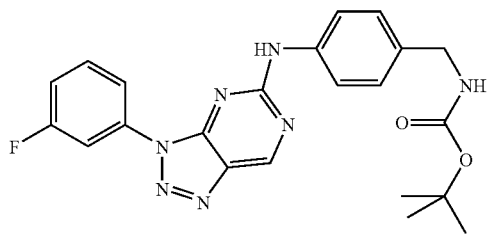
Co. No. 294; Ex. B1b-1; mp. 174° C.
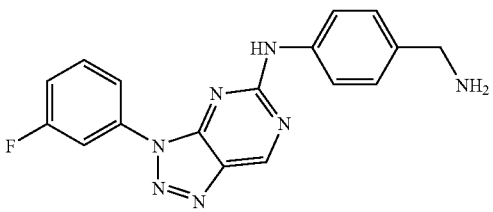
Co. No. 295; Ex. B5b; mp. >260° C.
.HCl
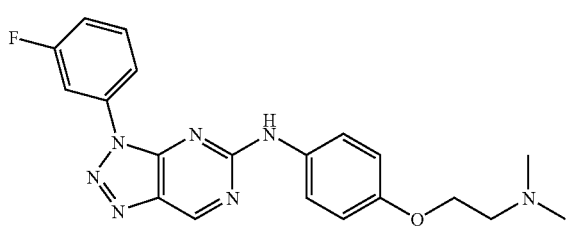
Co. No. 296; Ex. B1b-8; mp. 156° C.
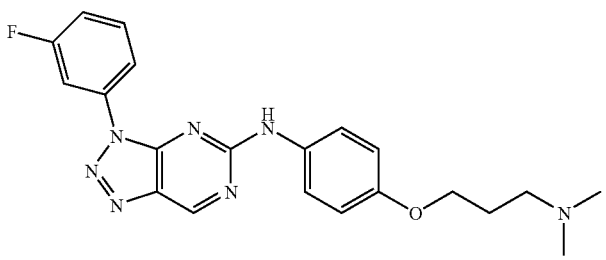
Co. No. 297; Ex. B1b-8; mp. 137° C.
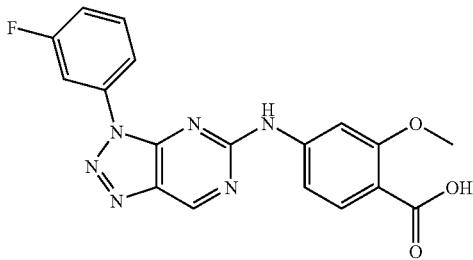
Co. No. 298; Ex. B2e; mp. 232° C.

TABLE 1-continued
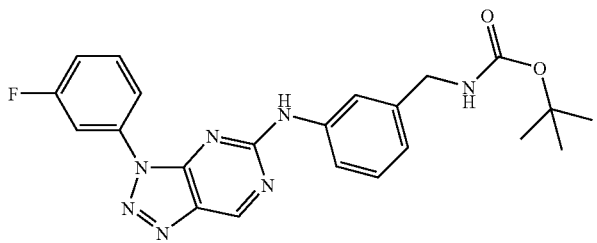
Co. No. 299; Ex. B1b-1; mp. 196° C.
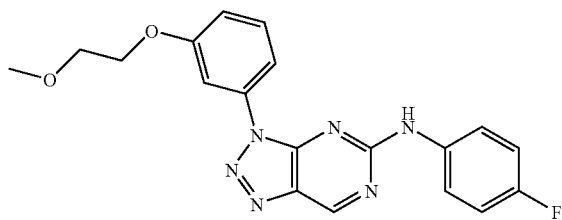
Co. No. 301; Ex. B1b-2; mp. 154° C.
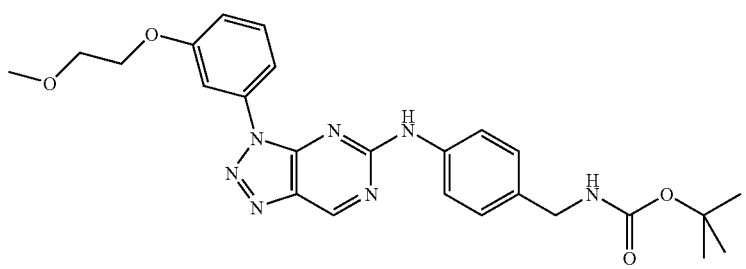
Co. No. 302; Ex. B1b-2; mp. 176° C.
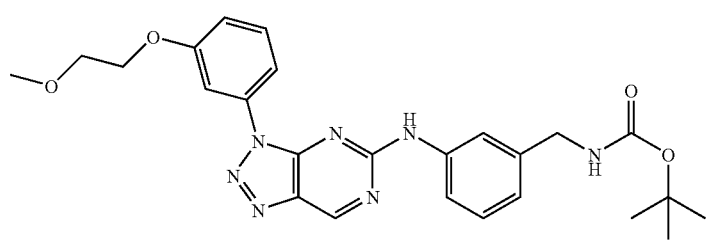
Co. No. 303; Ex. B1b-2; mp. 125° C.
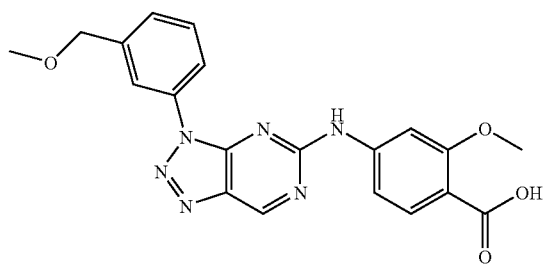
Co. No. 304; Ex. B2e; mp. 210° C.

TABLE 1-continued
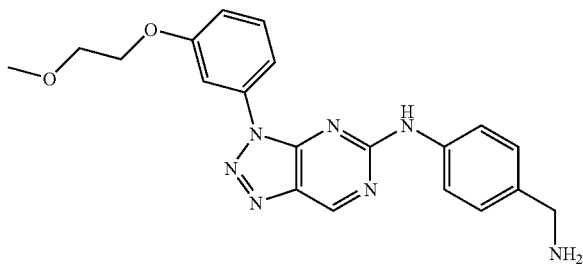
Co. No. 305; Ex. B5b; mp. 157° C.
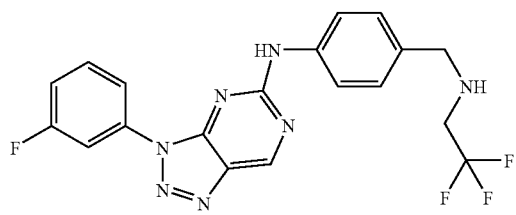
Co. No. 306; Ex. B5b; mp. 208° C.
.HCl
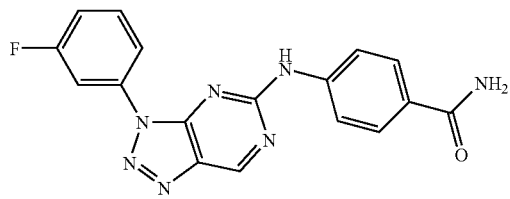
Co. No. 307; Ex. B1b-1; mp. >270° C.
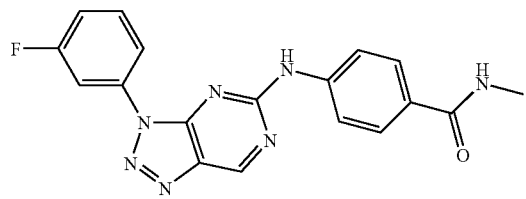
Co. No. 308; Ex. B1b-1; mp. 270° C.
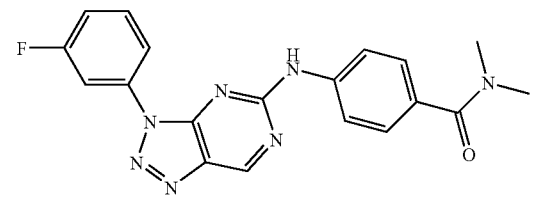
Co. No. 309; Ex. B1b-1; mp. 226° C.
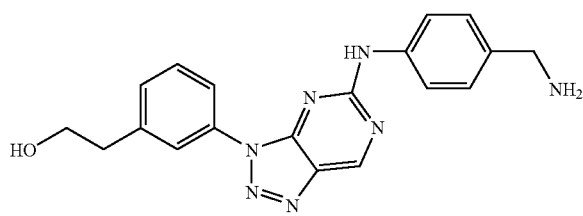
Co. No. 310; Ex. B1b-9; mp. 255° C.
.HCl TABLE 1-continued
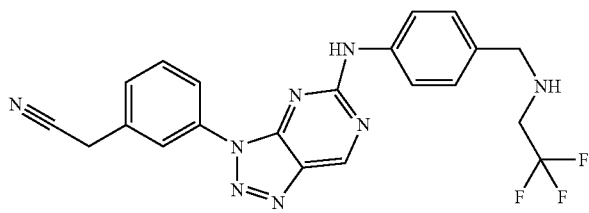
Co. No. 311; Ex. B1b-9; mp. 215 (decomposition)° C.
.HCl
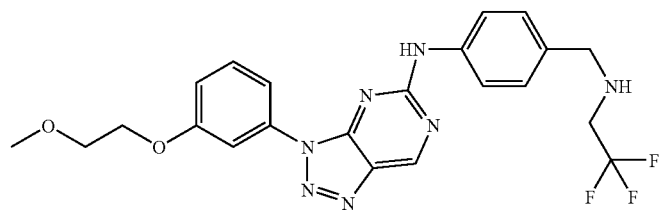
Co. No. 312; Ex. B1b-9; mp. 188 (decomposition)° C.
.HCl
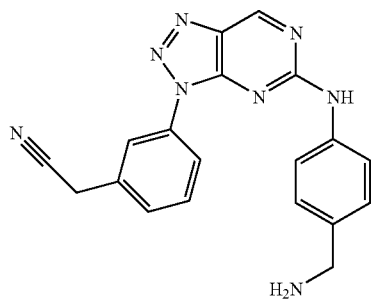
Co. No. 313; Ex. B1b-9; mp. >270° C.
.HCl
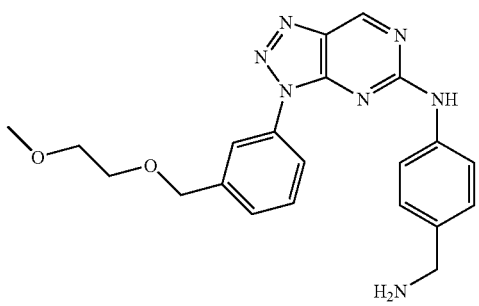
Co. No. 314; Ex. B1b-9; mp. 246° C.
.HCl TABLE 1-continued
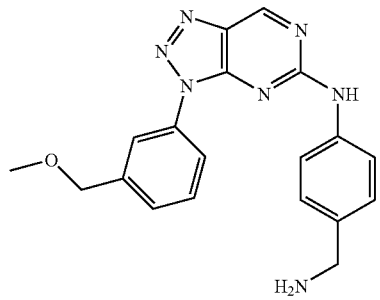
Co. No. 315; Ex. B1b-9; mp. 270° C.
.HCl
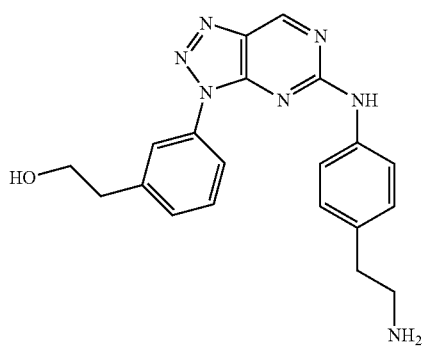
Co. No. 316; Ex. B1b-9; mp. >270° C.
.HCl
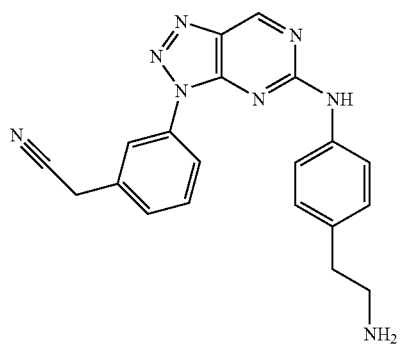
Co. No. 317; Ex. B1b-9; mp. 246° C.
.HCl
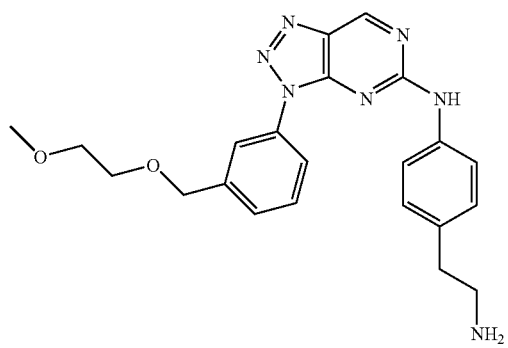
Co. No. 318; Ex. B1b-9; mp. 244° C.
.HCl TABLE 1-continued
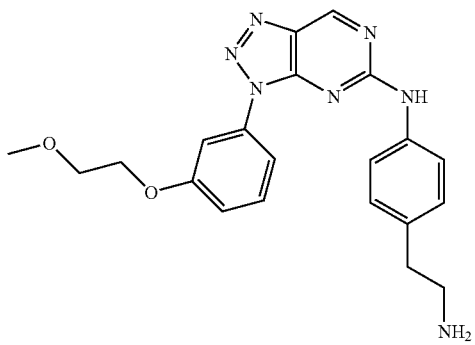
Co. No. 319; Ex. B1b-9; mp. 264° C.
.HCl
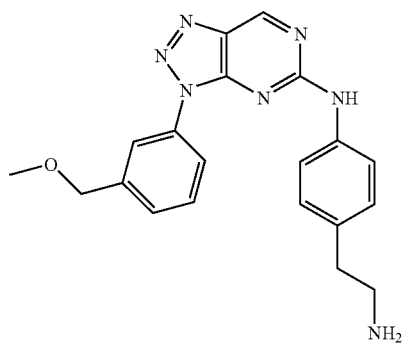
Co. No. 320; Ex. B1b-9; mp. 246° C.
.HCl
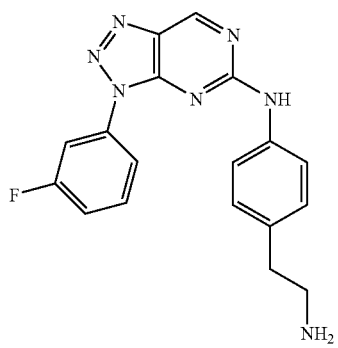
Co. No. 321; Ex. B1b-9; mp. >270° C.
.HCl
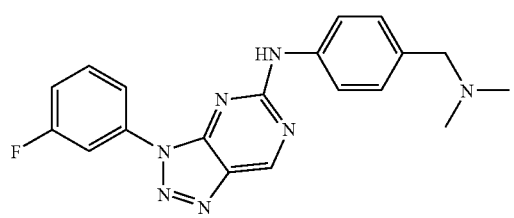
Co. No. 322; Ex. B8; mp. 260
(decomposition)° C.
.HCl TABLE 1-continued
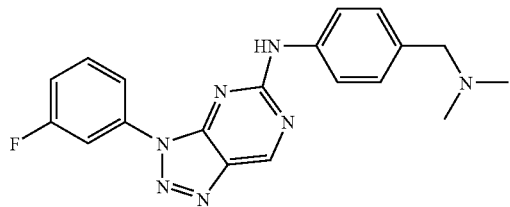
Co. No. 323; Ex. B8; mp. 192° C.
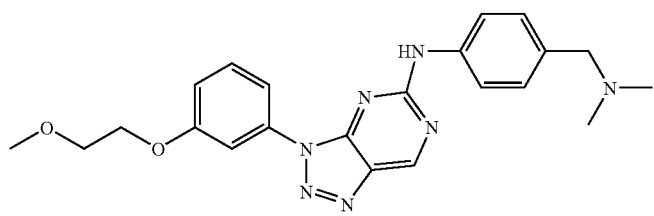
Co. No. 324; Ex. B8; mp. 184° C.
.HCl
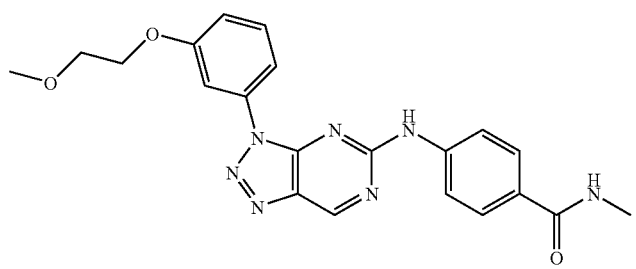
Co. No. 325; Ex. B1a-1;
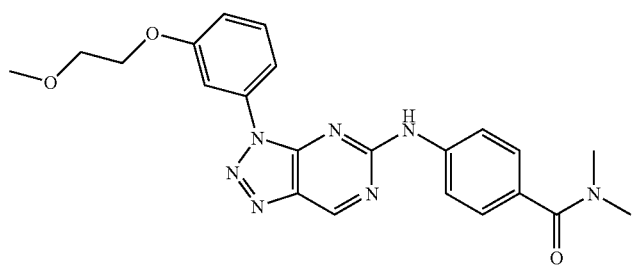
Co. No. 326; Ex. B1a-1; mp. 174° C.
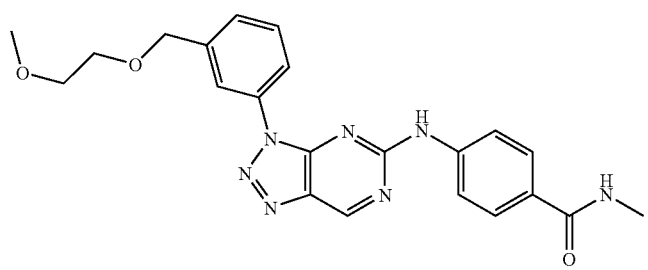
Co. No. 327; Ex. B1a-1; mp. 182° C.

TABLE 1-continued
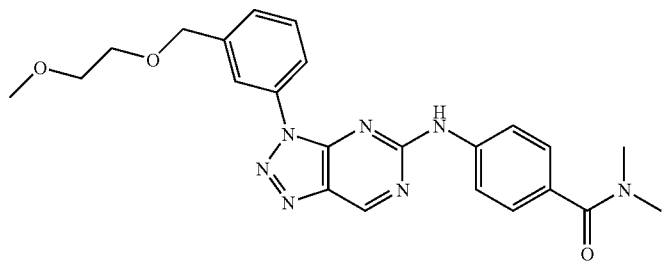
Co. No. 328; Ex. B1a-1;
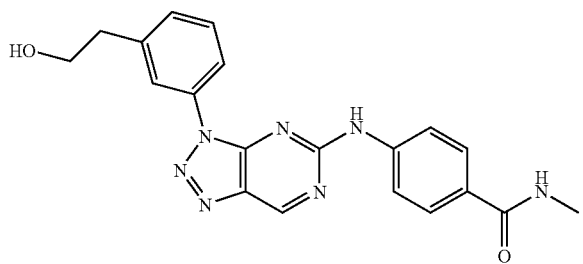
Co. No. 329; Ex. B1a-1; mp. 152° C.
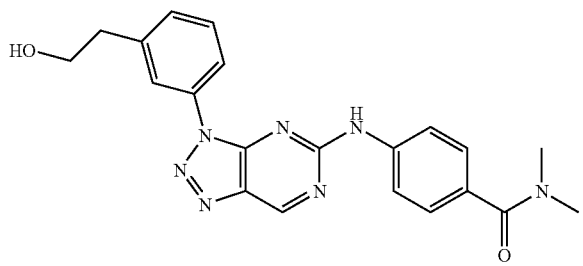
Co. No. 330; Ex. B1a-1; mp. 138° C.
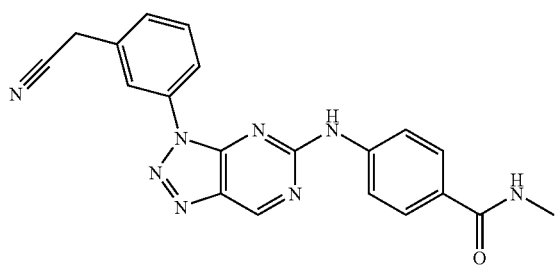
Co. No. 331; Ex. B1a-1;
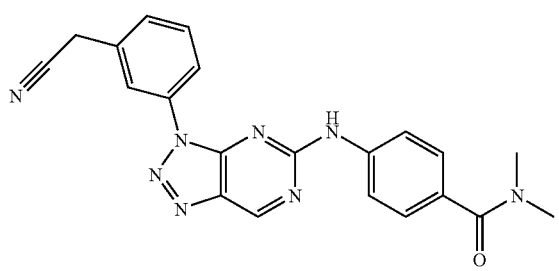
Co. No. 332; Ex. B1a-1;

TABLE 1-continued
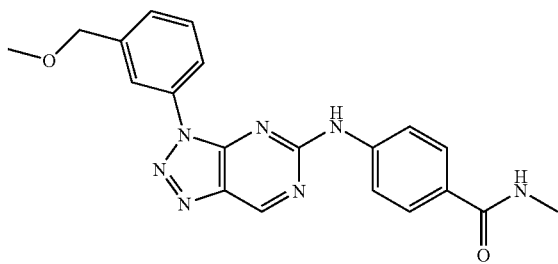
Co. No. 333; Ex. B1a-1;
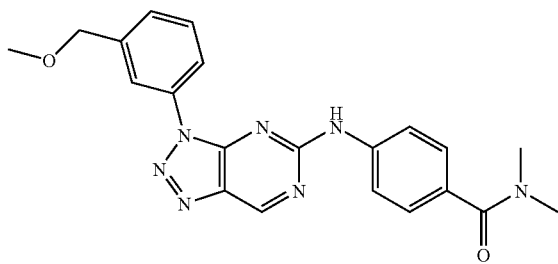
Co. No. 334; Ex. B1a-1;
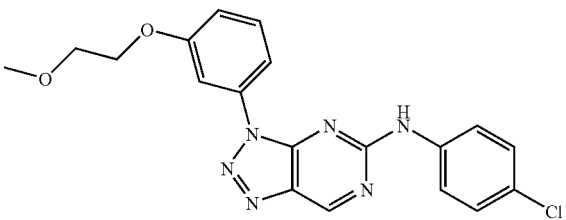
Co. No. 335; Ex. B1a-1; mp. 164° C.
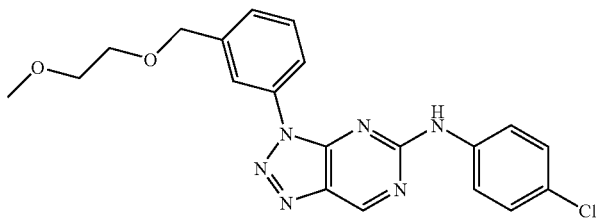
Co. No. 336; Ex. B1a-1; mp. 134° C.
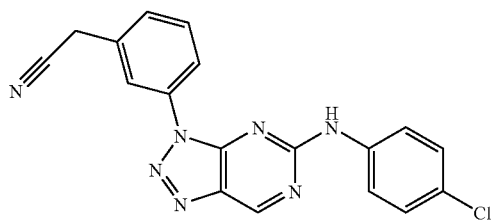
Co. No. 337; Ex. B1a-1; mp. 218° C.

TABLE 1-continued

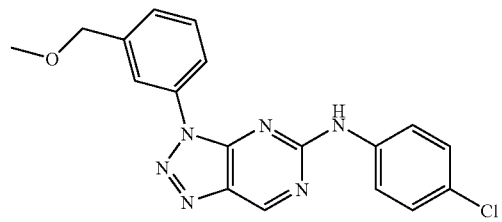

Co. No. 338; Ex. B1a-1; mp. 180° C.

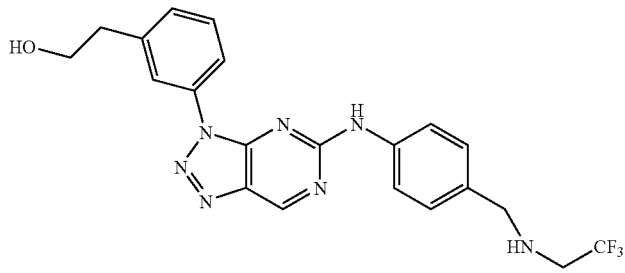

Co. No. 339; Ex. B1b-3

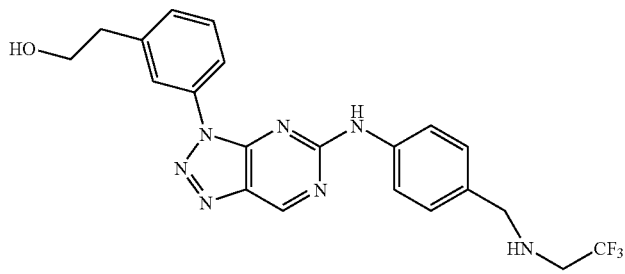

Co. No. 340; Ex. B1b-3
.HCl

C. Analytical Data

The mass of the compounds was recorded with LCMS (liquid chromatography mass spectrometry). Two methods were used which are described below. The data are gathered in Tables 2 and 3 below.

LCMS Conditions

Method BM001

The HPLC gradiet was supplied by a Waters 600 system with a column heater set at 45° C. Flow the column was split to a Waters 996 photodiode array (PDA) detector and a Waters-Micromass LCT mass spectrometer with an electrospray ionization source operated in positive ionization mode. Reversed phase HPLC was carried out on a Xterra MS C18 column (3.5 mm, 4.6×100 mm) with a flow rate of 1.6 ml/minute. Three mobile phases (mobile phase A 95% 25 mM ammoniumacetate +5% acetonitrile mobile phase B: acetonitrile; mobile phase C: methanol) were employed to run a gradient condition from 100% A to 35% B and 35% C in 3 minutes, to 50% B and 50% C in 3.5 minutes, to 100% B in 0.5 minute, 100% B for 1 minute and reequilibrate with 100% A for 1.5 minutes. An injection volume of 10 μL was used.

Mass spectra were acquired by scanning from 100 to 1200. The capillary needle voltage was 3 kV and the source temperature was maintained at 120° C. Nitrogen was used a the nebulizer gas. Cone voltage was 10 V for positive ionzation mode. Data acquisition was performed with a Waters-Micromass MassLynx-Openlynx data system.

TABLE 2

LCMS parent peak and retention time values

| Co. No. | Retention time (minutes) | LCMS [M + H] Method BM001 |
|---|---|---|
| 185 | 7.69 | 427 |
| 186 | 5.71 | 489 |
| 187 | 5.15 | 446 |
| 188 | 6.55 | 446 |
| 189 | 5.76 | 495 |
| 190 | 6.24 | 427 |
| 191 | 8.69 | 445 |
| 192 | 5.27 | 503 |
| 193 | 5.09 | 446 |
| 194 | 8.24 | 460 |
| 195 | 6.06 | 446 |
| 196 | 6.11 | 433 |
| 197 | 5.61 | 481 |
| 199 | 5.29 | 480 |
| 200 | 5.44 | 473 |
| 201 | 6.26 | 430 |
| 202 | 5.51 | 479 |
| 203 | 5.96 | 411 |

TABLE 2-continued

LCMS parent peak and retention time values

| Co. No. | Retention time (minutes) | LCMS [M + H] Method BM001 |
|---|---|---|
| 204 | 8.39 | 429 |
| 205 | 5.02 | 487 |
| 206 | 4.83 | 430 |
| 207 | 7.94 | 444 |
| 208 | 5.77 | 430 |
| 209 | 5.83 | 417 |
| 210 | 5.34 | 465 |
| 212 | 5.02 | 464 |
| 213 | 5.41 | 448 |
| 214 | 6.42 | 415 |
| 215 | 5.11 | 434 |
| 216 | 6.52 | 434 |
| 217 | 5.73 | 483 |
| 218 | 5.72 | 433 |
| 219 | 5.32 | 448 |
| 220 | 6.01 | 434 |
| 221 | 6.11 | 421 |
| 223 | 5.66 | 452 |
| 231 | 7.53 | 505 |
| 232 | 6.57 | 567 |
| 233 | 5.94 | 525 |
| 234 | 7.59 | 524 |
| 235 | 6.64 | 573 |
| 236 | 7.24 | 505 |
| 237 | 6.64 | 523 |
| 238 | 6.02 | 581 |
| 239 | 5.91 | 524 |
| 240 | 6.2 | 538 |
| 241 | 6.95 | 524 |
| 242 | 7.13 | 511 |
| 243 | 6.44 | 559 |
| 245 | 6.64 | 542 |

Method B1001

The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 mm, 4.6×100 mm) with a flow rate of 1.6 ml/minute. Three mobile phases (mobile phase A 95% 25 mM ammoniumacetate +5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 µL was used.

Mass spectra were acquired by scanning from 100 to 1000 in 1 second using a dwell time of 0.1 s. The capillary needle voltage was 3 kV and the source temperature was maintained at 140° C. Nitrogen was used a the nebulizer gas. Cone voltage was 10 V for positive ionzation mode and 20 V for negative ionization mode. Data acquisition was performed with a Waters-Micromass MassLynx-Openlynx data system.

TABLE 3

LCMS parent peak and retention time values.

| Co. No. | Retention time | LCMS [M + H] Method B1001 |
|---|---|---|
| 13 | 6.1 | 365 |
| 14 | 6.41 | 321 |
| 15 | 5.26 | 323 |
| 16 | 6.97 | 375 |
| 17 | 6.19 | 325 |
| 18 | 6.16 | 364 |
| 19 | 6.11 | 373 |
| 20 | 5.58 | 346 |
| 32 | 5.83 | 342 |
| 21 | 5.72 | 337 |
| 22 | 6.58 | 391 |
| 23 | 6.36 | 351 |
| 325 | 4.63 | 420 |
| 326 | 4.87 | 434 |
| 327 | 4.58 | 434 |
| 328 | 4.82 | 448 |
| 329 | 4.08 | 390 |
| 330 | 4.31 | 404 |
| 331 | 4.19 | 385 |
| 332 | 4.44 | 399 |
| 333 | 4.57 | 390 |
| 334 | 4.88 | 404 |

D. Pharmacological Example

The pharmacological activity of the present compounds was examined using the following test.

GSK3beta assays were performed at room temperature in a 100 µl reaction volume of 25 mM Tris (ph 7.4) containing 10 mM $MgCl_2.6H_2O$ 1 mM DTT, 0.1 mg/ml BSA, 5% glyceol and containing 5.7 ng/µl GSK3β, 5 µM biotinylated phosphorylated CREB peptide, 1 µM APT, 0.85 µCi/ml ATP-$P^{33}$ and a suitable amount of a test compound of formula (I). After one hour, the reaction was terminated by adding 70 µl of Stop mix (0.1 mM APT, 5 mg/ml streptavidin coated PVT SPA bead pH 11.0). The beads to which the phosphorylated CREB peptide is attached were allowed to settle overnight and the radioactivity of the beads was counted in a microtiterplate scintillation counter and compared with the results obtained in a control experiment (without the presence of a test compound) in order to determine the percentage of GSK3β inhibition. The $IC_{50}$ value, i.e. the concentration (M) of the test compound at which 50% of GSK3β is inhibited, was calculated from the dose response curve obtained by performing the above-described GSKK3β assay in the presence of different amounts of the test compound.

The GSK3alpha assay was performed in the same way as described above for the GSK3beta assay except for the concentration of GSK3alpha which is 0.25 ng/µl.

Table 4 list ranges (namely $pIC_{50}>8$; $pIC_{50}$ ranging between 7 and 8; $pIC_{50}<7$) of $pIC_{50}$ values ($-\log IC_{50}$ (M)) obtained in the above-described test for the present compounds.

TABLE 4

| Co. No. | $pIC_{50}$ (GSK3beta) | $pIC_{50}$ (GSK3alpha) |
|---|---|---|
| 38 | >8 | >8 |
| 39 | >8 | >8 |
| 4 | >8 | 7-8 |
| 7 | >8 | >8 |

TABLE 4-continued

| Co. No. | pIC$_{50}$ (GSK3beta) | pIC$_{50}$ (GSK3alpha) |
|---|---|---|
| 37 | >8 | >8 |
| 9 | >8 | >8 |
| 8 | >8 | >8 |
| 10 | >8 | >8 |
| 33 | >8 | >8 |
| 3 | >8 | >8 |
| 1 | >8 | >8 |
| 13 | 7-8 | nd |
| 14 | 7-8 | >8 |
| 15 | 8 | >8 |
| 17 | 7-8 | >8 |
| 18 | 7-8 | 7-8 |
| 19 | 7-8 | >8 |
| 20 | 7-8 | >8 |
| 32 | >8 | >8 |
| 21 | >8 | >8 |
| 22 | >8 | >8 |
| 23 | >8 | >8 |
| 24 | >8 | >8 |
| 6 | >8 | >8 |
| 29 | 7-8 | >8 |
| 30 | >8 | >8 |
| 2 | >8 | >8 |
| 31 | >8 | >8 |
| 11 | >8 | >8 |
| 12 | >8 | 7-8 |
| 34 | >8 | >8 |
| 25 | 7-8 | >8 |
| 27 | >8 | >8 |
| 28 | >8 | >8 |
| 35 | >8 | >8 |
| 36 | >8 | >8 |
| 42 | >8 | >8 |
| 43 | >8 | >8 |
| 51 | >8 | >8 |
| 52 | >8 | >8 |
| 53 | >8 | >8 |
| 54 | >8 | >8 |
| 55 | >8 | >8 |
| 56 | >8 | >8 |
| 44 | >8 | >8 |
| 45 | >8 | >8 |
| 57 | >8 | >8 |
| 58 | >8 | >8 |
| 59 | >8 | >8 |
| 60 | >8 | >8 |
| 61 | >8 | >8 |
| 62 | >8 | >8 |
| 63 | >8 | >8 |
| 64 | >8 | >8 |
| 66 | 7-8 | 7-8 |
| 47 | >8 | >8 |
| 68 | 7 | 7-8 |
| 69 | >8 | 8 |
| 70 | 7 | 7-8 |
| 71 | 7-8 | >8 |
| 72 | 7-8 | >8 |
| 73 | >8 | >8 |
| 74 | 8 | >8 |
| 75 | 7-8 | >8 |
| 77 | >8 | >8 |
| 78 | 7-8 | 7-8 |
| 79 | 7-8 | 7-8 |
| 80 | >8 | >8 |
| 81 | >8 | >8 |
| 82 | 7-8 | >8 |
| 83 | 7-8 | 7-8 |
| 84 | >8 | >8 |
| 85 | 7-8 | >8 |
| 86 | >8 | >8 |
| 87 | 7-8 | >8 |
| 88 | >8 | >8 |
| 89 | >8 | >8 |
| 90 | >8 | >8 |
| 91 | >8 | >8 |
| 94 | >8 | >8 |
| 95 | >8 | >8 |
| 96 | 7-8 | 7-8 |
| 97 | >8 | >8 |
| 98 | >8 | >8 |
| 99 | >8 | >8 |
| 100 | >8 | >8 |
| 101 | >8 | >8 |
| 102 | >8 | >8 |
| 103 | <9 | >8 |
| 104 | >8 | >8 |
| 107 | >8 | >8 |
| 108 | >8 | >8 |
| 109 | >8 | >8 |
| 110 | >8 | >8 |
| 111 | >8 | >8 |
| 112 | >8 | >8 |
| 113 | >8 | >8 |
| 121 | 7-8 | 7-8 |
| 122 | >8 | >8 |
| 123 | >8 | >8 |
| 124 | >8 | >8 |
| 125 | >8 | >8 |
| 126 | >8 | >8 |
| 127 | >8 | >8 |
| 131 | 7-8 | 7-8 |
| 132 | >8 | >8 |
| 133 | >8 | >8 |
| 134 | >8 | >8 |
| 135 | >8 | >8 |
| 136 | >8 | >8 |
| 137 | >8 | >8 |
| 138 | >8 | >8 |
| 139 | >8 | >8 |
| 140 | >8 | >8 |
| 141 | 7-8 | 7-8 |
| 142 | >8 | >8 |
| 143 | >8 | >8 |
| 144 | >8 | >8 |
| 145 | >8 | >8 |
| 146 | >8 | >8 |
| 147 | >8 | >8 |
| 148 | >8 | >8 |
| 149 | 7-8 | >8 |
| 150 | >8 | >8 |
| 151 | >8 | >8 |
| 152 | >8 | >8 |
| 153 | >8 | >8 |
| 154 | 7-8 | 7-8 |
| 155 | 7-8 | >8 |
| 156 | >8 | >8 |
| 157 | >8 | >8 |
| 158 | >8 | >8 |
| 160 | 7-8 | 7-8 |
| 167 | >8 | >8 |
| 168 | >8 | >8 |
| 169 | >8 | >8 |
| 171 | >8 | >8 |
| 172 | >8 | >8 |
| 173 | >8 | >8 |
| 174 | >8 | >8 |
| 175 | >8 | >8 |
| 176 | 7-8 | 7-8 |
| 177 | 7 | 7-8 |
| 180 | 7-8 | 7-8 |
| 185 | >8 | >8 |
| 186 | 7-8 | >8 |
| 188 | >8 | >8 |
| 189 | >8 | >8 |
| 190 | 8 | >8 |
| 191 | >8 | >8 |
| 192 | >8 | >8 |
| 193 | 7-8 | 7-8 |
| 194 | 7-8 | >8 |
| 195 | 7-8 | >8 |
| 197 | >8 | >8 |
| 200 | 7-8 | >8 |

TABLE 4-continued

| Co. No. | pIC$_{50}$ (GSK3beta) | pIC$_{50}$ (GSK3alpha) |
|---|---|---|
| 201 | >8 | >8 |
| 202 | >8 | >8 |
| 203 | 7-8 | >8 |
| 205 | >8 | >8 |
| 206 | >8 | >8 |
| 207 | >8 | >8 |
| 208 | >8 | >8 |
| 209 | 7-8 | 7-8 |
| 210 | >8 | >8 |
| 212 | >8 | >8 |
| 214 | >8 | >8 |
| 216 | >8 | >8 |
| 217 | >8 | >8 |
| 218 | >8 | >8 |
| 219 | >8 | >8 |
| 220 | >8 | >8 |
| 221 | >8 | >8 |
| 223 | >8 | >8 |
| 227 | 7-8 | >8 |
| 228 | >8 | >8 |
| 229 | >8 | >8 |
| 235 | 7-8 | >8 |
| 237 | 7-8 | 8 |
| 238 | >8 | >8 |
| 239 | 7-8 | 8 |
| 240 | 7-8 | 7-8 |
| 241 | 7-8 | 7-8 |
| 243 | 7-8 | 7-8 |
| 246 | >8 | >8 |
| 247 | 7-8 | >8 |
| 248 | >8 | >8 |
| 249 | >8 | >8 |
| 254 | >8 | >8 |
| 255 | >8 | >8 |
| 256 | >8 | >8 |
| 257 | >8 | >8 |
| 258 | >8 | >8 |
| 259 | >8 | >8 |
| 260 | >8 | >8 |
| 261 | >8 | >8 |
| 262 | >8 | >8 |
| 264 | >8 | >8 |
| 265 | >8 | >8 |
| 266 | >8 | >8 |
| 267 | >8 | >8 |
| 268 | >8 | >8 |
| 269 | >8 | >8 |
| 270 | >8 | >8 |
| 271 | >8 | >8 |
| 272 | >8 | >8 |
| 273 | >8 | >8 |
| 274 | >8 | >8 |
| 275 | >8 | >8 |
| 276 | >8 | >8 |
| 277 | >8 | >8 |
| 278 | >8 | >8 |
| 279 | 7-8 | 7-8 |
| 285 | >8 | >8 |
| 286 | >8 | >8 |
| 287 | >8 | >8 |
| 289 | >8 | >8 |
| 290 | >8 | nd |
| 291 | 7-8 | >8 |
| 293 | <7 | >8 |
| 294 | >8 | >8 |
| 295 | 8 | >8 |
| 296 | 7-8 | 7-8 |
| 297 | 7-8 | 7-8 |
| 298 | >8 | >8 |
| 301 | 7-8 | >8 |
| 302 | 7-8 | >8 |
| 303 | 7-8 | >8 |
| 304 | >8 | >8 |
| 305 | 7-8 | >8 |
| 306 | >8 | >8 |
| 307 | >8 | >8 |

TABLE 4-continued

| Co. No. | pIC$_{50}$ (GSK3beta) | pIC$_{50}$ (GSK3alpha) |
|---|---|---|
| 308 | >8 | >8 |
| 309 | >8 | >8 |
| 310 | >8 | >8 |
| 311 | >8 | >8 |
| 312 | 7-8 | >8 |
| 313 | >8 | >8 |
| 314 | 7-8 | 7-8 |
| 315 | >8 | >8 |
| 316 | >8 | >8 |
| 317 | >8 | >8 |
| 318 | 7-8 | 7-8 |
| 319 | 7-8 | 7-8 |
| 320 | 7-8 | 7-8 |
| 321 | 7-8 | 7-8 |
| 325 | 7-8 | >8 |
| 326 | 7-8 | 7-8 |
| 327 | >8 | >8 |
| 328 | >8 | >8 |
| 329 | >8 | >8 |
| 330 | >8 | >8 |
| 331 | 7-8 | 7-8 |
| 332 | >8 | >8 |
| 333 | >8 | >8 |
| 334 | >8 | >8 |
| 335 | 7-8 | 7-8 |
| 336 | >8 | >8 |
| 337 | >8 | >8 |
| 338 | >8 | >8 | nd = not determined

The invention claimed is:

1. A compound of formula

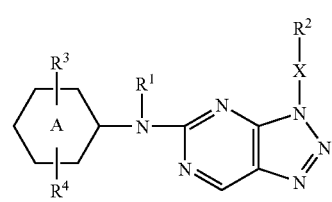

a pharmaceutically acceptable addition salt, a quaternary amine or a stereochemically isomeric form thereof, wherein ring A represents phenyl;

$R^1$ represents hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; or $C_{1-6}$alkyloxy$C_{1-6}$alkylcarbonyl optionally substituted with $C_{1-6}$alkyloxycarbonyl;

X represents a direct bond; —(CH$_2$)$_{n3}$— or —(CH$_2$)$_{n4}$—X$_{1a}$—X$_{1b}$—;

with $n_3$ representing an integer with value 1, 2, 3 or 4;

with $n_4$ representing an integer with value 1 or 2;

with X$_{1a}$ representing O, C(=O) or NR$^5$; and with X$_{1b}$ representing a direct bond or $C_{1-2}$alkyl;

$R^2$ represents $C_{3-7}$cycloalkyl; phenyl; a 4, 5, 6- or 7-membered monocyclic heterocycle containing at least one heteroatom selected from O, S or N; benzoxazolyl or a radical of formula

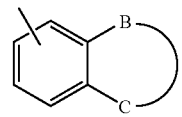

wherein —B—C— represents a bivalent radical of formula $CH_2$—$CH_2$—$CH_2$— (b-1);

—$CH_2$—$CH_2$—$CH_2$—$CH_2$— (b-2);

—$X_1$—$CH_2$—$CH_2$—$(CH_2)_n$— (b-3);

—$X_1$—$CH_2$—$(CH_2)_n$—$X_1$— (b-4);

—$X_1$—$(CH_2)_{n'}$—CH=CH— (b-5);

—CH=N—$X_1$— (b-6);

with $X_1$ representing O or $NR^5$;
n representing an integer with value 0, 1, 2 or 3;
n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkyloxy $C_{1-4}$alkyloxy, $C_{1-4}$alkylcarbonyl, $C_{1-4}$alkyloxycarbonyl, $C_{1-4}$alkyl-carbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo-$C_{1-6}$alkyl optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{1-6}$alkyloxy optionally substituted with at least one substituent selected from hydroxy, cyano, carboxyl, $C_{1-4}$alkyloxy, $C_{1-4}$alkylcarbonyl, $C_{1-4}$alkyl-oxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; polyhalo$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^6R^7$, —C(=O)—$NR^6R^7$, —$NR^5$—C(=O)—$NR^6R^7$, —S(=O)$_{n1}$—$R^8$ or —$NR^5$—S(=O)$_{n1}$—$R^8$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$ alkylcarbonyl; cyano; carboxyl; $NR^6R^7$; C(=O)$NR^6R^7$; —$NR^5$—C(=O)—$NR^6R^7$; —$NR^5$—C(=O)—$R^5$; —S(=O)$_{n1}$—$R^8$; —$NR^5$—S(=O)$_{n1}$—$R^8$; —S—CN; —$NR^5$—CN; aryloxy; arylthio; arylcarbonyl; aryl$C_{1-4}$alkyl; aryl$C_{1-4}$alkyloxy; a 5-or 6-membered monocyclic heterocycle containing at least one heteroatom selected from O, S or N and said 5-or 6-membered monocyclic heterocycle optionally being substituted with at least one substituent selected from $R^9$; or

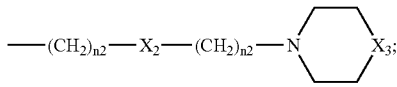

with n2 representing an integer with value 0, 1, 2, 3 or 4;

with $X_2$ representing O, $NR^5$ or a direct bond;
with $X_3$ representing O, $CH_2$, CHOH, CH—$N(R^5)_2$, $NR^5$ or
N—C(=O)—$C_{1-4}$alkyl;

$R^3$ represents halo; hydroxy; $C_{1-6}$alkyl optionally substituted with at least one substituent selected from hydroxy, cyano, carboxyl, $C_{1-4}$alkyloxy, $C_{1-4}$alkyloxy-$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; polyhalo$C_{1-6}$alkyl optionally substituted with at least one substituent selected from hydroxy, cyano, carboxyl, $C_{1-4}$alkyloxy, $C_{1-4}$alkyloxy-$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; $C_{1-6}$alkyloxy optionally substituted with one substituent selected from hydroxy, cyano, carboxyl, $C_{1-4}$alkyloxy, $C_{1-4}$alkylcarbonyl, $C_{1-4}$alkyloxy-carbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; polyhalo$C_{1-6}$alkyloxy optionally substituted with at least one substituent selected from hydroxy, cyano, carboxyl, $C_{1-4}$alkyloxy, $C_{1-4}$alkyloxy$C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—$NR^{6b}R^{7b}$, —$NR^5$—C(=O)—$NR^{6b}R^{7b}$, —S(=O)$_{n1}$—$R^{8a}$ or —$NR^5$—S(=O)$_{n1}$—$R^{8a}$; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo-$C_{1-6}$alkylcarbonyl; cyano; carboxyl; aryloxy; arylthio; arylcarbonyl; $NR^{6b}R^{7b}$; C(=O)—$NR^{6b}R^{7b}$; —$NR^5$—C(=O)—$NR^{6b}R^{7b}$; —$NR^5$—C(=O)—$R^5$; —S(=O)$_{n1}$—$R^{8a}$; —$NR^5$—S(=O)$_{n1}$—$R^{8a}$; —S—CN; or —$NR^5$—CN;

$R^4$ represents hydrogen; halo; hydroxy; $C_{1-4}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, —C(=O)—$NR^{10}R^{11}$, —$NR^5$—C(=O)—$NR^{10}R^{11}$, —S(=O)$_{n1}$—$R^{12}$ or —$NR^5$—S(=O)$_{n1}$—$R^{12}$; $C_{2-4}$alkenyl or $C_{2-4}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{10}R^{11}$, —C(=O)—$NR^{10}R^{11}$, —$NR^5$—C(=O)—$NR^{10}R^{11}$, —S(=O)$_{n1}$—$R^{12}$ or —$NR^5$—S(=O)$_{n1}$—$R^{12}$; polyhalo$C_{1-3}$alkyl; $C_{1-4}$alkyloxy optionally substituted with carboxyl; polyhalo$C_{1-3}$alkyloxy; $C_{1-4}$alkylthio; polyhalo$C_{1-3}$alkylthio; $C_{1-4}$alkyloxycarbonyl; $C_{1-4}$alkylcarbonyloxy; $C_{1-4}$alkylcarbonyl; polyhalo$C_{1-4}$alkylcarbonyl; nitro; cyano; carboxyl; $NR^{10}R^{11}$; C(=O)$NR^{10}R^{11}$; —$NR^5$—C(=O)—$NR^{10}R^{11}$; —$NR^5$—C(=O)—$R^5$; —S(=O)$_{n1}$—$R^{12}$; —$NR^5$—S(=O)$_{n1}$—$R^{12}$; —S—CN; or —$NR^5$—CN;

$R^5$ represents hydrogen; $C_{1-4}$alkyl or $C_{2-4}$alkenyl;

$R^6$ and $R^7$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkylcarbonyl; adamantanylcarbonyl; $C_{1-4}$alkyloxy$C_{1-4}$alkyl; $C_{1-4}$alkyl substituted with $C_{1-4}$alkyl—$NR^5$—;

$C_{1-6}$alkyl optionally substituted with at least one substituent selected from halo, hydroxy, cyano, carboxyl, $C_{1-4}$alkyloxy, polyhalo—$C_{1-4}$alkyl, $C_{1-4}$alkyloxy$C_{1-4}$alkyloxy, $NR^{6a}R^{7a}$, $C(=O)NR^{6a}R^{7a}$ or

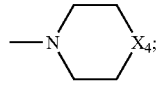

with $X_4$ representing O, $CH_2$, CHOH, CH—$N(R^5)_2$, $NR^5$ or N—$C(=O)$—$C_{1-4}$alkyl;

$R^{6a}$ and $R^{7a}$ each independently represent hydrogen; $C_{1-4}$alkyl; $C_{1-4}$alkylcarbonyl or a 5- or 6-membered monocyclic heterocycle containing at least one heteroatom selected from O, S or N;

$R^{6b}$ and $R^{7b}$ each independently represent hydrogen; cyano; $C_{1-6}$alkylcarbonyl optionally substituted with $C_{1-4}$alkyloxy or carboxyl; $C_{1-6}$alkyloxycarbonyl; $C_{3-7}$cycloalkyl-carbonyl; adamantanylcarbonyl; $C_{1-4}$alkyloxy$C_{1-4}$alkyl; $C_{1-4}$alkyl substituted with $C_{1-4}$alkyl—$NR^5$—; $C_{1-6}$alkyl optionally substituted with at least one substituent selected from halo, hydroxy, cyano, carboxyl, $C_{1-4}$alkyloxy, polyhalo$C_{1-4}$alkyl, $C_{1-4}$alkyloxy-$C_{1-4}$alkyloxy, $NR^{6c}R^{7c}$ or $C(=O)NR^{6c}R^{7c}$;

$R^{6c}$ and $R^{7c}$ each independently represent hydrogen; $C_{1-4}$alkyl or $C_{1-4}$alkylcarbonyl;

$R^8$ represents $C_{1-4}$alkyl optionally substituted with hydroxy; polyhalo$C_{1-4}$alkyl or $NR^6R^7$;

$R^{8a}$ represents $C_{1-4}$alkyl optionally substituted with hydroxy; polyhalo$C_{1-4}$alkyl or $NR^{6b}R^{7b}$;

$R^9$ represents halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —$C(=O)$—$NR^6R^7$, —$NR^5$—$C(=O)$—$NR^6R^7$, —$S(=O)_{n1}$—$R^8$ or —$NR^5$—$S(=O)_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —$C(=O)$—$NR^6R^7$, —$NR^5$—$C(=O)$—$NR^6R^7$, —$S(=O)_{n1}$ —$R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; cyano; carboxyl; $NR^6R^7$; $C(=O)NR^6R^7$; —$NR^5$—$C(=O)$—$NR^6R^7$; —$NR^5$—$C(=O)$—$R^5$; —$S(=O)_{n1}$—$R^8$; —$NR^5$—$S(=O)_{n1}$—$R^8$; —S—CN; or —$NR^5$—CN;

$R^{10}$ and $R^{11}$ each independently represent hydrogen; $C_{1-6}$alkyl; cyano; $C_{1-6}$alkylcarbonyl; $C_{1-4}$alkyloxy$C_{1-4}$alkyl; or $C_{1-4}$alkyl substituted with $C_{1-4}$alkyl-$NR^5$—;

$R^{12}$ represents $C_{1-4}$alkyl or $NR^{10}R^{11}$;

n1 represents an integer with value 1 or 2;

aryl represents phenyl or phenyl substituted with at least one substituent selected from halo, $C_{1-6}$alkyl, $C_{3-7}$cycloalkyl, $C_{1-6}$alkyloxy, cyano, nitro, polyhalo$C_{1-6}$alkyl or polyhalo$C_{1-6}$alkyloxy.

2. The compound according to claim 1 wherein

X represents a direct bond; —$(CH_2)_{n3}$— or —$(CH_2)_{n4}$—$X_a$—$X_b$—;

with $n_3$ representing an integer with value 1, 2, 3 or 4;

with $n_4$ representing an integer with value 1 or 2;

with $X_a$ representing O or $NR^5$; and with $X_b$ representing a direct bond or $C_{1-2}$alkyl;

$R^2$ represents $C_{3-7}$cycloalkyl; phenyl or a 4, 5, 6- or 7-membered monocyclic heterocycle containing at least one heteroatom selected from O, S or N; or a radical of formula

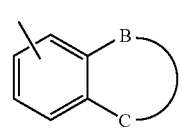

(a-1)

wherein —B—C— represents a bivalent radical of formula $CH_2$—$CH_2$—$CH_2$— (b-1);

—$CH_2$—$CH_2$—$CH_2$—$CH_2$— (b-2);

—$X_1$—$CH_2$—$CH_2$—$(CH_2)_n$— (b-3);

—$X_1$—$CH_2$—$(CH_2)_n$—$X_1$— (b-4);

—$X_1$—$(CH_2)_{n'}$—CH=CH— (b-5);

with $X_1$ representing O or $NR^5$;

n representing an integer with value 0, 1, 2 or 3;

n' representing an integer with value 0 or 1;

wherein said $R^2$ substituent, where possible, may optionally be substituted with at least one substituent selected from halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —$C(=O)$—$NR^6R^7$, —$NR^5$—$C(=O)$—$NR^6R^7$, —$S(=O)_{n1}$—$R^8$ or —$NR^5$—$S(=O)_{n1}$—$R^8$; $C_{2-6}$alkenyl or $C_{2-6}$alkynyl, each optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^6R^7$, —$C(=O)$—$NR^6R^7$, —$NR^5$—$C(=O)$—$NR^6R^7$, —$S(=O)_{n1}$—$R^8$ or —$NR^5$—$S(=O)_{n1}$—$R^8$; polyhalo$C_{1-6}$alkyl; $C_{1-6}$alkyloxy optionally substituted with carboxyl; polyhalo$C_{1-6}$alkyloxy; $C_{1-6}$alkylthio; polyhalo$C_{1-6}$alkylthio; $C_{1-6}$alkyloxycarbonyl; $C_{1-6}$alkylcarbonyloxy; $C_{1-6}$alkylcarbonyl; polyhalo$C_{1-6}$alkylcarbonyl; cyano; carboxyl; $NR^6R^7$; $C(=O)NR^6R^7$; —$NR^5$—$C(=O)$—$NR^6R^7$; —$NR^5$—$C(=O)$—$R^5$; —$S(=O)_{n1}$—$R^8$; —$NR^5$—$S(=O)_{n1}$—$R^8$; —S—CN; —$NR^5$—CN; aryloxy; arylthio; arylcarbonyl; aryl$C_{1-4}$alkyl; aryl$C_{1-4}$alkyloxy; a 5-or 6-membered monocyclic heterocycle containing at least one heteroatom selected from O, S or N and said 5-or 6-membered monocyclic heterocycle optionally being substituted with at least one substituent selected from $R^9$; or

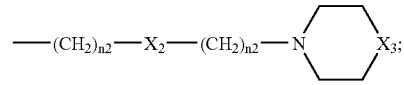

with n2 representing an integer with value 0, 1, 2, 3 or 4;

with $X_2$ representing O, $NR^5$ or a direct bond;

with $X_3$ representing O or $NR^5$;

$R^3$ represents halo; hydroxy; $C_{1-6}$alkyl optionally substituted with at least one substituent selected from hydroxy, cyano, carboxyl, $C_{1-4}$alkyloxy, $C_{1-4}$alkylcarbonyl, $C_{1-4}$alkyloxycarbonyl, $C_{1-4}$alkylcarbonyloxy, $NR^{6b}R^{7b}$, —C(=O)—NR$^{6b}$R$^{7b}$, —NR$^5$—C(=O)—NR$^{6b}$R$^{7b}$, —S(=O)$_{n1}$—R$^{8a}$ or —NR$^5$—S(=O)$_{n1}$—R$^{8a}$; C$_{2-6}$alkenyl or C$_{2-6}$alkynyl, each optionally substituted with at least one substituent selected from hydroxy, cyano, carboxyl, C$_{1-4}$alkyloxy, C$_{1-4}$alkylcarbonyl, C$_{1-4}$alkyloxycarbonyl, C$_{1-4}$alkylcarbonyloxy, NR$^{6b}$R$^{7b}$, —C(=O)—NR$^{6b}$R$^{7b}$, —NR$^5$—C(=O)—NR$^{6b}$R$^{7b}$, —S(=O)$_{n1}$—R$^{8a}$ or —NR$^5$—S(=O)$_{n1}$—R$^{8a}$; polyhaloC$_{1-6}$alkyl; C$_{1-6}$alkyloxy optionally substituted with carboxyl; polyhaloC$_{1-6}$alkyloxy; C$_{1-6}$alkylthio; polyhaloC$_{1-6}$alkylthio; C$_{1-6}$alkyloxycarbonyl; C$_{1-6}$alkylcarbonyloxy; C$_{1-6}$alkyl-carbonyl; polyhaloC$_{1-6}$alkylcarbonyl; nitro; cyano; carboxyl; NR$^{6b}$R$^{7b}$; C(=O)NR$^{6b}$R$^{7b}$; —NR$^5$—C(=O)—NR$^{6b}$R$^{7b}$; —NR$^5$—C(=O)—R$^5$; —S(=O)$_{n1}$—R$^{8a}$; —NR$^5$—S(=O)$_{n1}$—R$^{8a}$; —S—CN; or —NR$^5$—CN;

R$^5$ represents hydrogen or C$_{1-4}$alkyl;

R$^6$ and R$^7$ each independently represent hydrogen; cyano; C$_{1-6}$alkylcarbonyl; C$_{1-4}$alkyloxyC$_{1-4}$alkyl; C$_{1-4}$alkyl substituted with C$_{1-4}$alkyl-NR$^5$—; C$_{1-6}$alkyl optionally substituted with hydroxy, C$_{1-4}$alkyloxy, C$_{1-4}$alkyloxyC$_{1-4}$alkyloxy, NR$^{6a}$R$^{7a}$, C(=O)NR$^{6a}$R$^{7a}$ or

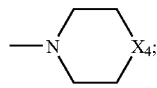

with X$_4$ representing O or NR$^5$;

R$^{6a}$ and R$^{7a}$ each independently represent hydrogen; C$_{1-4}$alkyl; C$_{1-4}$alkylcarbonyl or a 5- or 6-membered monocyclic heterocycle containing at least one heteroatom selected from O, S or N;

R$^{6b}$ and R$^{7b}$ each independently represent hydrogen; cyano; C$_{1-6}$alkylcarbonyl; C$_{1-4}$alkyloxyC$_{1-4}$alkyl; C$_{1-4}$alkyl substituted with C$_{1-4}$alkyl-NR$^5$—; C$_{1-6}$alkyl optionally substituted with hydroxy, C$_{1-4}$alkyloxy, C$_{1-4}$alkyloxyC$_{1-4}$alkyloxy, NR$^{6a}$R$^{7a}$ or C(=O)NR$^{6a}$R$^{7a}$;

R$^8$ represents C$_{1-4}$alkyl, polyhaloC$_{1-4}$alkyl or NR$^6$R$^7$;

R$^{8a}$ represents C$_{1-4}$alkyl, polyhaloC$_{1-4}$alkyl or NR$^{6b}$R$^{7b}$.

3. The compound according to claim 1 wherein R$^1$ represents hydrogen; X represents a direct bond or —(CH$_2$)$_{n3}$—; R$^2$ represents phenyl or a radical of formula (b-4), wherein said R$^2$ may optionally be substituted with at least one substituent, in particular 1, 2 or 3 substituents, selected from halo; C$_{1-6}$alkyl optionally substituted with at least one substituent selected from hydroxy, cyano, carboxyl, NR$^6$R$^7$, C(=O)NR$^6$R$^7$, C$_{1-4}$alkyloxy or C$_{1-4}$alkyloxyC$_{1-4}$alkyloxy; C$_{1-6}$alkyloxy;

C$_{1-6}$alkyloxycarbonyl; C$_{1-4}$alkyloxyC$_{1-6}$alkyloxy; cyano; carboxyl; C(=O)NR$^6$R$^7$; —S(=O)$_{n1}$—R$^8$; arylC$_{1-4}$alkyloxy; or a 5-or 6-membered heterocycle containing at least one heteroatom selected from O, S or N and said 5-or 6-membered heterocycle optionally being substituted with at least one substituent selected from R$^9$; R$^3$ represents halo; hydroxy; C$_{1-6}$alkyl optionally substituted with at least one substituent selected from hydroxy, cyano, carboxyl, C$_{1-4}$alkyloxy, NR$^{6b}$R$^{7b}$ or C(=O)NR$^{6b}$R$^{7b}$;

C$_{2-6}$alkenyl optionally substituted with at least one substituent selected from carboxyl or C$_{1-4}$alkyl-oxycarbonyl; polyhaloC$_{1-6}$alkyloxy; C$_{1-6}$alkyloxy optionally substituted with C$_{1-4}$alkyloxy; C$_{1-6}$alkylthio; C$_{1-6}$alkyloxycarbonyl; C$_{1-6}$alkylcarbonyl; cyano; carboxyl; NR$^{6b}$R$^{7b}$; C(=O)NR$^{6b}$R$^{7b}$; —NR$^5$—C(=O)—R$^5$; —S(=O)$_{n1}$—R$^8$; —NR$^5$—S(=O)$_{n1}$—R$^8$; or —S—CN;

R$^4$ represents hydrogen; halo; C$_{1-6}$alkyl; cyano; hydroxy; C$_{1-6}$alkyloxycarbonyl; C$_{1-6}$alkyloxy; carboxyl; or NR$^6$R$^7$.

4. The compound according to claim 1 wherein R$^1$ represents hydrogen; X represents a direct bond; R$^2$ represents phenyl wherein said R$^2$ may optionally be substituted with at least one substituent, in particular 1, 2 or 3 substituents, selected from halo; C$_{1-6}$alkyl substituted with one substituent selected from hydroxy, cyano, NR$^6$R$^7$, C(=O)NR$^6$R$^7$, C$_{1-4}$alkyloxy or C$_{1-4}$alkyloxyC$_{1-4}$alkyloxy; C$_{1-6}$alkyloxy; C$_{1-6}$alkyloxycarbonyl; C$_{1-4}$alkyloxyC$_{1-6}$alkyloxy; C(=O)NR$^6$R$^7$;

—S(=O)$_{n1}$—R$^8$; or a 5-or 6-membered heterocycle containing at least one heteroatom selected from O, S or N and said 5-or 6-membered heterocycle optionally being substituted with at least one substituent selected from R$^9$; R$^3$ represents halo; hydroxy; C$_{1-6}$alkyl optionally substituted with at least one substituent selected from hydroxy, cyano, carboxyl, C$_{1-4}$alkyloxy, NR$^{6b}$R$^{7b}$ or C(=O)NR$^{6b}$R$^{7b}$; C$_{2-6}$alkenyl optionally substituted with at least one substituent selected from carboxyl or C$_{1-4}$alkyloxycarbonyl; polyhaloC$_{1-6}$alkyloxy; C$_{1-6}$alkyloxy optionally substituted with
C$_{1-4}$alkyloxy or NR$^{6b}$R$^{7b}$; C$_{1-6}$alkylthio; C$_{1-6}$alkyloxycarbonyl; C$_{1-6}$alkylcarbonyl; cyano; carboxyl; NR$^{6b}$R$^{7b}$; C(=O)NR$^{6b}$R$^{7b}$; —S(=O)$_{n1}$—R$^8$; —NR$^5$—C(=O)—R$^5$; or
—NR$^5$—S(=O)$_{n1}$—R$^8$; R$^4$ represents hydrogen; halo; C$_{1-6}$alkyl; hydroxy; C$_{1-6}$alkyl-oxycarbonyl; C$_{1-6}$alkyloxy; carboxyl; or NR$^6$R$^7$.

5. The compound according to claim 1 wherein the R$^3$ substituent is linked to ring A in meta position compared to the NR$^1$ linker.

6. The compound according to claim 1 wherein the R$^3$ substituent is linked to ring A in para position compared to the NR$^1$ linker.

7. The compound according to claim 1 wherein R$^3$ represents NR$^{6b}$R$^{7b}$.

8. The compound according to claim 1 wherein X represents a direct bond.

9. The compound according to claim 1 wherein R$^2$ represents C$_{3-7}$cycloalkyl; phenyl; a 4, 5, 6- or 7-membered monocyclic heterocycle containing at least one heteroatom selected from O, S or N; benzoxazolyl or a radical of formula (a-1) wherein said R$^2$ substituent is substituted with at least one substituent selected from C$_{1-6}$alkyl substituted with NR$^6$R$^7$; C$_{2-6}$alkenyl or C$_{2-6}$alkynyl, each substituted with NR$^6$R$^7$; polyhaloC$_{1-6}$alkyl substituted with NR$^6$R$^7$; C$_{1-6}$alkyloxy substituted with NR$^6$R$^7$; polyhaloC$_{1-6}$alkyloxy substituted with NR$^6$R$^7$; or NR$^6$R$^7$.

10. The compound according to claim 1 wherein R$^3$ represents C$_{1-6}$alkyl substituted with NR$^{6b}$R$^{7b}$; C$_{2-6}$alkenyl or C$_{2-6}$alkynyl, each substituted with NR$^{6b}$R$^{7b}$; polyhaloC$_{1-6}$alkyl substituted with NR$^{6b}$R$^{7b}$; C$_{1-6}$alkyloxy substituted with NR$^{6b}$R$^{7b}$; polyhaloC$_{1-6}$alkyloxy substituted with NR$^{6b}$R$^{7b}$; or NR$^{6b}$R$^{7b}$.

11. The compound according to claim 1 wherein R$^2$ represents C$_{3-7}$cycloalkyl; phenyl; a 4, 5, 6- or 7-membered monocyclic heterocycle containing at least one heteroatom selected from O, S or N; benzoxazolyl or a radical of formula (a-1), wherein said R$^2$ substituent is substituted with at least one substituent selected from halo; polyhaloC$_{1-6}$alkyl optionally substituted with at least one substituent selected from hydroxy, cyano, carboxyl, C$_{1-4}$alkyloxy, C$_{1-4}$alkyloxy-C$_{1-4}$ alkyloxy, C$_{1-4}$alkylcarbonyl, C$_{1-4}$alkyloxycarbonyl, C$_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$; polyhalo-C$_{1-6}$alkyloxy optionally substituted with at least one substituent selected from hydroxy, cyano, carboxyl, C$_{1-4}$alkyloxy, C$_{1-4}$alkyloxyC$_{1-4}$alkyloxy, C$_{1-4}$alkylcarbonyl, C$_{1-4}$alkyloxycarbonyl, C$_{1-4}$alkylcarbonyloxy, NR$^6$R$^7$, —C(=O)—NR$^6$R$^7$, —NR$^5$—C(=O)—NR$^6$R$^7$, —S(=O)$_{n1}$—R$^8$ or —NR$^5$—S(=O)$_{n1}$—R$^8$.

12. The compound according to claim 1 wherein the compound is selected from the group consisting of

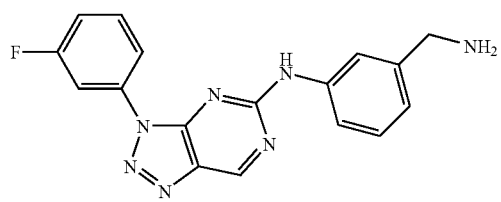

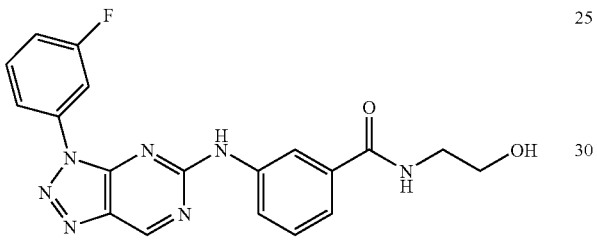

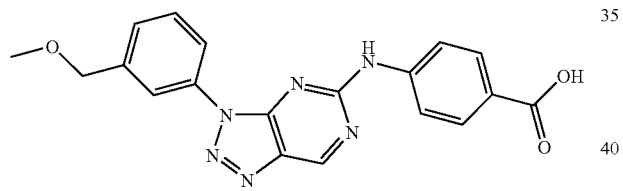

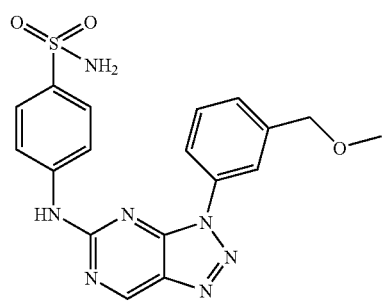

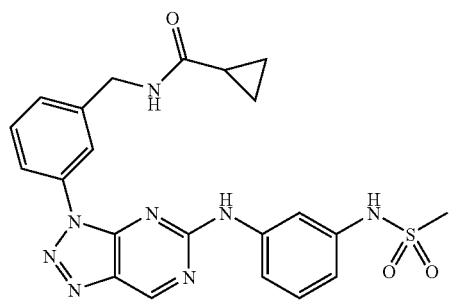

-continued

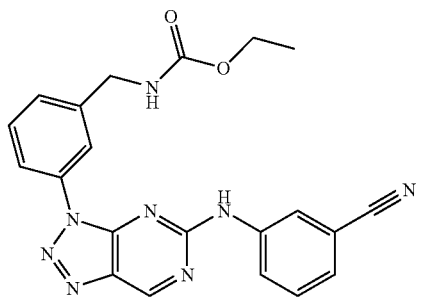

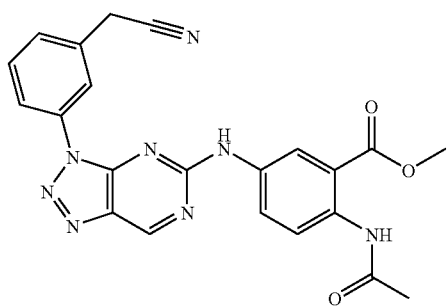

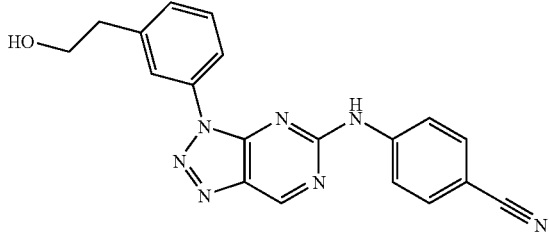

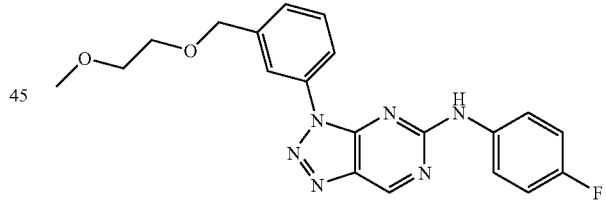

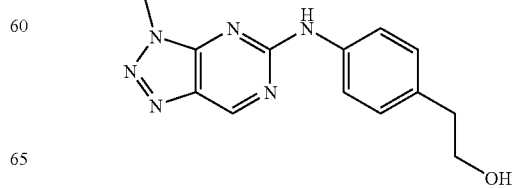

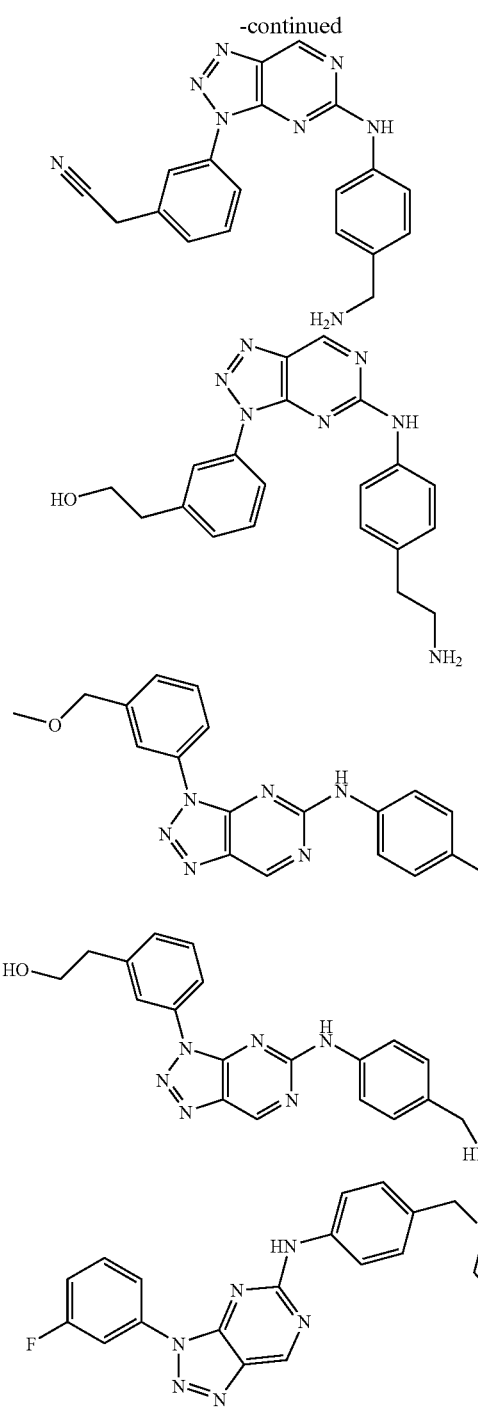

a pharmaceutically acceptable addition salt, a quaternary amine or a stereochemically isomeric form thereof.

13. A pharmaceutical composition comprising a pharmaceutically acceptable carrier and the compound of claim 1.

14. A pharmaceutical composition comprising a pharmaceutically acceptable carrier and as active ingredient a compound as claimed in claim 1.

15. A process for preparing a pharmaceutical composition comprising intimately mixing a compound as claimed in claim 1 with a pharmaceutically acceptable carrier.

16. A process for preparing a compound as claimed in claim 1, comprising a) cyclizing an intermediate of formula (II) in the presence of a nitrite salt, a suitable solvent, and a suitable acid,

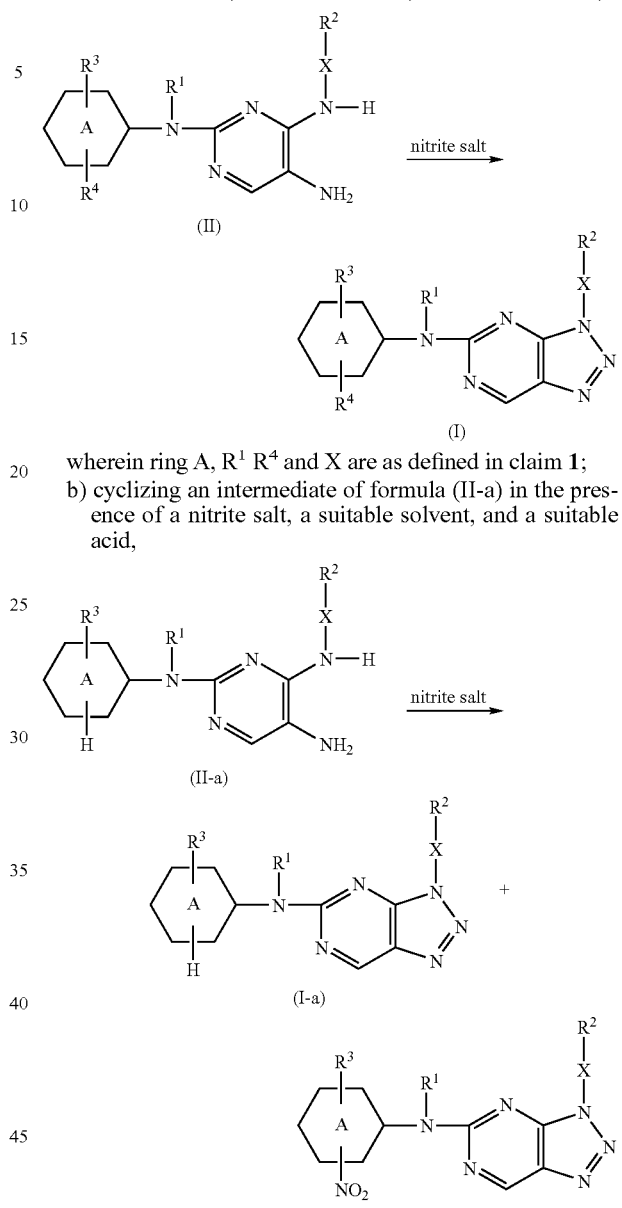

wherein ring A, $R^1$ $R^4$ and X are as defined in claim 1;

b) cyclizing an intermediate of formula (II-a) in the presence of a nitrite salt, a suitable solvent, and a suitable acid, wherein ring A, $R^1$ $R^3$ and X are as defined in claim 1;

c) cyclizing an intermediate of formula (II-b) in the presence of a nitrite salt, a suitable solvent, and a suitable acid,

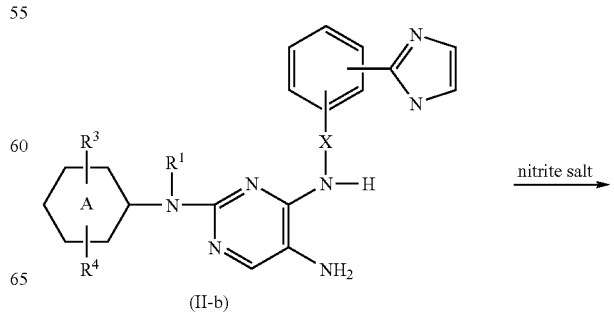

-continued

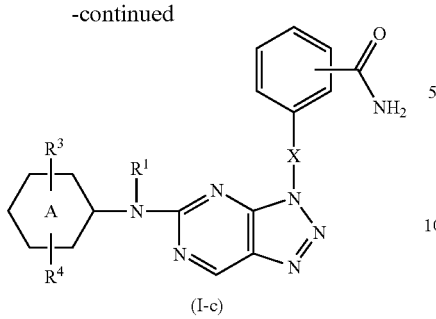

(I-c)

wherein ring A, $R^1$, $R^3$, $R^4$ and X are as defined in claim 1;

d) reacting an intermediate of formula (III) with an intermediate of formula (IV) in the presence of a suitable solvent,

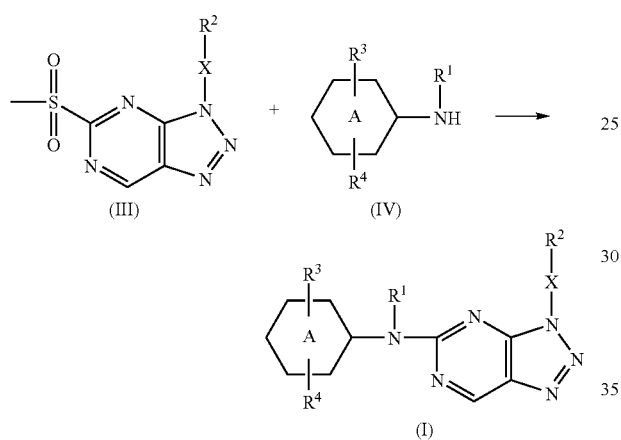

wherein ring A, $R^1$ to $R^4$ and X are as defined in claim 1;

e) reacting an intermediate of formula (III) with an intermediate of formula (IV) in the presence of a suitable solvent, and optionally in the presence of a suitable base,

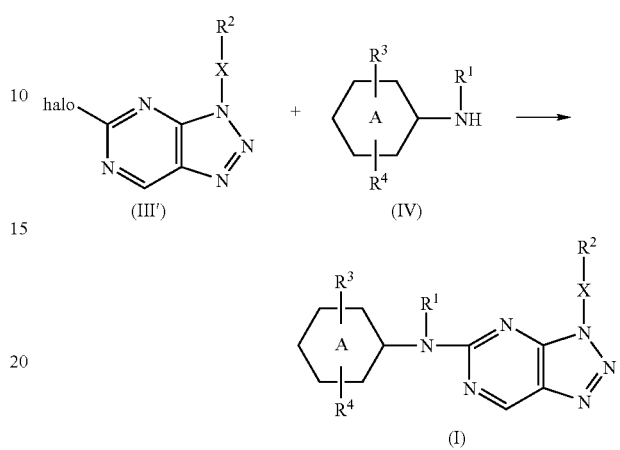

or, optionally, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, optionally, preparing stereochemically isomeric forms or customary amine forms thereof.

\* \* \* \* \*